United States Patent
Sitharaman et al.

(10) Patent No.: US 10,610,607 B2
(45) Date of Patent: *Apr. 7, 2020

(54) MAGNETIC GRAPHENE-LIKE NANOPARTICLES OR GRAPHITIC NANO- OR MICROPARTICLES AND METHOD OF PRODUCTION AND USES THEREOF

(71) Applicant: The Research Foundation for The State University of New York, Albany, NY (US)

(72) Inventors: Balaji Sitharaman, Coram, NY (US); Bhavna S. Paratala, Karnataka (IN)

(73) Assignee: The Research Foundation for The State University of New York, Albany, NY (US)

(*) Notice: Subject to any disclaimer, the term of this patent is extended or adjusted under 35 U.S.C. 154(b) by 84 days.

This patent is subject to a terminal disclaimer.

(21) Appl. No.: 15/644,172

(22) Filed: Jul. 7, 2017

(65) Prior Publication Data
US 2017/0312374 A1    Nov. 2, 2017

Related U.S. Application Data

(63) Continuation of application No. 14/116,102, filed as application No. PCT/US2012/036790 on May 7, 2012, now Pat. No. 9,713,650.

(60) Provisional application No. 61/483,309, filed on May 6, 2011.

(51) Int. Cl.
| | |
|---|---|
| A61B 5/055 | (2006.01) |
| A61K 49/10 | (2006.01) |
| B82Y 30/00 | (2011.01) |
| B82Y 40/00 | (2011.01) |
| B82Y 15/00 | (2011.01) |
| C01B 32/192 | (2017.01) |
| C01B 32/184 | (2017.01) |
| A61K 49/00 | (2006.01) |

(52) U.S. Cl.
CPC ............. *A61K 49/10* (2013.01); *B82Y 15/00* (2013.01); *B82Y 30/00* (2013.01); *B82Y 40/00* (2013.01); *C01B 32/184* (2017.08); *C01B 32/192* (2017.08); *A61K 49/0095* (2013.01); *C01B 2204/20* (2013.01)

(58) Field of Classification Search
None
See application file for complete search history.

(56) References Cited

U.S. PATENT DOCUMENTS

| | | |
|---|---|---|
| 9,713,650 B2 | 7/2017 | Sitharaman et al. |
| 2008/0213189 A1 | 9/2008 | Lee et al. |
| 2009/0053512 A1 | 2/2009 | Pyun et al. |
| 2009/0087493 A1 | 4/2009 | Dai et al. |
| 2009/0114883 A1 | 5/2009 | Collier et al. |
| 2009/0220431 A1 | 9/2009 | Cheon et al. |
| 2014/0161730 A1 | 6/2014 | Sitharaman et al. |
| 2017/0312374 A1 | 11/2017 | Sitharaman et al. |

FOREIGN PATENT DOCUMENTS

| | | |
|---|---|---|
| CN | 101327926 A | 12/2008 |
| CN | 101474406 A | 7/2009 |
| CN | 101525436 A | 9/2009 |
| CN | 101650977 A | 2/2010 |
| CN | 102068705 A | 5/2011 |
| CN | 102397563 A | 4/2012 |
| WO | 2010/029550 A2 | 3/2010 |
| WO | 2012/154677 A1 | 11/2012 |

OTHER PUBLICATIONS

Wang et al. (Electrochimica Acta 2010, 55, 6812-6817).*
Chen S. et al., "Graphene Oxide-MnO2 Nanocomposites for Supercapacitors", ACSnano 4(5):2822-2830 (2010).
Dresselhaus M.S. et al., "Intercalation Compounds of Graphite", Advances in Physics 51(1):1-186 (2002).
Geng Y. et al., "Effects of Stage, Intercalant Species and Expansion Technique on Exfoliation of Graphite Intercalation Compound into Graphene Sheets", Journal of Nanoscience and Nanotechnology 11:1084-1091 (2011).
He H. et al., "Supraparamagnetic, Conductive, and Processable Multifunctional Graphene Nanosheets Coated With High-Density Fe3O4 Nanoparticles", ACS Applied Materials & Interfaces 2(11):3201-3210 (2010).
Hong H. et al., "Molecular Imaging With Single-Walled Carbon Nanotubes", Nano Today 4(3):252-261 (2009).
Leung K C-F et al., "Biological and Magnetic Contrast Evaluation of Shape-Selective Mn—Fe Nanowires", IEEE Transactions on NanoBioscience [online], vol. 8(2):(2 pages), retrieved from the Internet: URL: http://ieeexplore.ieee.org/xpl/articleDetails.jsp arnumber=4912397, abstract (Jun. 2009).
Sarmeo D. et al., "Intercalation of Manganese Chloride into Mesophase Pitch-Based Graphite Fibers Via Gaseous Complexes", Carbon 39:2049-2058 (2001).

(Continued)

*Primary Examiner* — Michael G. Hartley
*Assistant Examiner* — Melissa J Perreira
(74) *Attorney, Agent, or Firm* — Scully, Scott, Murphy & Presser, P.C.

(57) ABSTRACT

The present invention provides a magnetic graphene-like nanoparticle or graphitic nano- or microparticle. The magnetic graphene-like nanoparticle or graphitic nano- or microparticle of the invention exhibits a high relaxivity, and is useful as a MRI contrast agent. The present invention also provides a composition for use with MRI imaging, comprising a sufficient amount of the magnetic graphene-like nanoparticles or graphitic nano- or microparticles and one or more physiologically acceptable carriers or excipients. The present invention also provides methods of using the magnetic graphene-like nanoparticles or graphitic nano- or microparticles as MRI contrast agents. The present invention further provides methods of producing the magnetic graphene-like nanoparticle or graphitic nano- or microparticle.

6 Claims, 42 Drawing Sheets

(56) References Cited

OTHER PUBLICATIONS

Wu M. et al., "Electronic Structure of Substitutionally Mn-Doped Graphene", New Journal of Physics 12:1-11 (2010).
Zou Y-H et al., "The Influence of Temperature on Magnetic and Microwave Absorption Properties of Fe/Graphite Oxide Nanocomposites", Journal of Magnetism and Magnetic Materials 302(2):343-347 (Jul. 2006).
European Communication dated Sep. 13, 2016 received in European Application No. 12 781 824.3.
Extended Supplementary European Search Report dated Apr. 16, 2015 received from Application No. 12781824.3.
Chinese Office Action dated Apr. 1, 2016 received from Chinese Application No. 201280033576.7, together with an English-language translation.
Chinese Office Action dated Sep. 28, 2015 received from Chinese Application No. 201280033576.7, together with an English-language translation.
Japanese Notice of Reasons for Rejection dated Sep. 5, 2016 received from Japanese Application No. 2014-510397, together with an English-language translation.
Japanese Notice of Reasons for Rejection dated Feb. 29, 2016 received from Japanese Application No. 2014-510397, together with an English-language translation.
U.S. Final Office Action dated Nov. 28, 2016 received in U.S. Appl. No. 14/116,102.
U.S. Non-Final Office Action dated Jun. 8, 2016 received in U.S. Appl. No. 14/116,102.
U.S. Final Office Action dated Feb. 17, 2016 received in U.S. Appl. No. 14/116,102.
U.S. Non-Final Office Action dated Jul. 7, 2015 received in U.S. Appl. No. 14/116,102.
Chinese Office Action dated Sep. 30, 2016 received from Chinese Application No. 201280033576.7, together with an English-language translation.
Canadian Examination Report dated May 31, 2018 received in Canadian Patent Application No. 2,835,262.
Korean Office Action dated Jun. 19, 2018 received in Korean Patent Application No. 10-2013-7031518, together with an English-language translation.

* cited by examiner

MAGNETIC GRAPHENE-LIKE NANOPARTICLES OR GRAPHITIC NANO- OR MICROPARTICLES AND METHOD OF PRODUCTION AND USES THEREOF

REFERENCE TO RELATED APPLICATIONS

The present application is a continuation of a co-pending application having U.S. Ser. No. 14/116,102, filed on Feb. 4, 2014, which is a 371 of International application having Serial No. PCT/US2012/036790, filed on May 7, 2012, which claims the benefit of priority from U.S. Provisional Application No. 61/483,309, filed on May 6, 2011, the content of which is incorporated herein by reference in its entirety.

FIELD OF THE INVENTION

The present invention relates to magnetic graphene-like nanoparticles or graphitic nano- or microparticles and method of production thereof. The present invention also relates to methods of using the magnetic graphene-like nanoparticles or graphitic nano- or microparticles as MRI contrast agents.

BACKGROUND OF THE INVENTION

MRI is primarily used to non-invasively render anatomical details for improved diagnosis of many pathologies and diseases (Sitharaman, B. & Wilson, L. J. Gadofullerenes and Gadonanotubes: A new paradigm for high-performance magnetic resonance imaging contrast agent probes Journal of Biomedical Nanotechnology 3, 342-352 (2007); Pan, D. et al. Revisiting an old friend: manganese-based MRI contrast agents. WIREs Nanomedicine and Nanobiotechnology 3, 162-173 (2010)). The development of MRI has led concurrently to increased use of chemical contrast-enhancement products called contrast agents (CAs) which improve detection of pathologic lesions by increasing sensitivity and diagnostic confidence.

The two main types are T1 and T2 MRI CAs, and affect (decrease) the longitudinal T1 and transverse T2 relaxation times of water protons, respectively. The quantitative measure of their effectiveness to accelerate the relaxation process of the water protons is known as relaxivity; the change in relaxation rate (inverse of relaxation time) per unit concentration of the MRI CA. The widely-used clinical T1 MRI CAs are mainly synthesized as metal-ion chelate complexes, where the metal ion is the lanthanoid element gadolinium ($Gd^{3+}$), or the inner-transitional element manganese ($Mn^{2+}$). A large body of experimental and theoretical research done in the last three decades now offers good understanding of the relaxation mechanism, and underlying structural, chemical and molecular dynamic properties that influence the relaxivity of these paramagnetic-ion chelate complexes (Aime et al., 1998, Chemical Society Reviews 27: 19-29; Caravan et al., 1999, Chem Rev 99: 2293-2352; and Lauffer, 1987, Chem Rev 87: 901-927). Theory suggests that the relaxivity of these MRI contrast agents is sub-optimal, and predicts the possibility of developing new contrast agents up to at least fifty to hundred times greater relaxivity (Merbach et al., 2001, The Chemistry of Contrast Agents in Medical Magnetic Resonance Imaging: John Wiley & Sons. 471; and Datta et al., 2009, Accounts Chem Res 42: 938-947).

Most clinical MRI CAs are paramagnetic T1-weighted CAs, which enhance MR signals to produce bright positive contrast such as gadolinium-($Gd3+$) ion-based T1 CAs. The recent discovery of nephrogenic systemic fibrosis (NSF) in some patients with severe renal disease or following liver transplant has generated concern leading to Food and Drug Administration (FDA) restrictions on clinical use of $Gd3+$-ion based ECF MRI CA (Girdhar, G. & Bluestein, D. Biological Effects of Dynamic Shear Stress in Cardiovascular Pathologies and Devices. Expert Rev. Afedical Devices 5, 167-181 (2008)).

Recently, the element manganese has received attention as a possible alternative to gadolinium. Manganese was reported early on as an example of paramagnetic contrast material for MRI. Unlike the lanthanides, it is a natural cellular constituent resembling $Ca2+$ and often functions as a regulatory cofactor for enzymes and receptors. Normal daily dietary requirement for manganese is 3-8 µmol while normal serum levels are 0.001 µmol/1. Manganese toxicity has only been reported following long-term exposure or at high concentrations resulting in neurological symptoms (Pan, D. et al. Revisiting an old friend: manganese-based MRI contrast agents. WIREs Nanomedicine and Nanobiotechnology 3, 162-173 (2010)).

Over the past 10 years, carbon nanostructures such as gadofullerenes (represented as $Gd@Ca_{60}$ $Gd@C_{80}$ and $Gd@C_{82}$) and gadonanotubes (represented as Gd @US-tubes, where US-tubes=ultra-short SWNTs) that encapsulate $Gd^{3+}$ metal ion have been proposed as $T_1$ CAs for MRI (Sitharaman, B. & Wilson, L. J. Gadofullerenes and Gadonanotubes: A new paradigm for high-performance magnetic resonance imaging contrast agent probes Journal of Biomedical Nanotechnology 3, 342-352 (2007)). The synthesis strategies in the development of these complexes have focused on covalently or non-covalently functionalizing multiple $Gd^{3+}$-chelate complexes onto the external carbon sheet of carbon nanostructures such as carbon nanotubes and nanodiamonds (Richard et al., 2008, Nano Letters 8: 232-236; and Manus et al., 2009, Nano Letters 10: 484-489), or encapsulation of $Gd^{3+}$-ions within the carbon sheet of carbon nanostructures such as fullerene (a.k.a. gadofullerenes) (Toth et al., 2005, J Am Chem Soc 127: 799-805; Kato et al., 2003, J Am Chem Soc 125: 4391-4397; and Fatouros et al., 2006, Radiology 240: 756-764), and single-walled carbon nanotubes (a.k.a. gadonanotubes) (Sitharaman et al., 2005, Chem Commun: 3915-3917; and Ananta et al., 2010, Nature nanotechnology 5: 815-821). These $Gd^{3+}$-ion carbon nanostructures show between two-fold to two-order increase in relaxivity (depending on the magnetic field) compared to $Gd^{3+}$-chelate complexes with the gadonanotubes showing the highest relaxivities at low to high (0.01-3T) magnetic fields. However, the potential and efficacy of $Mn^{2+}$-ion carbon nanostructure complexes as MRI CAs still has not been investigated.

The variable-magnetic field (O.Ol-3T) relaxivity or nuclear magnetic resonance dispersion (NMRD) profiles of the gadonanotubes are characteristically different than those obtained for any other MRI CA and their relaxation mechanisms are not well understood. A major reason for this lack of understanding is that unlike $Gd3+$ ion chelates, which can be prepared at a very high level of purity and unambiguously characterized, the carbon nanostructure-$Gd3+$ ion systems are rather complex mainly due to their particulate nature, and intricate relationships linking their chemical, geometric, and magnetic characteristics to their properties as MRI contrast agents. Nevertheless, geometric confinement of the $Gd3+$ ion within nanoporous structures maybe one reason (Ananta et al., 2010, Nature nanotechnology 5: 815-821; and Bresinska 1, 1994, J Phys Chem 98: 12989-12994). While confinement of the Gd3+ ions into nanoporous structures of silicon (Ananta et al., 2010, Nature nanotechnology 5: 815-821) or zeolites (Bresinska I, 1994, J Phys Chem 98: 12989-12994) increases the relaxivity by two or four times compared to Gd3+ chelate compounds, only when the Gd3+ ion are confined within single-walled carbon nanotubes (Sitharaman et al., 2005, Chem Commun: 3915-3917; and Ananta et al., 2010, Nature nanotechnology 5: 815-821) has there been an order of magnitude or more increase in relaxivity (irrespective of the magnetic field strength) with NMRD profiles significantly different that those reported for other Gd3+ ion-based complexes. Additionally, to date, there have been no studies performed to systematically investigate whether the high increase in relaxivity and unconventional NMRD profiles are unique to paramagnetic ions confined in single-walled carbon nanotubes, which are seamless cylinders formed from a graphene sheet, or in general observed for paramagnetic ions confined in other graphene or graphitic structures.

Graphene, a two-dimensional (2-D) nanostructure of carbon, has attracted a great deal of attention showing potential for various material and biomedical science applications (Novoselov, K. S. et al. Electric field effect in atomically thin carbon films. *Science* 306, 666 (2004)). Theoretical studies predict a variety of magnetic phenomena in graphene (Makarova, 2004, Semiconductors 38: 615-638), and to date, few of these effects have been explored experimentally (Wang, et al., 2008, Nano Letters 9: 220-224). Recently, simple potassium permanganate ($KMnO_4$)-based oxidative chemical procedures have been used in the large scale production of graphite oxide, graphene nanoplatelets, and graphene nanoribbons using starting materials such as graphite and MWCNTs (Stankovich, et al., 2007, Carbon 45: 1558-1565; and Kosynkin, et al., 2009, Nature 458: 872-876). In this work, experimental studies were performed to characterize the physico-chemical properties of graphite oxide, graphene nanoplatelets, and graphene nanoribbons synthesized using these techniques. We demonstrate that trace amounts of $Mn^{2+}$ ions get confined (intercalated) within the graphene sheets during the synthesis process, and that this confinement in general substantially increases the relaxivity (up to 2 order) compared to paramagnetic chelate compounds, and these materials show diverse structural, chemical and magnetic properties with NMRD profiles different than those of the paramagnetic chelates.

Recent reports have shown that affordable large scale production of graphene nanoplatelets (GNPs) and graphene nanoribbons (GNRs) is possible by using chemical techniques (Stankovich, S. et al. Stable aqueous dispersions of graphitic nanoplatelets via the reduction of exfoliated graphite oxide in the presence of poly (sodium 4-styrenesulfonate). *Journal of Materials Chemistry* 16, 155-158 (2006); Stankovich, S. et al. Synthesis of graphene-based nanosheets via chemical reduction of exfoliated graphite oxide. *Carbon* 45, 1558-1565 (2007); Stankovich, S., Piner, R., Nguyen, S. & Ruoff, R. Synthesis and exfoliation of isocyanate-treated graphene oxide nanoplatelets. *Carbon* 44, 3342-3347 (2006); Li, D., Müller, M., Gilje, S., Kaner, R. & Wallace, G. Processable aqueous dispersions of graphene nanosheets. *Nature nanotechnology* 3, 101-105 (2008); Kosynkin, D. et al. Longitudinal unzipping of carbon nanotubes to form graphene nanoribbons. *Nature* 458, 872-876 (2009); Higginbotham, A., Kosynkin, D., Sinitskii, A., Sun, Z. & Tour, J. Lower-Defect Graphene Oxide Nanoribbons from Multi-walled Carbon Nanotubes. *ACS nano* 4, 2059-2069 (2010); Geng, Y., Wang, S. & Kim, J. Preparation of graphite nanoplatelets and graphene sheets. *Journal of colloid and interface science* 336, 592-598 (2009)).

SUMMARY OF THE INVENTION

The present invention provides a magnetic composition comprising one or more magnetic metals and a graphene-like nanostructure or graphitic nano- or microstructure.

Preferably, the magnetic composition of the invention exhibits a relaxivity r1 of at least about 3, 5, 10, 20, 30, 40, 50, 100 or 500 $mM^{-1}s^{-1}$.

Preferably, the magnetic composition of the invention exhibits a relaxivity r2 of at least about 3, 5, 10, 20, 30, 40, 50, 500, or 1000 $mM^{-1}s^{-1}$.

The graphene-like nanostructure can be a carbon nanoplatelet or a carbon nanoribbon. The carbon nanoplatelet or carbon nanoribbon can be oxidized. Preferably, the graphene-like nanostructure, e.g., the carbon nanoplatelet or the carbon nanoribbon, has a thickness of about 20 nm or less, 15 nm or less, 10 nm or less, 5 nm or less, 3 nm or less, at least 2 atomic carbon sheets, at least 5 atomic carbon sheets, or at least 10 atomic carbon sheets.

Preferably, the graphitic nanostructure or microstructure has a thickness of 5 μm or less, 4 μm or less, 3 μm or less, 2 μm or less, 1 μm or less, 500 nm or less, 250 nm or less of 100 nm or less.

Preferably, the carbon nanoplatelet having an average diameter in the range of 5 to 100 nm, 10 to 75 nm, 20 to 50 nm, or 30 to 40 nm. Preferably, the carbon nanoribbon having an average width in the range of 1 to 250 nm, 10 to 200 nm, 50 to 150 nm, or 70 to 100 nm.

The graphene-like nanostructure or graphitic nano- or microstructure can further comprise a water solubilizing moiety attached to the graphene-like nanostructure or microstructure, e.g., covalently attached to the graphene-like nanostructure or graphitic nano- or microstructure.

In one embodiment, the magnetic metal is a room temperature paramagnetic metallic element, including but not limited to Mn. In another embodiment, the magnetic metal is a room temperature ferromagnetic metallic element including but not limited to Fe, Co, and Ni. In still another embodiment, the magnetic metal is a rare earth metal, including but not limited to Gd, Eu, Pr, Nd, and Sm. Preferred magnetic metals that can be used in the present invention include Mn, Gd, and Fe.

The magnetic composition can comprise more than one magnetic metal. In one embodiment, the magnetic composition comprises two different magnetic metals.

The magnetic metal can be present in the magnetic composition as an ion. The magnetic metal can also be present in the magnetic composition in the form of a metal compound, including but not limited to a metal oxide and a metal salt. The magnetic metal or compound thereof can be intercalated in the graphene-like nanostructure or graphitic nano- or microstructure.

The magnetic composition of the present invention can comprise the magnetic metal in an amount in the range of 1 ppb (mass parts per billion) to $10^7$ ppm (mass parts per million), $10^2$ ppb to 106 ppm, 1 ppm to $10^5$ ppm, 10 to $10^4$ ppm, or $10^2$ to $10^3$ ppm.

The present invention also provides a method of performing magnetic resonance imaging of a subject, comprising administering to the subject a sufficient amount of the magnetic composition of the invention; and imaging the subject using a magnetic resonance imaging device. The subject can be any animal, including but not limited to a mammal, e.g., a human.

The present invention also provides a composition for MRI imaging, comprising a sufficient amount of the magnetic composition, and one or more physiologically acceptable carriers or excipients.

The present invention also provides a method of producing a magnetic composition comprising a magnetic metal and a graphene-like carbon nanostructure. The method comprises oxidizing graphite with a mixture of sulfuric acid $H_2SO_4$, sodium nitrate $NaNO_3$, and potassium permanganate $KMnO_4$; and sonicating a suspension of the product obtained in the previous step. The method can further comprise a step of reducing the magnetic composition with a reducing agent.

The present invention also provides a method of producing a magnetic composition comprising a magnetic metal and a graphene-like carbon nanostructure. The method comprises treating a multi-walled carbon nanotube with sulfuric acid $H_2SO_4$, nitric acid ($HNO_3$), manganese chloride ($MnCl_2$), and potassium permanganate $KMnO_4$. In one embodiment, the treatment is carried out by a method comprising suspending said multi-walled carbon nanotube in concentrated $H_2SO_4$, nitric acid (HNO3); adding manganese chloride ($MnCl_2$), $KMnO_4$; heating the mixture and sonicating a suspension of the product obtained in the previous step. In a specific embodiment, the mixture is heated to 55-70° C.

The magnetic composition can further be water solubilized using a method known in the art, e.g., (1) using a synthesis protocol similar to a cycloaddition reaction used to add carboxylic acid functionalities across carbon-carbon double bonds of fullerenes and metallofullerenes. (2) Covalently or non-covalently functionalizing with nature polymers such as dextran or synthetic amphiphilic polymers such as poly ethylene glycol.

DETAILED DESCRIPTION OF THE INVENTION

Figure 1A:
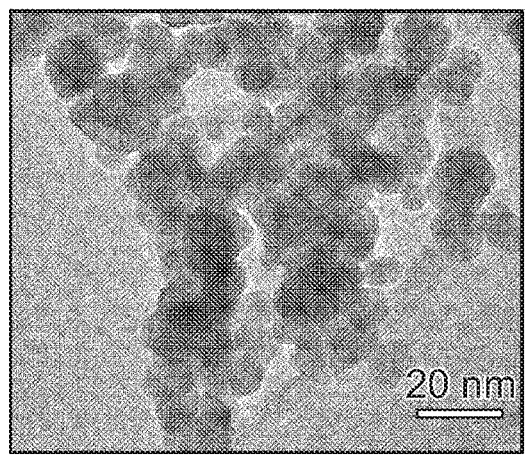
FIGS. 1(a)-1(d). TEM images at 200 kV for manganese intercalated graphene nanoplatelets and nanoribbons (a) Showing ~20 nm wide few layered and multilayered reduced graphene nanoplatelets; (b) HR TEM image showing lattice structure of carbon atoms on reduced graphene nanoplatelets (c) Images revealing ~120 nm width and ~0.6-2 μm length graphene nanoribbon structure; (d) High magnification image revealing multiple layers of graphene nanoribbon sheets (Indicated by arrows).
Figure 1B:
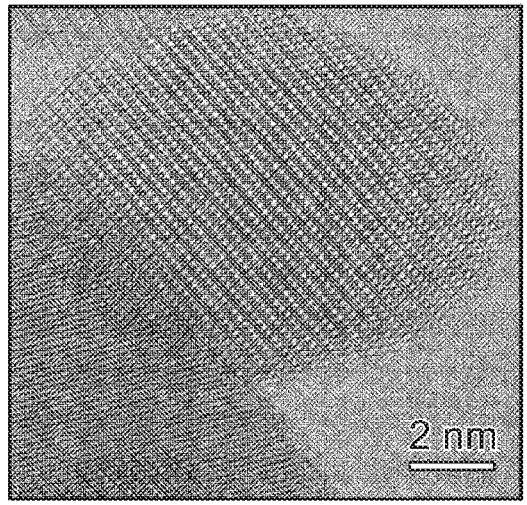
Figure 1C:
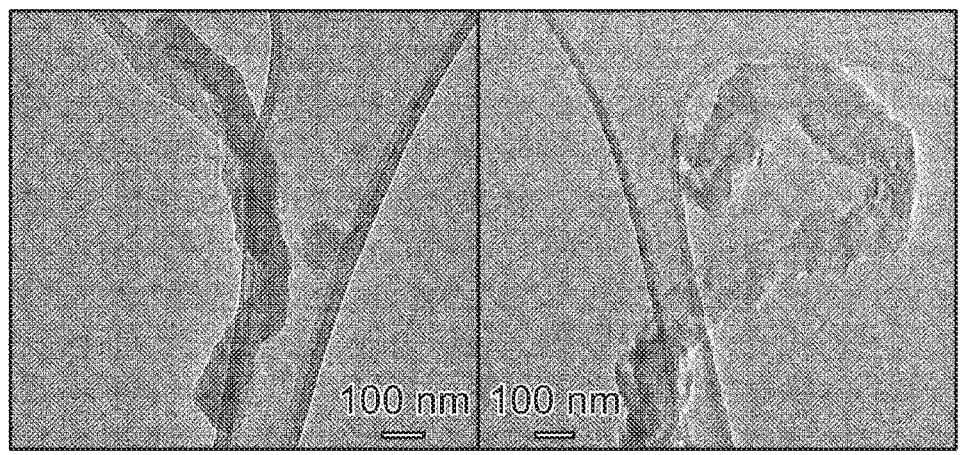
Figure 1D:
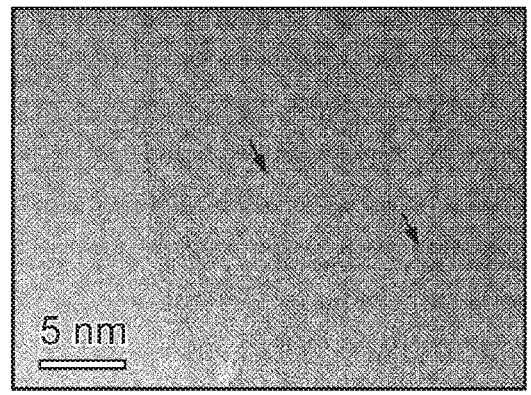

The present invention provides a magnetic composition comprising one or more magnetic metals and a graphene-like nanostructure or graphitic nano- or microstructure. The magnetic composition can be paramagnetic or diamagnetic. Preferably, the magnetic composition is paramagnetic. The magnetic composition can be ferromagnetic. The magnetic composition can also be superparamagnetic.

Preferably, the magnetic composition of the invention exhibits a relaxivity r1 of at least about 3, 5, 10, 20, 30, 40, 50, 60, 70, 80, 100 or 500 $mM^{-1}s^{-1}$. In a specific embodiment, the magnetic composition of the invention exhibits a relaxivity r1 of about 45 $mM^{-1}s^{-1}$. In another specific embodiment, the magnetic composition of the invention exhibits a relaxivity r1 of about 73 $mM^{-1}s^{-1}$.

Preferably, the magnetic composition of the invention exhibits a relaxivity r2 of at least about 3, 5, 10, 20, 30, 40, 50, 100, 200, 300, 400, 500, or 1000 $mM^{-1}s^{-1}$. In a specific embodiment, the magnetic composition of the invention exhibits a relaxivity r2 of about 15 $mM^{-1}s^{-1}$. In another specific embodiment, the magnetic composition of the invention exhibits a relaxivity r2 of about 251 $mM^{-1}s^{-1}$.

Graphene is a flat monolayer of carbon atoms tightly packed into a two-dimensional (2D) honeycomb lattice, and is a basic building block for graphitic materials of all other dimensionalities, and which can be wrapped up into 0D fullerenes, rolled into 1D nanotubes or stacked into 3D graphite (Geim and Novoselov, 2007, "The rise of graphene", *Nature Materials* 6 (3): 183-191). As used herein, the term "graphene-like nanostructure" (or "graphene-like nanoparticle") refers to a carbon nanostructure comprising one or more atomic carbon sheets or layers. In the present application, for simplicity reasons, the term "graphene nanostructure" is also used to refer to a graphene-like nanostructure. Thus, unless expressly stated, the term "graphene nanostructure" is not limited to a nanostructure having only a single atomic carbon sheet. The graphene-like nanostructure can be a carbon nanoplatelet or a carbon nanoribbon. The carbon nanoplatelet or carbon nanoribbon can be oxidized.

Preferably, the graphitic nanostructure or microstructure has a thickness of 5 μm or less, 4 μm or less, 3 μm or less, 2 μm or less, 1 μm or less, 500 nm or less, 250 nm or less of 100 nm or less.

In one embodiment, the graphitic microstructure has a thickness in the range of 1 to 5 μm, 2 to 4 μm, or 2 to 3 μm. In another embodiment, the graphitic microstructure has a longest length of the structure in the range of 1 to 5 μm, 2 to 4 μm, or 2 to 3 μm.

Preferably, the graphene-like nanostructure, e.g., the carbon nanoplatelet or the carbon nanoribbon, has a thickness of about 20 nm or less, 15 nm or less, 10 nm or less, 5 nm or less or 3 nm or less. The graphene-like nanostructure, e.g., the carbon nanoplatelet or the carbon nanoribbon, can comprise at least 1 atomic carbon sheet, at least 2 atomic carbon sheets, at least 5 atomic carbon sheets, or at least 10 atomic carbon sheets. In one embodiment, the graphene-like nanostructure, e.g., the carbon nanoplatelet or the carbon nanoribbon, comprises 1 to 12 atomic carbon sheets. In a specific embodiment, the graphene-like nanostructure, e.g., the carbon nanoplatelet or the carbon nanoribbon, comprises 1 or 2 atomic carbon sheets.

Preferably, the graphene-like nanostructure is a carbon nanoplatelet having an average diameter in the range of 5 to 100 nm, 10 to 75 nm, 20 to 50 nm, or 30 to 40 nm. In a specific embodiment, the carbon nanoplatelet has an average diameter of about 20 nm. In another specific embodiment, the carbon nanoplatelet has an average diameter of about 50 nm. In still another specific embodiment, the graphene-like nanoplatelet has a thickness in the range of 1 to 5 nm and a diameter of about 50 nm.

Preferably, the graphene-like nanostructure is a carbon nanoribbon having an average width in the range of 1 to 250 nm, 10 to 200 nm, 50 to 150 nm, or 70 to 100 nm. In a specific embodiment, the carbon nanoribbon has an average width of about 120 nm. Preferably, the carbon nanoribbon has an average length in the range of 200 to 5000 nm, 400 to 4000 nm, or 500 to 3000 nm. In a specific embodiment, the carbon nanoribbon has an average length in the range of 600 to 2000 nm.

The graphene-like nanostructure or graphitic nano- or microstructure can further comprise a water solubilizing moiety attached to the graphene-like nanostructure or microstructure. In one embodiment, the water solubilizing moiety is covalently attached to the graphene-like nanostructure or graphitic nano- or microstructure. In a specific embodiment, the water solubilizing moiety is selected from the group consisting of malonic acid and serinol malonodiamide attached to the graphene-like nanostructure or graphitic nano- or microstructure. The water solubilizing moiety can be attached to the graphene-like nanostructure or graphitic nano- or microstructure using any method known in the art, e.g., using Bingel type reactions (Bingel, C., 1993, Cyclopropanierung von Fullerenen, Chemische Berichte 126 (8): 1957). In another specific embodiment, the water solubilizing moiety is a natural polymer dextran or synthetic polymer polyethylene glycol. The water solubilizing moiety can covalently or non-covalently attached using any method known in the art, e.g., using sonication for 1-3 hours at elevated temperatures (60-95° C.).

The magnetic metal in the magnetic composition of the present invention can be any metal that exhibits magnetism in the presence or absence of an externally applied magnetic field. In one embodiment, the magnetic metal is a room temperature paramagnetic metallic element, including but not limited to Mn. In another embodiment, the magnetic metal is a room temperature ferromagnetic metallic element including but not limited to Fe, Co, and Ni. In still another embodiment, the magnetic metal is a rare earth metal, including but not limited to Gd, Eu, Pr, Nd, and Sm. Preferred magnetic metals that can be used in the present invention include Mn, Gd, and Fe.

The magnetic composition can comprise more than one magnetic metal. In one embodiment, the magnetic composition comprises two different magnetic metals. In a preferred embodiment, the magnetic composition comprises Mn and Fe.

The magnetic metal can be present in the magnetic composition as an ion. The magnetic metal can also be present in the magnetic composition in the form of a metal compound, including but not limited to a metal oxide and a metal salt. In a preferred embodiment, the magnetic metal is present in the magnetic composition in the form of a metal oxide.

In a preferred embodiment, the magnetic metal or compound thereof is intercalated in the graphene-like nanostructure or graphitic nano- or microstructure.

The magnetic composition of the present invention can comprise the magnetic metal in an amount in the range of 1 ppb (mass parts per billion) to $10^7$ ppm (mass parts per million), $10^2$ ppb to $10^6$ ppm, $10^2$ ppb to $10^2$ ppm, 1 ppm to $10^5$ ppm, 10 to $10^4$ ppm, or $10^2$ to $10^3$ ppm.

In particularly preferred embodiments, the magnetic composition of the present invention comprises a graphene-like nanostructure as described herein and Mn. In one embodiment, the Mn is present as a Mn oxide. In another embodiment, the Mn is present as di-valent and/or tri-valent Mn. In still another embodiment, the Mn oxide comprises hausmannite.

In one embodiment, the magnetic composition comprises a carbon nanoplatelet and Mn in an amount in the range of $10^6$ to $5.5 \times 10^7$ ppm, e.g., about $5 \times 10^6$ ppm.

In another embodiment, the magnetic composition comprises a carbon nanoribbon and Mn in an amount in the range of $10^2$ to $10^3$ ppm, e.g., $5 \times 10^2$ ppm. In still another embodiment, the Mn is in an amount in the range of 0.1 to 2 ppm, 0.2 to 1.5 ppm, or 0.5 to 1 ppm.

The present invention also provides a method of performing magnetic resonance imaging of a subject, comprising administering to the subject a sufficient amount of the magnetic composition of the invention; and imaging the subject using a magnetic resonance imaging device. The subject can be any animal, including but not limited to a mammal. In a preferred embodiment, the subject is a human. The magnetic composition of the invention can be used alone or in combination with another agent, including but not limited to another MRI contrast agent. The magnetic composition can be administrated to the subject by any method known in the art, including but not limited to intravascular injection and oral administration. A person skilled in the art would be able to select the appropriate administration route according to the tissue, organ or other region in the body of interest and/or the purposes of the scan. Magnetic resonance imaging can be carried by any standard method and device known in the art. The magnetic composition of the invention and/or another MRI CA can be in any suitable form of imaging agents, including but not limited to extracellular fluid or first pass MRI CAs, blood pool MRI CAs, organ specific MRI CAs, and molecular imaging MRI CAs.

The invention also provides a kit for use in MRI imaging, comprising in one or more containers a sufficient amount of one or more magnetic compositions. A sufficient amount of the magnetic composition refers to that amount of the composition sufficient to result in enhancement of image contrast in a MRI image. The magnetic composition can be in any suitable form of imaging agent, including but not limited to extracellular fluid or first pass MRI CAs, blood pool MRI CAs, organ specific MRI CAs, and molecular imaging MRI CAs.

Toxicity of the magnetic composition can be determined by standard procedures in cell cultures and/or experimental animals, e.g., for determining the $LD_{50}$ (the dose lethal to 50% of the population). The effective dose can be estimated according to clinically accepted standard. The data obtained from the cell culture assays and/or animal studies can be used in formulating a range of dosage for use in humans. The dosage of such magnetic compositions is preferably within a range of concentrations that are effective in enhancing MRI images with little or no toxicity. The dosage may vary within this range depending upon the dosage form employed and the route of administration utilized. A person skilled in the art would be able to select the suitable dosage of the magnetic composition based on standard protocols.

The compositions for use in accordance with the present invention may be formulated in conventional manner using one or more physiologically acceptable carriers or excipients depending on, e.g., the route for administration, e.g., oral or parenteral administration.

For oral administration, the magnetic compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

The compounds may be formulated for parenteral administration by injection, e.g., by bolus injection or continuous infusion. Formulations for injection may be presented in unit dosage form, e.g., in ampoules or in multi-dose containers. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

Suitable routes of administration may, for example, include oral and parenteral delivery, including intramuscular, subcutaneous, intramedullary injections, as well as intrathecal, direct intraventricular, intravenous, intraperitoneal, intranasal, or intraocular injections.

Furthermore, one may administer the drug in a targeted drug delivery system, for example, in a liposome coated with an antibody specific for affected cells. The liposomes will be targeted to and taken up selectively by the cells of interest.

The compositions may, if desired, be presented in a pack or dispenser device which may contain one or more unit dosage forms containing the magnetic composition. The pack or dispenser device may be accompanied by instructions for administration. Compositions comprising a magnetic composition of the invention formulated in a compatible carrier may also be prepared, placed in an appropriate container, and labeled for use.

Thus, the present invention also provides the magnetic composition of the present invention for use in magnetic resonance imaging of the subject.

The present invention also provides a method of producing a magnetic composition comprising a magnetic metal and a graphene-like carbon nanostructure. The method comprises oxidizing graphite with a mixture of sulfuric acid $H_2SO_4$, sodium nitrate $NaNO_3$, and potassium permanganate $KMnO_4$; and sonicating a suspension of the product obtained in the previous step. The method can further comprise a step of reducing the magnetic composition with a reducing agent. In one embodiment, the reducing agent is hydrazine hydrate. In one embodiment, the graphite used in the method of the invention is micro-graphite, e.g., having a size of about 45 μm.

The present invention also provides a method of producing a magnetic composition comprising a magnetic metal and a graphene-like carbon nanostructure. The method comprises treating a multi-walled carbon nanotube with sulfuric acid $H_2SO_4$ and potassium permanganate $KMnO_4$. In one embodiment, the treatment is carried out by a method comprising suspending said multi-walled carbon nanotube in concentrated $H_2SO_4$; adding $KMnO_4$; and heating the mixture. In a specific embodiment, the mixture is heated to 55-70° C.

The magnetic composition can be water solubilized using a method known in the art. In one embodiment, the magnetic composition is water solubilized using a synthesis protocol similar to a cycloaddition reaction used to add carboxylic acid functionalities across carbon-carbon double bonds of fullerenes and metallofullerenes (Sithamaran, B.; Zakharian, T. Y. et al. *Molecular Pharmaceutics* 2008, 5, 567).

EXAMPLES

The following examples are presented by way of illustration of the present invention, and are not intended to limit the present invention in any way.

Example 1

Materials and Methods:

Graphene Nanoplatelet (GNP) Synthesis:

Oxidized graphite was prepared from analytical grade micro-graphite (45 μm, 496596-Sigma Aldrich) by modified Hummer's method (Geng, Y., Wang, S. & Kim, J. Preparation of graphite nanoplatelets and graphene sheets. *Journal of colloid and interface science* 336, 592-598 (2009); Hummers Jr, W. & Offeman, R. Preparation of graphitic oxide. *Journal of the American Chemical Society* 80, 1339-1339 (1958)). In a typical exfoliation procedure, dried oxidized graphite (200 mg) was suspended in a round bottom flask containing water (200 ml) and sonicated for 1 h in an ultrasonic bath cleaner (Fischer Scientific, FS60, 230W) (Stankovich, S. et al. Synthesis of graphene-based nanosheets via chemical reduction of exfoliated graphite oxide. *Carbon* 45, 1558-1565 (2007)). 50 ml of this uniform solution was centrifuged and pellet was dried overnight to obtain oxidized graphene nanoplatelets (GNPs). The remaining 150 ml was treated with hydrazine hydrate (1.5 ml, 37.1 mmol) and heated in an oil bath at 100° C. under a water cooled condenser for 12 h, resulting in a black precipitate. The product was isolated and washed over a medium sintered glass filter funnel with water (500 ml) and methanol (500 ml) and dried by continuous air flow to yield reduced graphene nanoplatelets.

Graphene Nanoribbon (GNR) Synthesis:

Graphene nanoribbons were prepared from MWCNTs (636843-Sigma Aldrich) in a procedure similar to the one previously described (Kosynkin, D. et al. Longitudinal unzipping of carbon nanotubes to form graphene nanoribbons. *Nature* 458, 872-876 (2009); Higginbotham, A., Kosynkin, D., Sinitskii, A., Sun, Z. & Tour, J. Lower-Defect Graphene Oxide Nanoribbons from Multiwalled Carbon Nanotubes. *ACS nano* 4, 2059-2069 (2010)). MWCNTs (150 mg, 12.5 mequiv of carbon) were suspended in 30 ml of conc. $H_2SO_4$ for 2 h. $KMnO_4$ (750 mg, 4.75 mmol) was added and the mixture was allowed to stir for 1 h. The reaction was then heated in an oil bath at 55-70° C. for an additional 1 h, until completion. It was cooled to room temperature and the product was washed with acidic water, ethanol and ether, and isolated by subsequent centrifugation. Centrifugation results in simple, easy and quick isolation with 100% yield.

Sample Analysis:

High Resolution Transmission Electron Microscopy (TEM) imaging analysis was performed on the GNP and GNR samples using a JEOL JEM2010F (FEG-TEM) High Resolution Analytical Transmission Electron Microscope. Imaging was carried out at 200 kV accelerating voltage. TEM samples were prepared by dispersing the dry powders in 1:1 ethanol: water to form a homogeneous mixture. The suspension was then deposited on to a 300 mesh Cu grid covered with a lacey carbon film (EMS, Cat # LC305-Cu). RAMAN spectral analysis of graphite, oxidized graphite, and all graphene samples was performed between 200 to 3000 $cm^{-1}$ using a Thermo Scientific DXR Raman confocal microscope at 530 nm diode laser excitation wavelength and room temperature.

Characterization of Magnetic Behavior:

Magnetization of graphene samples was studied using a super conducting quantum interference device (SQUID) magnetometer with a sensitivity of about $10^{-8}$ emu. The samples were carefully weighed and loaded in gelatin capsules. Samples were analyzed between the applied magnetic field range of −50000 Oe to 50000 Oe between 0 and 300K. In the Field cooling and Zero Field cooling mode, a coercive field of 500 Oe was applied for studying magnetization as a function of temperature.

Characterization of Relaxivity:

For relaxivity measurements, 1 mg of all graphene nanoplatelets and graphene nanoribbon samples were dispersed uniformly in 2 ml of biologically compatible 1% Pluronic F127 surfactant solution. The supernatants of these saturated (suspensions) solutions were then used for relaxometry measurements. The longitudinal and transverse relaxation times ($T_1$, $T_2$) were measured using iSpin-NMR system (Spincore technology) at a proton NMR frequency of 21.42 MHz and 0.5T field strength. $T_1$ and $T_2$ were measured using inversion recovery and CPMG methods respectively. The inverse of the relaxation times represent the respective relaxation rates, $R_1$ and $R_2$. Relaxivity ($r_{1,2}$), which is a measure of the efficacy of an MRI contrast agent is expressed as a function of its concentration. It was calculated using the formula $r_{1,2}=(R_{1,2}-R_0)/[Mn^{2+}]$; $R_{1,2}$ and $R_0$ are the longitudinal or transverse relaxation rates of the samples and 1% Pluronic F127 surfactant solution respectively, and $[Mn^{2+}]$ is the concentration of Manganese in the volume of solution used for relaxation measurements.

Metal Content Analysis:

To confirm the presence and to determine the concentration of manganese in our samples, inductively coupled plasma optical emission spectroscopy (ICPOES) was carried out separately at two commercial analytical testing laboratories (Columbia Analytical Services, Tucson, Ariz. and Galbraith Laboratories, Inc., Knoxville, Tenn.). The potassium [K] content was also estimated in all samples. For the ICP sample preparation, the suspensions of the samples in Pluronic solutions used for relaxation time measurements were treated with conc. $HNO_3$ and carefully heated to obtain a solid residue. They were then further treated with 30% $H_2O_2$ and heated again to eliminate carbonaceous material. In case of the solid samples, they were directly subjected to peroxide and heat treatment to remove the carbonaceous content. The remaining residue, in each case, was dissolved in 2% $HNO_3$ and analyzed by ICP using a Thermo Jarrell Ash ICAP 61 Inductively Coupled Plasma Spectrometer.

In Vitro Phantom MRI:

In vitro T and $T_2$ MRI phantom experiments were performed on the nanoribbon samples using a 3T Trio Siemens MRI system and the images were obtained using 2D spin-echo imaging with a repetition time (TR) of 500 ms and echo times (TE) of 10 ms for $T_1$ and TR of 8000 ms and TE of 112 ms for $T_2$ measurements.

Results and Discussion:

This Example shows that the simple chemical oxidation procedures (see methods and materials section for synthesis details) using starting materials such as graphite and MWCNTs yield magnetic manganese intercalated graphene nanoplatelets and graphene nanoribbons which show potential as MRI contrast agents.

Figure 7:
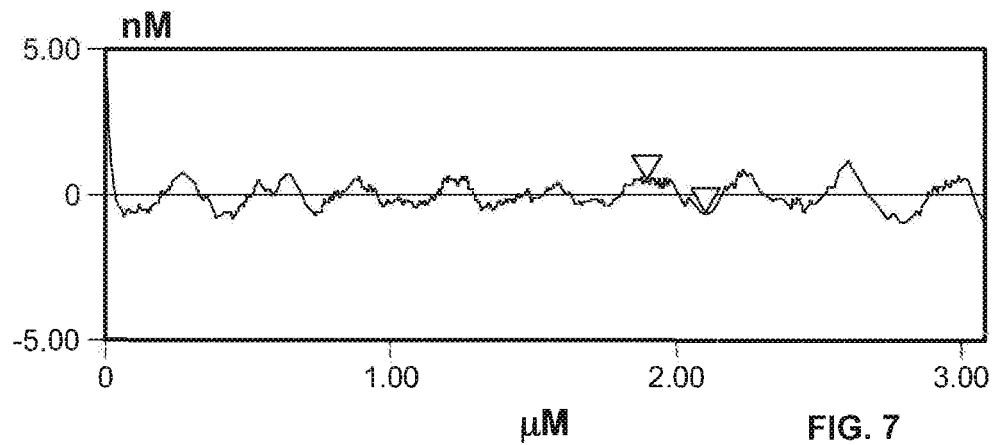
FIG. 7. AFM section analysis of graphene nanoplatelets dispersed on a silicon substrate, showing a uniform thickness of ~1.137 nm.

FIG. 1(a, b) show representative low and high magnification TEM images of reduced graphene nanoplatelets, respectively, which provides their structural and morphological information. As seen in FIG. 1(a), they appear to be round in shape with an average width of ~20 nm. Some platelets appear darker than the others and this is due to the presence of multi-layered graphene oxide sheets. The lighter ones, which are almost transparent, are single or double layered graphene oxide sheets. FIG. 1(b) reveals the atomic lattice fringe structure of the individual graphene sheets where the lattice grid lines and hexagonal carbon atom rings are clearly visible (Lu, G., Mao, S., Park, S., Ruoff, R. & Chen, J. Facile, noncovalent decoration of graphene oxide sheets with nanocrystals. *Nano Research* 2, 192-200 (2009)). AFM section analysis of the graphene oxide nanoplatelets dispersion on a Si substrate revealed a uniform thickness of ~1.137 nm (FIG. 7). Pristine graphene sheets have an atomic layer thickness (Van der Waals) of 0.34 nm. The presence of covalent bonds with carboxyl and hydroxyl groups and displacement of $sp^3$ carbon atoms in the graphene oxide nanoplatelet structure is known to be the reason for an increase in the thickness (Stankovich, S. et al. Synthesis of graphene-based nanosheets via chemical reduction of exfoliated graphite oxide. *Carbon* 45, 1558-1565 (2007)).

FIG. 1(c,d) show representative low and high magnification TEM images of graphene nanoribbons, respectively. As seen in FIG. 1(c), the graphene nanoribbons have fully unzipped layers of graphene sheets. The high resolution TEM image in FIG. 1(d) clearly shows that the nanoribbons are multilayered (arrows) due to successive unzipping of the concentric walls of MWCNTs. The atomic structural surface quality of the graphene oxide nanoribbons appears mostly uniform and smooth, with few defects. The starting material, MWCNTs, have an outer diameter of 40-70 nm and length of 500-2000 nm. Since the MWCNTs are cylinders, upon unzipping, they should open up completely to have breadths in the range of pi times the diameter, which is 125-220 nm and a length of 500-2000 nm. The analysis of the TEM images shows that the average width of the graphene nanoribbons is ~120 nm which is greater than the outer diameter of the outermost tubes of MWCNTs of 70 nm, thus, verifying the process of unzipping. This average value, however, is slightly lesser than the range required for fully flat ribbons, 125-220 nm and this can be substantiated by the fact that the unzipping process does not render fully flat ribbons, however, the ribbons still retain some curvature of the tubes and hence they have lesser breadths than that expected for fully flat sheets. The TEM images show an average length of ~600-2000 nm which falls within the calculated range for unzipped MWCNTs.

Figure 2A:
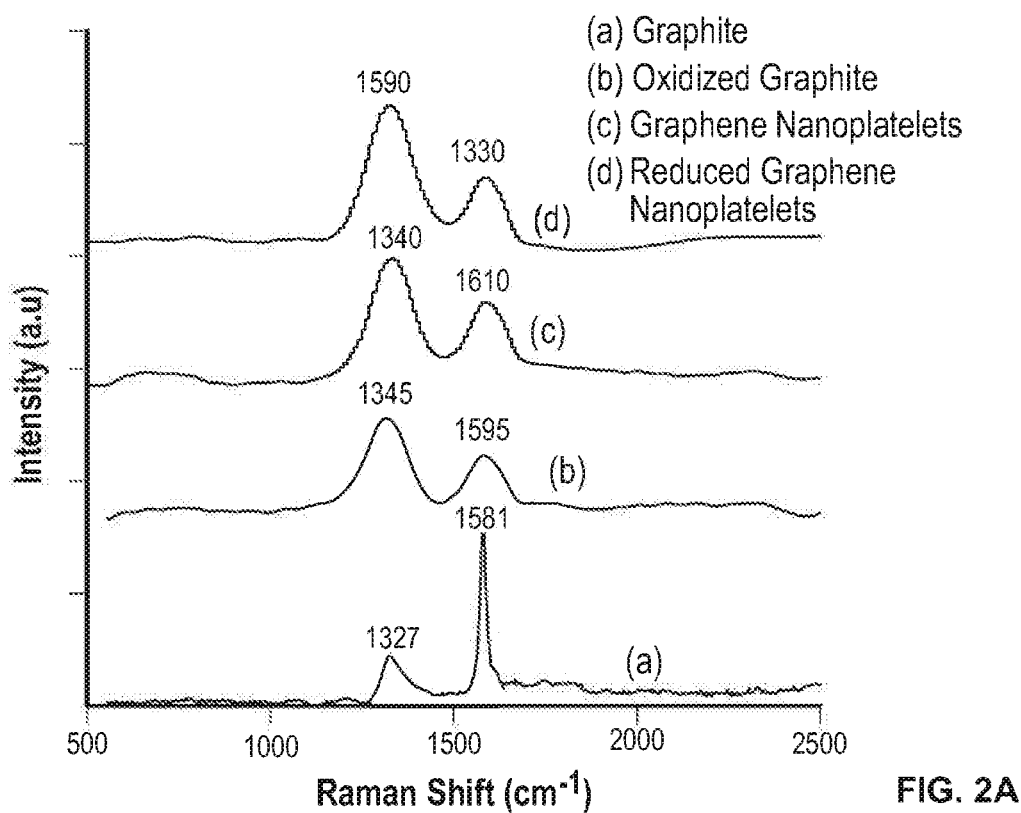
FIGS. 2(a)-2(b). Raman spectrum using 530 nm laser (a) Revealing D and G bands and corresponding peaks for graphite, oxidized graphite, graphene nanoplatelets and reduced graphene nanoplatelets; (b) Revealing D and G bands for MWCNTs and graphene nanoribbons.

FIG. 2(a) shows the Raman spectra of oxidized and reduced graphene nanoplatelets. Also included as controls are the Raman spectra of graphite and oxidized graphite. The spectrum of graphite shows a prominent sharp peak at 1581 $cm^{-1}$ indicating the G-band which is attributed to the doubly degenerate zone center $E_{2_g}$ mode (Tuinstra, F. & Koenig, J. Raman spectrum of graphite. *The Journal of Chemical Physics* 53, 1126 (1970)). In case of oxidized graphite, there is a broadening of the G band and a peak shift to 1595 $cm^{-1}$. Further, zone boundary phonons give rise to the D band at 1345 $cm^{-1}$, which becomes prominent indicating increase in the disorder $sp^2$ domains and reduction of crystal size due to oxidation. Due to the process of oxidation of graphite, there is an increase in the ratio of intensity of the D to G peaks ($I_D/I_G$), from 0.407 for graphite to 1.2 for oxidized graphite (Tuinstra, F. & Koenig, J. Raman spectrum of graphite. *The Journal of Chemical Physics* 53, 1126 (1970)). The spectra of oxidized graphene nanoplatelets and reduced graphene nanoplatelets show a further increase in $I_D/I_G$ to 1.3 and 1.44, respectively. FIG. 2(a) shows that in case of reduced graphene nanoplatelets, the peaks of D and G bands are being shifted closer to the values of graphite (1330 $cm^{-1}$ and 1590 $cm^{-1}$ respectively), which is attributed to the removal of the oxygen functionalities during reduction and restoration of order to an extent. However, the increase in $I_D/I_G$ to 1.44 is due to the reduction of the average size of $sp^2$ domains in addition to an increase in the number of such small sized disorder domains (Kosynkin, D. et al. Longitudinal unzipping of carbon nanotubes to form graphene nanoribbons. *Nature* 458, 872-876 (2009)).

Figure 8:
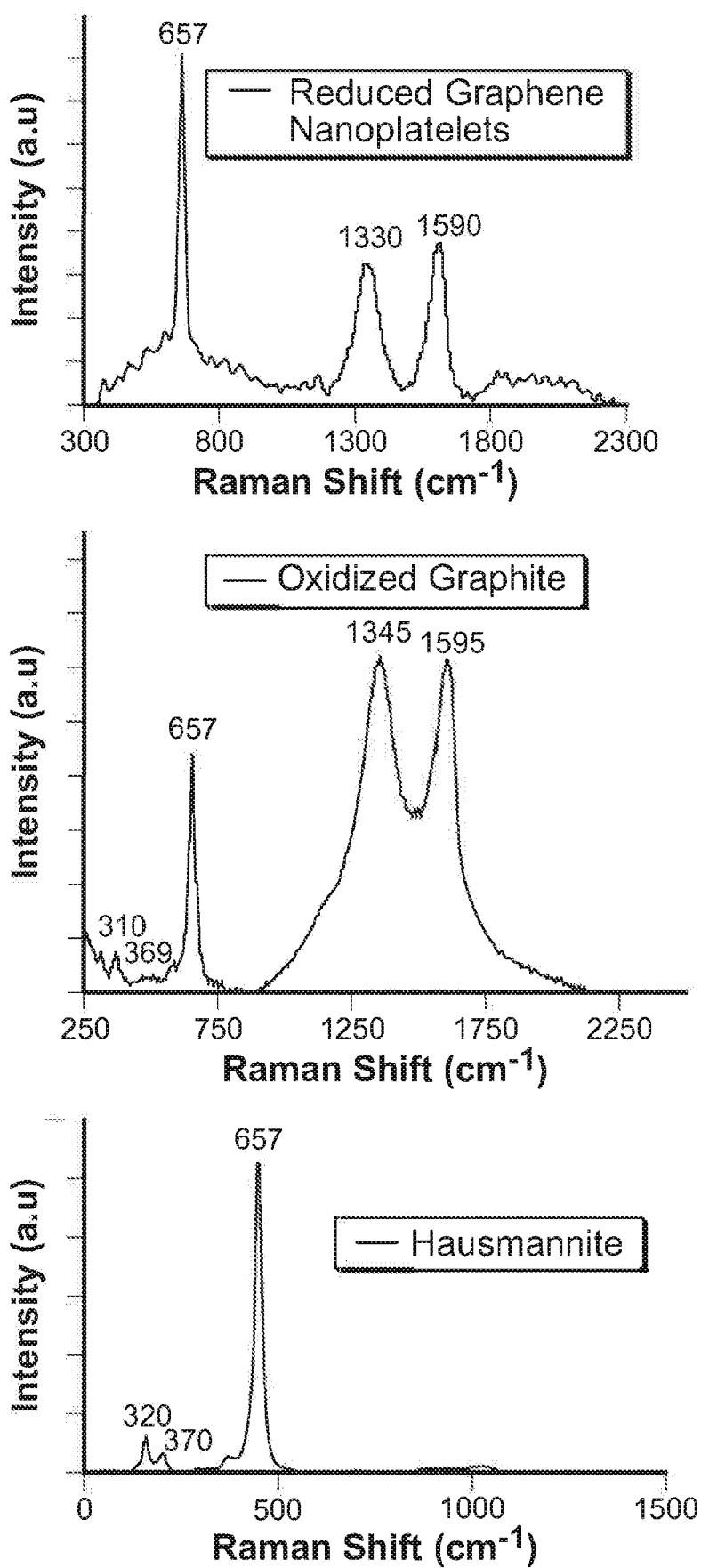
FIG. 8. Comparison of Raman spectra of Hausmannite ($Mn_3O_4$), oxidized graphite and reduced graphene nanoplatelets at 532 nm showing spectral peaks at 657, 370 and 320 $cm^{-1}$.

Additionally, the Raman spectra of oxidized graphite and reduced graphene nanoplatelets also showed additional peaks at around 657 $cm^{-1}$, 370 $cm^{-1}$ and 320 $cm^{-1}$ (FIG. 8). In order to identify the peaks, a Raman spectral database search using the RRUFF™ Project collection was performed. This confirmed that the peaks observed are due to a complex oxide containing di-valent and tri-valent manganese, known as Hausmannite, see FIG. 8. In FIG. 8, the G and D bands of the samples are seen along with additional peaks of hausmannite, confirming that the manganese oxide is intercalated into the carbonaceous matrix at these regions. Hausmannite ($Mn_3O_4$) nanocrystals are known to be synthesized by various methods involving calcination of oxides, hydroxides, carbonates, nitrates or sulphates of manganese at high temperatures in air (Southard, J. & Moore, G. High-temperature Heat Content of Mn3O4, MnSiO3 and Mn3C1. *Journal of the American Chemical Society* 64, 1769-1770 (1942); Ursu, I. et al. Kinetic evolution during the laser/thermal preparation of Mn3O4 from MnCO3. *Journal of Physics B: Atomic and Molecular Physics* 19, L825 (1986)). While most of these methods involve oxidation of the Mn (II) compound, reduction of $KMnO_4$ is also known to bring about $Mn_3O_4$ formation (Weixin, Z., Cheng, W., Xiaoming, Z., Yi, X. & Yitai, Q. Low temperature synthesis of nanocrystalline $Mn_3O_4$ by a solvothermal method. *Solid State Ionics* 117, 331-335 (1999); Zhang, W. et al. Controlled synthesis of Mn3O4 nanocrystallites and MnOOH nanorods by a solvothermal method. *Journal of Crystal Growth* 263, 394-399 (2004)). In this case, although the exact mechanism is still unclear, it is suggested the presence of strong oxidizing agents such as nitric acid ($HNO_3$) to have brought about reduction of $KMnO_4$. While performing the analysis, it was observed that not all spectra for oxidized graphite and graphene nanoplatelets showed the hausmannite peaks. The presence of hausmannite peaks was sensitive to the orientation of the sample and sample spot size, confirming that these peaks were seen only at regions of manganese oxide intercalation.

Figure 2B:
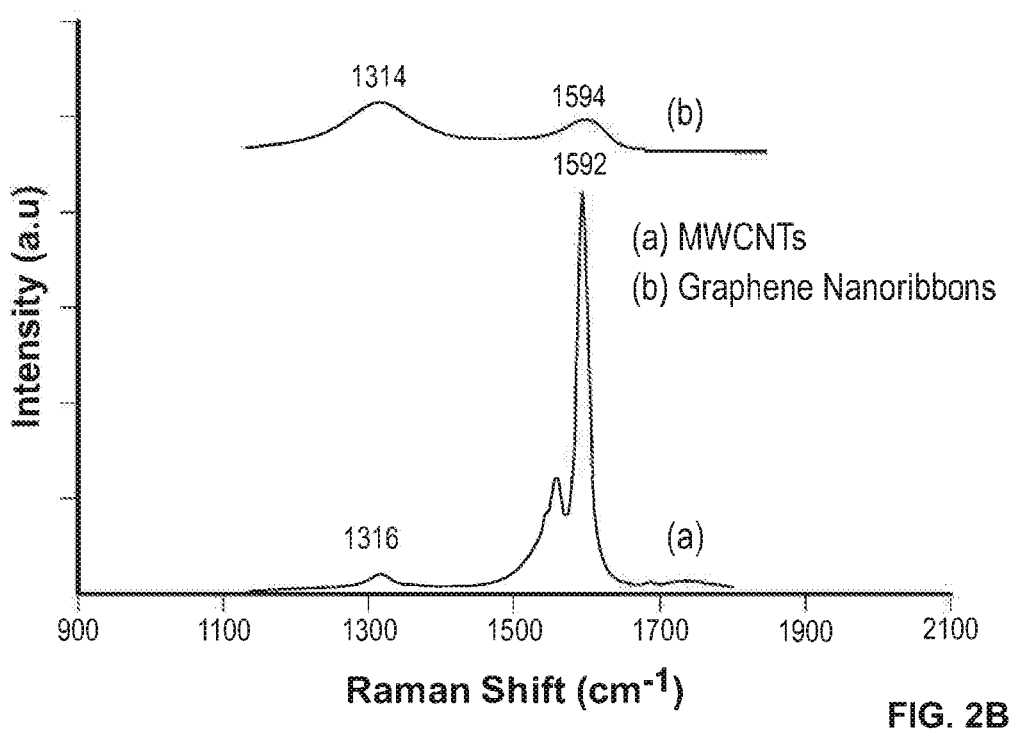

FIG. 2(b) shows the Raman spectrum of graphene nanoribbons and MWCNTs. Similar to spectra for nanoplatelets (in FIG. 2(a)), the spectrum for nanoribbons confirms a broad G band with a shifted peak at 1600 $cm^{-1}$ as well as a prominent D band at 1310 $cm^{-1}$. In comparison to the Raman spectrum of MWCNTs, an increase in $I_D/I_G$ value from 0.045 to 1.57 was seen. This is in consensus with earlier reports on the Raman spectra of nanoribbons derived from chemical oxidation of MWCNTs, where $I_D/I_G$ greater than 1 was observed for nanoribbons (Kosynkin, D. et al. Longitudinal unzipping of carbon nanotubes to form graphene nanoribbons. *Nature* 458, 872-876 (2009)). The shifted G band is due to the oxidative unzipping of MWCNTs, similar to the shift seen due to oxidation of graphite in FIG. 2(a). The high intensity and broad D band is due to the effect of reduction of the average size of $sp^2$ domains in addition to an increase in the number of such small sized disorder domains. With nanoribbons, it was unable to detect any unusual Raman peaks indicative of Manganese, such as the hausmannite peak seen for the nanoplatelets.

Figure 3A:
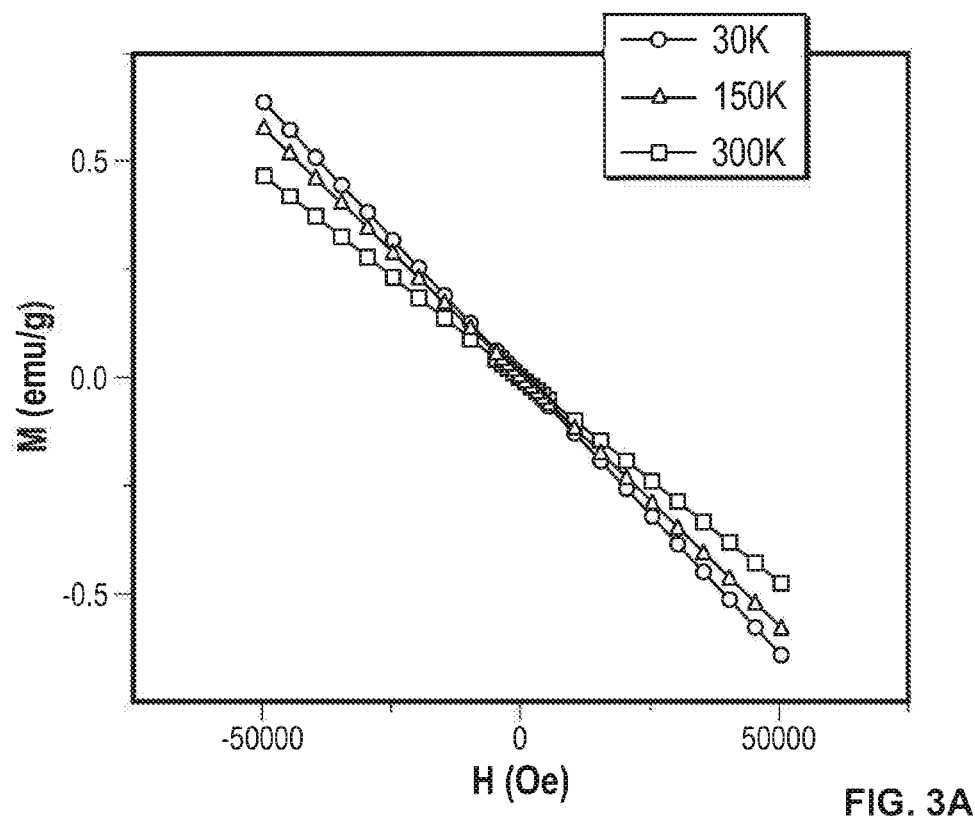
FIGS. 3(a)-3(e). SQUID plots: Magnetization(M) v/s Field strength(H) for (a) Graphite, (b) Oxidized graphite, (c) Graphene nanoplatelets, (d) Reduced Graphene nanoplatelets at 30K, 150 and 300K between −50,000 to 50,000 Oe, Inset: plot between −5000 and 5000 Oe at 300K; (e) ZFC and FC magnetization curves for reduced graphene nanoplatelets revealing a blocking temperature of 40K.
Figure 3B:
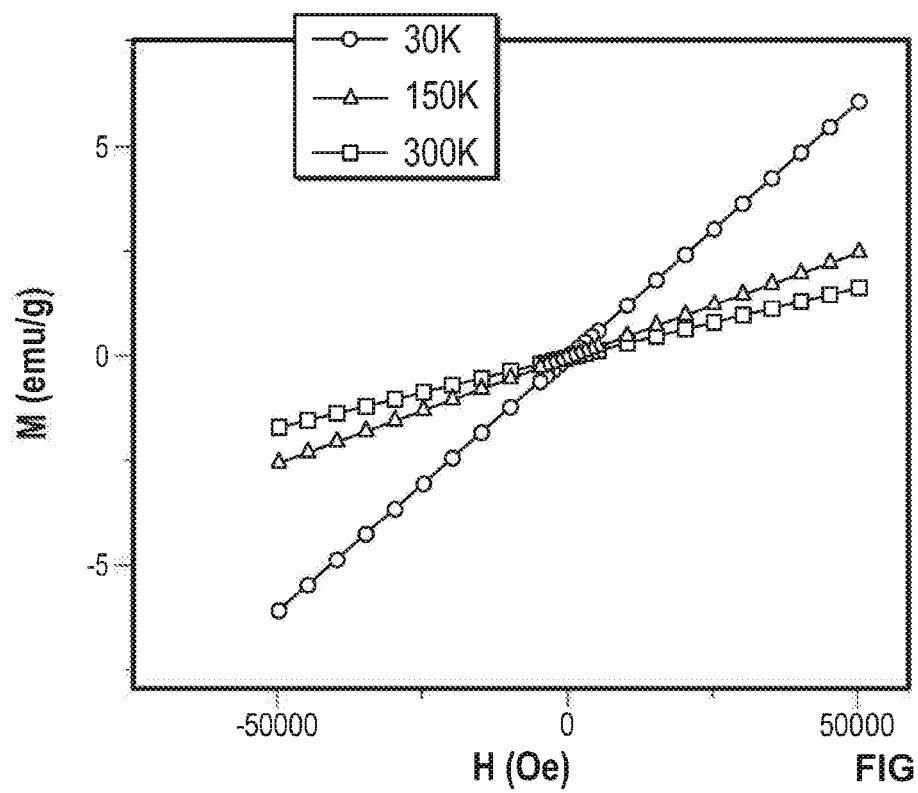
Figure 3C:
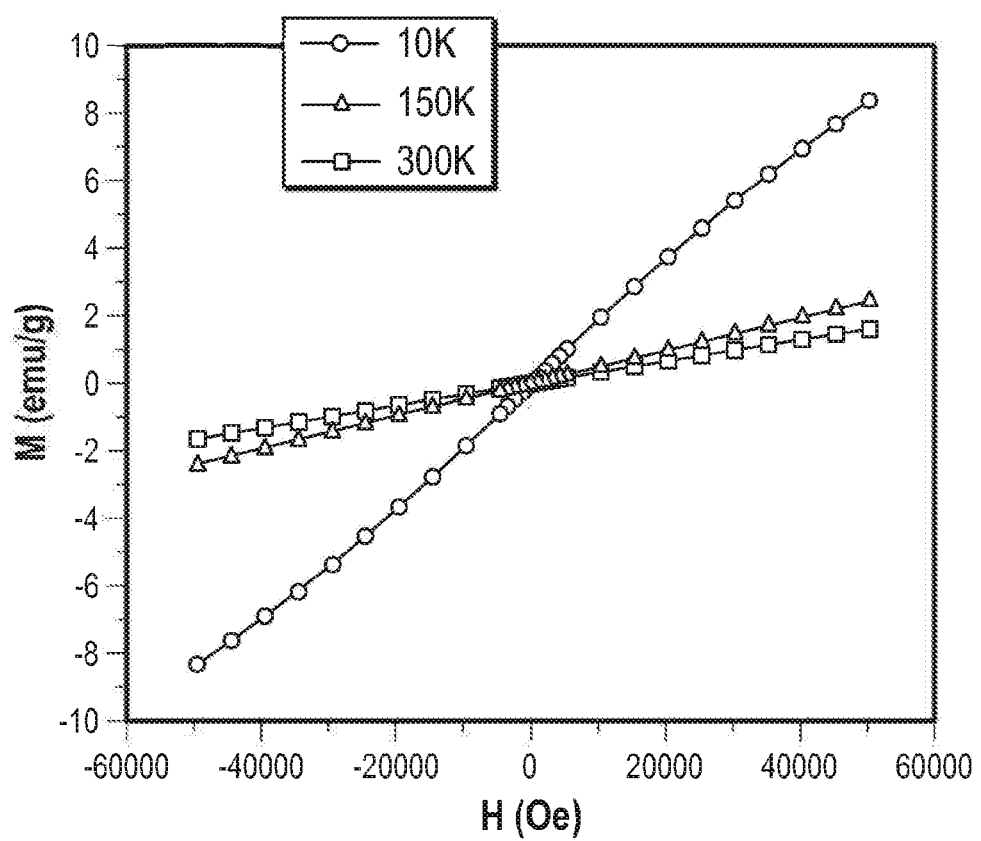
Figure 3D:
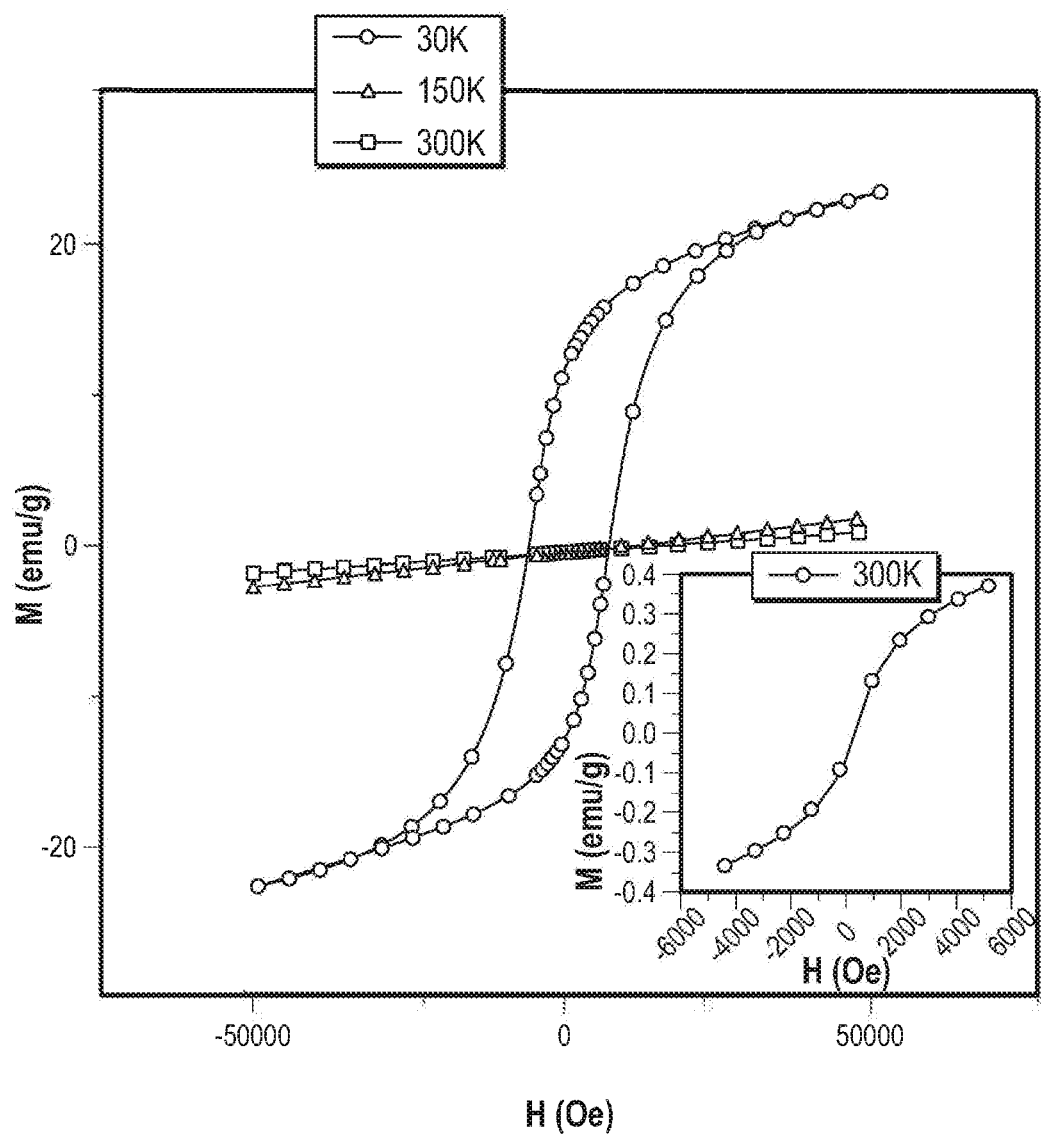
Figure 3E:
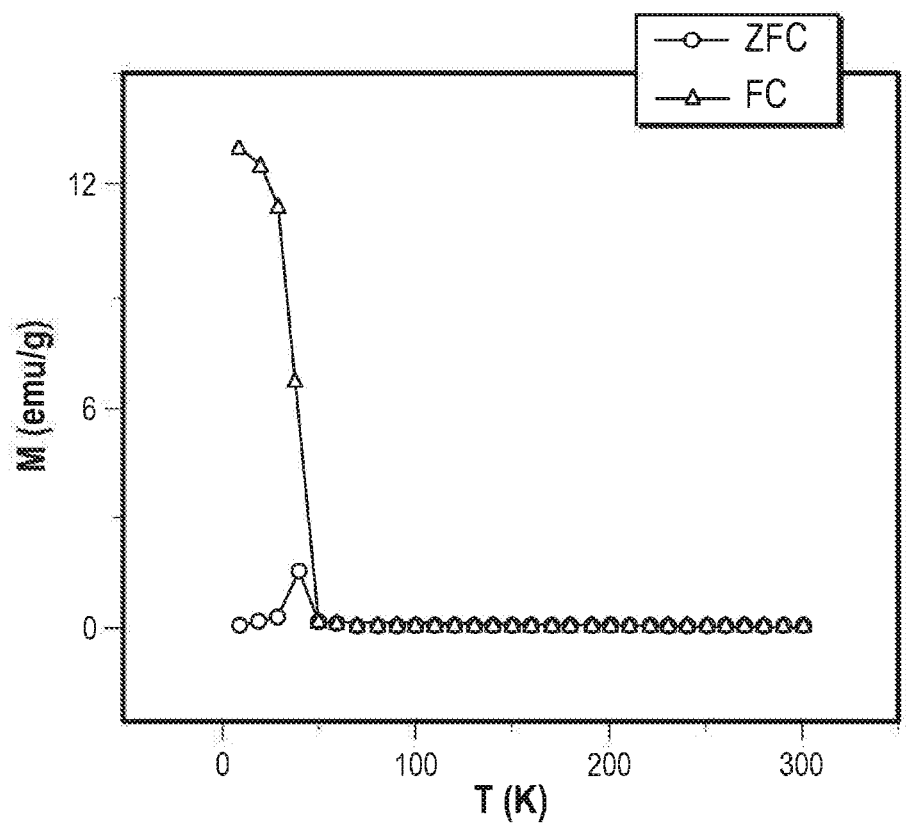

In order to confirm presence of Manganese ($Mn^{2+}$) in nanoplatelets and nanoribbons, elemental analysis by ICPOES was carried out for the dry solid samples. Oxidized graphite, graphene nanoplatelets and reduced graphene nanoplatelets reported to have 484000, 540000 and 516000 ppm of manganese respectively whereas the control graphite has only 0.1 ppm of manganese. This confirms the dominating presence of manganese in these samples. In case of graphene nanoribbons, 570 ppm was reported. Though the experiment was unable to detect any manganese related peaks in the Raman spectrum of graphene nanoribbons, this value confirmed its presence. In order to clarify that it was introduced through $KMnO_4$ based oxidation of MWCNTs, the content of the starting material, MWCNT and the final nanoribbon product were compared. A ~25 fold increase in manganese content was observed, from 25 ppm for MWCNTs to 570 ppm for nanoribbons. This is attributed to the oxidative procedure used in this method. FIGS. 3(a)-3(e) shows the SQUID magnetic characterization of all samples. FIG. 3(a) shows the plot of magnetization (M) versus magnetic field strength (H) for the control, graphite, between −50,000 Oe and 50,000 Oe for three temperatures (30K, 150K, and 300K). The negative slope suggests a decrease in the value of magnetic moments with increase in applied magnetic field which is characteristic of diamagnetic behavior. FIG. 3(b) shows the M vs. H plot for oxidized graphite. A positive slope indicating an increase in the value of the magnetic moments with field strength confirms paramagnetic behavior of the samples. The change to paramagnetism upon oxidation of graphite can be attributed to the presence of the paramagnetic $Mn^{2+}$ ions which were intercalated in the sample as complex manganese oxides during the modified Hummer's protocol. Superparamagnetic transition behavior in reduced graphene nanoplatelets derived from graphite was observed. Superparamagnetism, a magnetic phenomenon observed in nanoparticle clusters (<30 nm) of ferromagnetic nature, is a size dependent phenomenon where a random flip in the direction of alignment of magnetic moments occurs under the influence of temperature. During magnetization measurements, where the sample is subjected to varying magnetic fields at a given temperature, a superparamagnetic material assumes an 'S' shaped curve in a M vs. H plot. This is because the time taken to measure the magnetization is much greater than the time for consecutive flip in the moments. As a result, in the absence of a magnetic field the average magnetization is measured as zero and the curve assumes an 'S' shape instead of a hysteresis loop. FIG. 3(c, d) shows the M vs. H plot for graphene nanoplatelets and reduced graphene nanoplatelets respectively. From FIG. 3(d), it is evident that at lower temperatures (30K), the nanoplatelet sample shows a ferromagnetic hysteresis curve (Whitney, T., Searson, P., Jiang, J. & Chien, C. Fabrication and Magnetic Properties of Arrays of Metallic Nanowires. *Science* (New York, N.Y.) 261, 1316 (1993); Wang, J., Chen, Q., Zeng, C. & Hou, B. Magnetic Field Induced Growth of Single Crystalline Fe3O4 Nanowires. *Advanced Materials* 16, 137-140 (2004)). From the inset of FIG. 3(d), it is evident that superparamagnetic behavior is observed at room temperature. The zero field cooling (ZFC) and field cooling (FC) curves plotted at uniform field strength of 500 Oe and between 0 and 300K are seen in FIG. 3(e). The peak in the ZFC curve reveals a blocking temperature ($T_B$) of 40K, indicating a transition between ferromagnetic and superparamagnetic states.

The magnetic behavior of reduced graphene nanoplatelets exhibits a sharp resemblance to that of Hausmannite as previously reported (Du, J. et al. Hausmannite $Mn_3O_4$ nanorods: synthesis, characterization and magnetic properties. *Nanotechnology* 17, 4923 (2006)). Ferromagnetism at low temperatures and paramagnetism at higher temperatures has been reported in hausmannite. Similar to reduced graphene nanoplatelets, hausmannite shows a $T_B$ of 40K and the plot of M vs. H at different temperatures for both materials are similar (Du, J. et al. Hausmannite $Mn_3O_4$ nanorods: synthesis, characterization and magnetic properties. *Nanotechnology* 17, 4923 (2006)). This verifies the intercalation of the complex manganese oxides in nanoplatelets and we can attribute this behavior to the presence of the complex manganese oxide, in addition to the nanostructure of the graphene nanoplatelets (~20 nm wide). The remnant magnetization of the hysteresis curve at 30K is 12.47 emu/g and the coercivity is 6298.68 Oe. According to previous literature, the high coercivity can be attributed to the single domain nature and high shape anisotropy of the sample.

There have been several theoretical and a few experimental reports on the existence of room temperature ferromagnetism in graphene, graphene oxide and nanoribbon samples (Matte, H. S. S. R., Subrahmanyam, K. & Rao, C. Novel magnetic properties of graphene: Presence of both ferromagnetic and antiferromagnetic features and other aspects. *The Journal of Physical Chemistry C* 113, 9982-9985 (2009); Wang, Y. et al. Room-temperature ferromagnetism of graphene. *Nano Letters* 9, 220-224 (2008)). Recent experimental work by Wang et al. using SQUID magnetometer on graphene samples that were prepared from graphite oxide and later reduced and annealed, have shown room temperature ferromagnetism (Wang, Y. et al. Room-temperature ferromagnetism of graphene. *Nano Letters* 9, 220-224 (2008)). The possible origin of magnetism is attributed to the long range coupling of spin units existing as defects due to the annealing process. They verified the absence of metallic impurities and attribute the magnetism to the inherent features in graphene due to the processing. In this case, the presence of manganese in the samples is established through ICPOES and Raman spectroscopy. This is further corroborated by the similarity in the magnetic data of nanoplatelets and hausmannite. Even though oxidized graphite samples show the presence of hausmannite, they exhibit paramagnetic behavior (Du, J. et al. Hausmannite $Mn_3O_4$ nanorods: synthesis, characterization and magnetic properties. *Nanotechnology* 17, 4923 (2006)). Considering that there are several other factors at play in case of reduced graphene nanoplatelets, the room temperature superparamagnetism of nanoplatelets is attributed to the combination of presence of intercalated manganese oxides, the nanocluster size of the platelets and long range coupling of spin units existing as defect sites on $sp^2$ carbon atoms in graphene. Further, the long range orderly coupling of spin units can be due to intramolecular interaction in individual sheets or intermolecular interaction between neighboring sheets of graphene multi-layers.

Figure 4A:
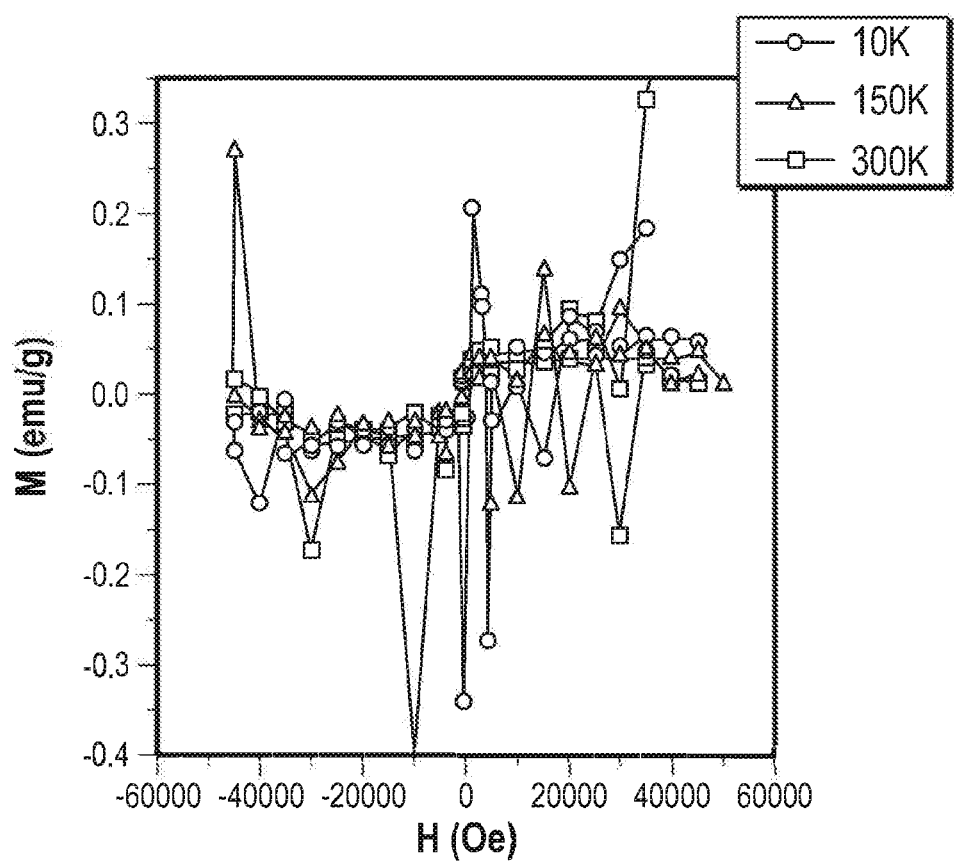
FIGS. 4(a)-4(c). SQUID plots: Magnetization (M) v/s Field strength (H) between −50,000 Oe and 50,000 Oe (a) M vs. H at three temperatures (10, 150 and 300K) for MWCNTs; (b) M vs. H plot for graphene nanoribbons at 30K, 150K and 300K, Inset: M vs. H between −4000 Oe and 4000 Oe at 300K showing hysteresis loops; (c) ZFC and FC plot for GNR revealing high blocking temperature greater than 300K.
Figure 4B:
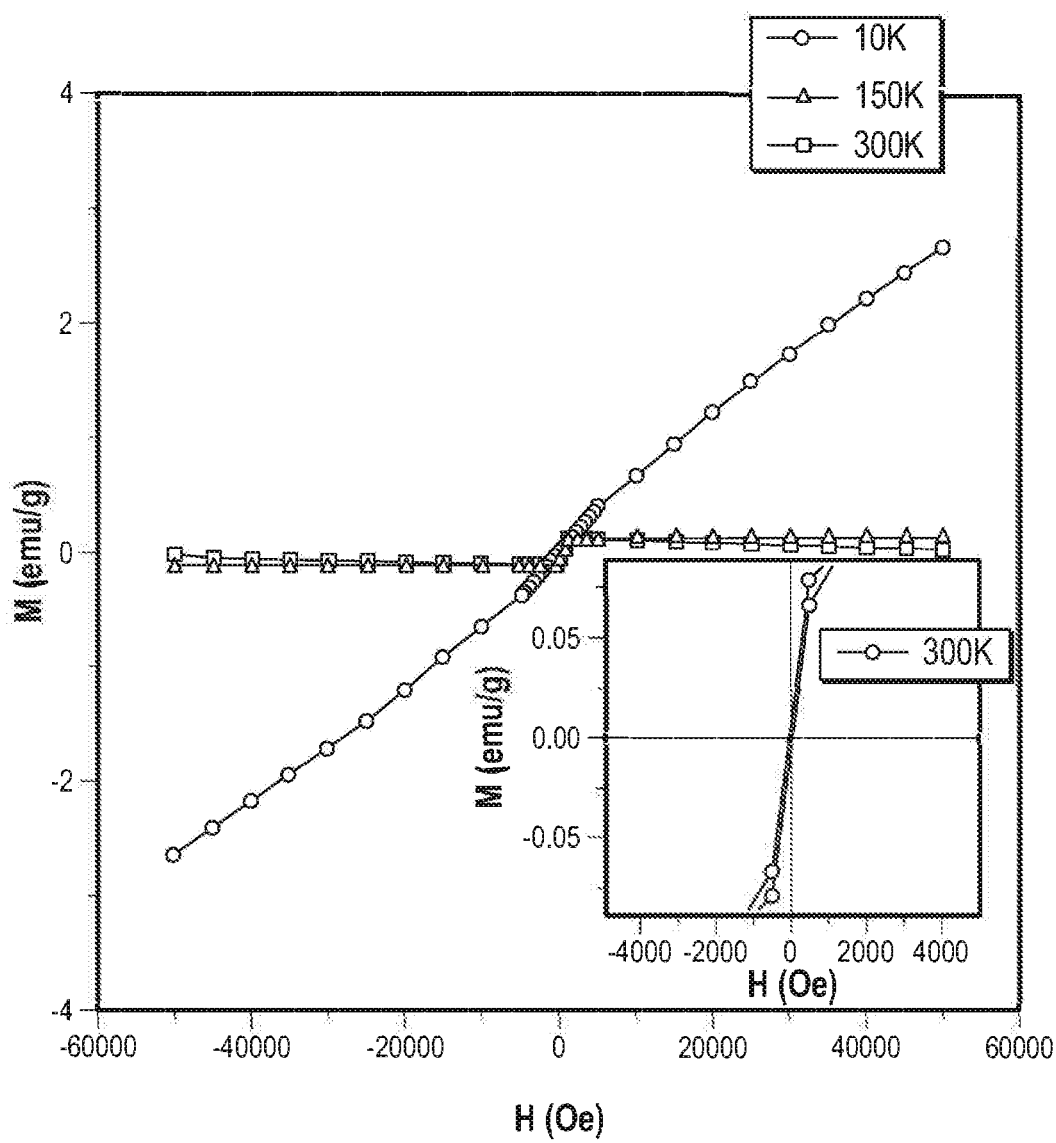
Figure 4C:
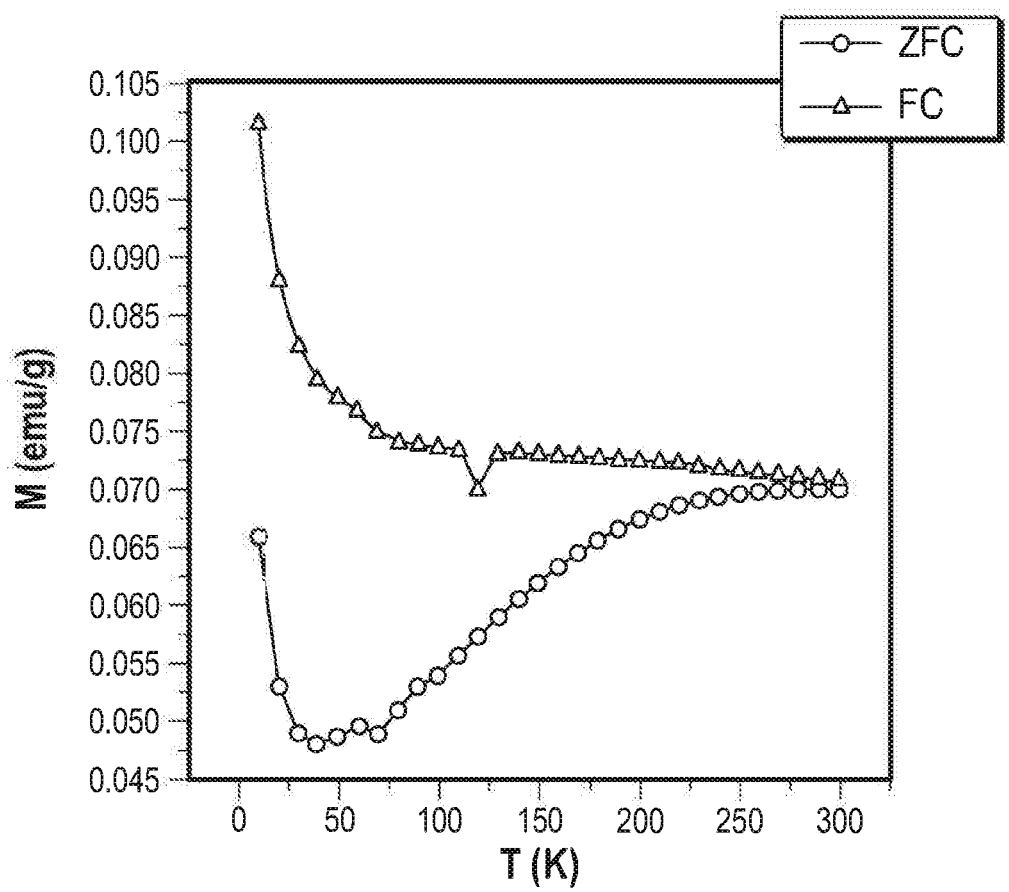
Figure 5:
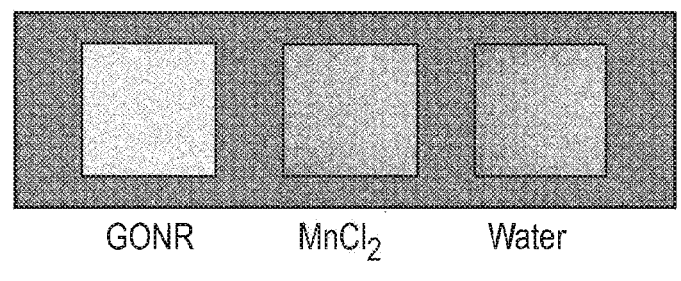
FIG. 5. $T_1$-weighted MRI phantom of GONR compared with $MnCl_2$ and water.

The SQUID analysis of graphene nanoribbons synthesized from MWCNTs also shows interesting magnetic properties at room temperature. Magnetization versus field strength plot for MWCNTs is shown in FIG. 4(*a*). No coherent magnetic pattern is seen and the magnetic signals are extremely weak at all three temperatures. The plot of M vs. H for graphene nanoribbons shows superparamagnetic behavior as seen in FIG. 4(*b*). However, the inset in FIG. 4(*b*) shows parallel lines of the hysteresis curves at 300K indicating ferromagnetic behavior with a very low remanence. FIG. 4(*c*) indicates FC/ZFC plots and a maximum value on the ZFC curve is seen around >300K which reveals a high blocking temperature, Ts, greater than room temperature. This explained the thin hysteresis loop at 300K, where a transition of magnetic states was at play. The saturation magnetization seen at 300K was 0.1 emu/g at 2500 Oe. The sample showed a coercive field of 250 Oe at 10K. It has been reported that iron oxide nanoparticles as well as microstructures exhibit room temperature superparamagnetism (Deng, H. et al. Monodisperse Magnetic Single-Crystal Ferrite Microspheres. *Angewandte Chemie International Edition* 44, 2782-2785, (2005); Zhao, L. et al. Morphology-controlled synthesis of magnetites with nanoporous structures and excellent magnetic properties. *Chemistry of Materials* 20, 198-204 (2007)). However, obtaining room temperature ferromagnetism in iron oxides or graphene requires post synthetic high temperature annealing processes or embedding the particles in an antiferromagnetic complex (Wang, Y. et al. Room-temperature ferromagnetism of graphene. *Nano Letters* 9, 220-224 (2008); Sun, S., Murray, C. B., Weller, D., Folks, L. & Moser, A. Monodisperse FePt Nanoparticles and Ferromagnetic FePt Nanocrystal Superlattices. *Science* 287, 1989-1992 (2000)). Recently, room temperature ferromagnetism by synthetic processes at comparatively low temperatures (185° C.) in magnetite and maghemite iron oxide nanoparticles has been reported (Tan, Y., Zhuang, Z., Peng, Q. & Li, Y. Room-temperature soft magnetic iron oxide nanocrystals: Synthesis, characterization, and size-dependent magnetic properties. *Chemistry of Materials* 20, 5029-5034 (2008)). This study reports a size dependent magnetic behavior, and the blocking temperature ($T_B$, an indicator of transition from ferromagnetism to superparamagnetism) shows an increase from 25K for the 3.2 nm particles to 330K for the 5.4 nm particle size. In the present case, with simple chemical synthetic procedure at temperatures of 70° C., it was able to achieve room temperature ferromagnetic to superparamagnetic transition with $T_B$ values >300K. Earlier reports on room temperature superparamagnetism in $Fe_2O_3$ filled MWCNTs has been reported (Li, J.-h. et al. An easy approach to encapsulating $Fe_2O_3$ nanoparticles in multiwalled carbon nanotubes. *New Carbon Materials* 25, 192-198 (2010)).

Relaxivity of Graphene Oxide Nanoplatelets and Nanoribbons:

Single point relaxation measurements were performed at 21.42 MHz, 0.5T and 27° C. on all graphene samples dispersed in 1% Pluronic F127 surfactant solution at 0.05% concentration. Ultrasonic exfoliation of oxidized graphite in water resulted in a stable colloidal suspension containing thin sheets of oxidized graphene. This was feasible due to the hydrophilic nature of hydroxyl and carboxyl groups. Oxidized graphene sheets are hence different from pristine graphene. The process of reduction, as used here, did not entirely remove all the oxygen groups. The oxidative unzipping of MWCNTs was also known to add these functional groups to the oxidized graphene nanoribbons. Graphene nanoplatelets, reduced graphene nanoplatelets and graphene nanoribbons can form homogeneous, stable dispersions in aqueous, biocompatible solutions such as Pluronic. Table 1 (a, b) provide details on the concentration of metal ion (Manganese), relaxation rates and relaxivity of each sample. From Table 1 (a) it is clear that oxidized graphite showed enhanced $r_1$ and $r_2$ relaxivities when compared to graphene nanoplatelets and reduced graphene nanoplatelets. It has been reported that the NMR relaxivity measurements of Mn-DPDP (commercially known as Teslascan®), which is a manganese based MRI contrast agent, shows relaxivity values of $r_1=1.88$ mM$^{-1}$ s$^{-1}$ and $r_2=2.18$ mM$^{-1}$s$^{-1}$ in aqueous solutions at 20 MHz (Schwert, D., Davies, J. & Richardson, N. in *Contrast Agents I* Vol. 221 *Topics in Current Chemistry* (ed Werner Krause) 165-199 (Springer Berlin/Heidelberg, 2002)). Compared to Teslascan®, oxidized graphite showed double the rate of r, and four times in case of $r_2$. Graphene nanoplatelets showed similar relaxivity values when compared to the clinical counterpart Teslascan®. However, as seen in Table 1 (b) graphene nanoribbons showed much higher relaxivity ranges compared to Teslascan and nanoplatelets. Due to detection limitations of the equipment in analyzing trace levels of manganese in small sample volumes, the metal content of the samples were analyzed from two different analytical laboratories which provided us a range of concentration of manganese in the nanoribbons and thus an upper and lower bounds of the relaxivity of nanoribbons was calculated. Range of $r_1$ is 2.92 to 9.8 mM$^{-1}$s$^{-1}$ and $r_2$ is 14.8 to 50.3 mM$^{-1}$s$^{-1}$. Table 1 (b) also shows that nanoribbons exhibit promising contrast agent properties when compared to relaxivities of other clinical contrast agents based on Gadolinium (Gd-DTPA) and Super paramagnetic Iron Oxides (Comibidex) (Reichenbach, J. et al. 1H T1 and T2 measurements of the MR imaging contrast agents Gd-DTPA and Gd-DTPA BMA at 1.5 T. *European*

Radiology 7, 264-274 (1997); Corot, C., Robert, P., Idée, J. M. & Port, M. Recent advances in iron oxide nanocrystal technology for medical imaging. *Advanced drug delivery reviews* 58, 1471-1504 (2006)).

In Vitro Phantom MRI:

MRI phantom imaging was performed to compare MR signal contrast between aqueous graphene nanoribbon samples, $MnCl_2$ which is a widely used preclinical MRI contrast agent and water as controls. Representative $T_1$ and $T_2$ weighted phantom MRI images show a significant contrast enhancement in case of the nanoribbon samples when compared to $MnCl_2$ ($r_1$=9.2 $mM^{-1}s^{-1}$; $r_2$=93 $mM^{-1}s^{-1}$) at the same $Mn^{2+}$ concentration and water. Mean signal intensity ratios of nanoribbons and $MnCl_2$ with respect to water were compared and as seen in Table 2 (b), a higher signal contrast for nanoribbons was seen in case of $T_1$ as well as $T_2$. This is attributed to the interesting room temperature magnetic properties of nanoribbons which results in significant enhancement of relaxation rates of the proton molecules.

TABLE 1 (a)

Relaxation efficiencies of oxidized graphite, graphene nanoplatelets and reduced graphene nanoplatelets dispersed in 1% Pluronic F127 solutions

| Sample | [Mn] mM | $R_1$ ($s^{-1}$) | $R_2$ ($s^{-1}$) | $r_1$ $mM^{-1}s^{-1}$ | $r_2$ $mM^{-1}s^{-1}$ |
|---|---|---|---|---|---|
| Oxidized graphite | 0.12 | 3.02 | 10.98 | 22.09 | 74.74 |
| Graphene nanoplatelets | 0.98 | 1.93 | 3.3 | 1.59 | 2.88 |
| Reduced graphene nanoplatelets | 1.98 | 0.88 | 8.84 | 0.25 | 3.44 |
| Teslascan (Mn DPDP) | | | | 1.88 | 2.18 |

** All values are calculated at 1.5 T and 21.42 MHz

TABLE 1 (b)

Relaxation efficiencies of graphene nanoribbons dispersed in 1% Pluronic F127 surfactant, compared with clinically used MRI contrast agents. $R_1$ (pluronic) = 0.37 $s^{-1}$, $R_2$ (pluronic) = 2.02 $s^{-1}$

| Sample | [Mn] mM | $R_1$ ($s^{-1}$) | $R_2$ ($s^{-1}$) | $r_1$ $mM^{-1}s^{-1}$ | $r_2$ $mM^{-1}s^{-1}$ |
|---|---|---|---|---|---|
| Graphene nanoribbons (GNR) | 0.045 | 3.66 | 14.5 | 73.2 | 251.4 |
| Teslascan (Mn DPDP) | | | | 1.88 | 2.18 |
| Magnevist (Gd DTPA) | | | | 4.59 | 5.15 |
| Comibidex (Ferrumoxtran) | | | | 9.9 | 65 |

**All values are calculated at 1.5 T and 20 MHz.

TABLE 2

Comparison of mean signal intensities ratios from $T_1$- and $T_2$- phantom images with respect to water

| SAMPLE | $T_1$ image intensity ratio to water | $T_2$ image intensity ratio to water |
|---|---|---|
| GONR | 1.465 | 5.05 |
| $MnCl_2$ | 0.9999 | 2.272 |

In summary, this example demonstrated the synthesis of a new class of functionalized graphene nanoplatelets and nanoribbons by simple chemical oxidative procedure using $KMnO_4$. In the example, functionalized graphene nanoplatelets and nanoribbons were successfully synthesized and the presence of manganese and its magnetic contribution in graphene nanoplatelets were verified. In case of graphene nanoribbons, very interesting magnetic properties were found, with room temperature magnetic transition from ferromagnetism to superparamagnetism. The example also shows that the structure, chirality and presence of magnetic metal ions such as manganese and iron enhance relaxation rates of these carbon materials significantly. These nanoplatelets and nanoribbons can be used as functionalized graphene based contrast agents for MRI imaging.

Example 2

Figure 6:
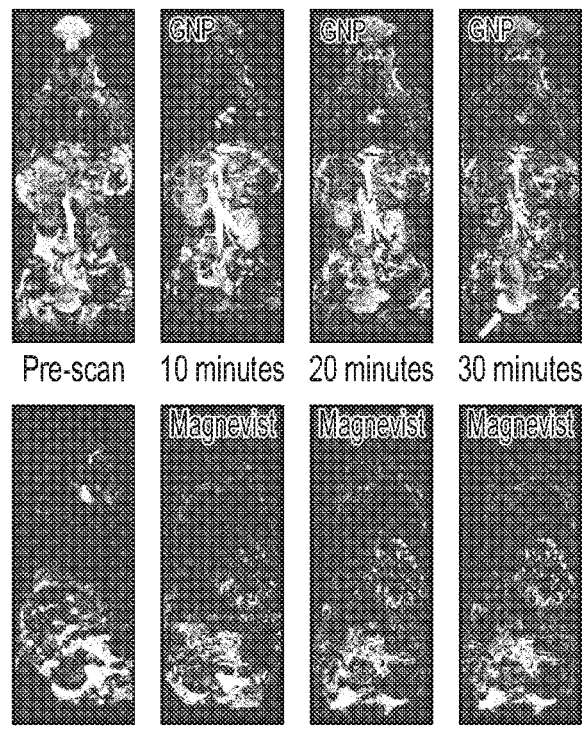
FIG. 6. Representative MR Images of a mouse before and after injection of water-soluble GNP MRI CAs at a dosage of 0.25 mmols/kg. At these low doses, 100 times lower than doses used for clinical Gd-based CA such as Magnevist, excellent bright contrast enhancement is obtained throughout the vasculature due to the circulating nanoparticles.

The novel graphene nanoplatelets (GNPs; small stacks (1-12 layers) of graphene (one-atom-thick sheets of graphite) with thickness between 1 to 5 nanometers (nm) and diameters of ~50 nm) (FIGS. 1a and 1b) was tested as MRI contrast agent in MRI scans of a mouse. The GNPs were monodispersed, water-soluble, intercalated (insertion of chemical species within the voids between two graphene sheets), and coordinate with trace amounts of manganese (0.1% w/w (w=weight) of Manganese in GNPs, i.e. 0.1 gram of manganese per 100 gram of GNPs). The GNPs showed relaxivity of r1=45 $mM^{-1}s^{-1}$ which is nearly 16 times higher than Mn-DPDP (Teslascan, clinical Mn-based CA, r1=2.8 $mM^{-1}s^{-1}$ at 3T) and ~10 times greater than Gd-DTPA (Magnevist, Clinical Gd-based CA, r1=4.2 $mM^{-1}s^{-1}$ at 3T). Scans using $T_1$ weighted small animal MRI using a 3 Tesla clinical scanner (FIG. 6) showed ~100 times greater contrast enhancement compared to Magnevist at clinical dosages.

Example 3

Graphene Nanoplatelets (GNPs)

First, graphite oxide (GO) is prepared from analytical grade micro-graphite using modified Hummer's method (treatment with potassium permanganate and concentrated surphuric acid) and converted to graphene nanoplatelets (GNPs) by sonication for 1 h in an ultrasonic bath cleaner (Stankovich, S.; Dikin, D. A. et al. *Nature* 2006, 442, 282). Next, the GNPs is water solubilized using a synthesis protocol that is similar to a cycloaddition reaction used to add carboxylic acid functionalities across carbon-carbon double bonds of fullerenes and metallofullerenes (Sithamaran, B.; Zakharian, T. Y. et al. *Molecular Pharmaceutics* 2008, 5, 567).

Controls:

Magnevist is used in experiments where controls are needed, since it is considered the benchmark for clinical MRI contrast media. Additionally, the physio-chemical, pharmacological, pharmacokinetic and imaging properties of GNP MRI CAs is compared to published values 5,9 of other FDA-approved clinical Gd-based MRI CAs such as Omniscan (gadodiamide, Gd-DTPA-BMA, GE Healthcare), OptiMARK (gadoversetamide, Gd-DTPABMEA, Covidien), Magnevist (gadopentetate dimeglumine, Gd-DTPA, Bayer Schering Pharma), MultiHance (gadobenate dimeglumine, Gd-BOPTA, Bracco Diagnostics), Gadovist (gadobutrol, Gd-BT-DO3A, Bayer Schering Pharma) and Dotarem (gadoterate meglumine, Gd-DOTA, Guerbet).

Animals:

Wistar rats (Charles River labs, Wilmington, Mass.) is used since this animal model has been widely used in previous preclinical MRI CA studies (Vogler, H.; et al; *European Journal of Radiology* 1995, 21, 1).

Synthesize and Functionalize GNP MRI CAs for Water-Solubility and Physio-Chemical Characterization:

Osmolality:

This test measures the concentration of all chemical particles found in the fluid component of blood. Osmolality is an important factor in analysis of tolerance for contrast medium, whereby both local and systemic reactions play their part especially at higher doses (Cohan, R. H.; Leder, R. A. et al. *J. Invest Radiol* 1990, 26, 224; Gennaro, A. R. *Remington's Pharmaceutical Sciences, 17th edn* 1985, 1455; Runge, V. M.; Kirsch, J. E.; Burke, V. J. *J Magn Reson Imaging* 1992, 2, 9). Osmolality is determined using a differential thermistor osmometer at 37° C. Two GNP concentrations, 0.5 mol/l solution (0.57 osmol/kg) and for the 1 mol/l solution (1.39 osmol/kg), is used. These values have been chosen based on preclinical studies of other Gdbased MRI CAs.

Partition Coefficient:

Partition coefficient analysis offers a measure of the hydrophilicity ("water loving") or hydrophobicity ("water fearing") levels of the GNP MRI CAs (Leo, A.; Hansch, C.; Elkins, D. *Chem Rev* 1971, 71, 525). The partition coefficient allows estimation of GNP distribution within the body. If GNPs show high partition coefficients, this is an indicator that this CA will be preferentially distributed to hydrophobic compartments such as lipid bilayers of cells and if low partition coefficient are observed, GNPs will be preferentially found in hydrophilic compartments such as blood serum. The partition coefficient is measured using butanol and Tris-HCl buffer (pH 7.6). After complete separation of the phases, the GNP concentration in the butanol and buffer is determined by means of Raman spectroscopy.

In Vitro Relaxivity:

The relaxivity r (3 T clinical MR scanner, temperature=37° C.) of GNPs in water and bovine plasma is calculated using the equation: $r_1=(R_1-R_0)/[Mn^{2+}]$ where $R_1$ and $R_0$ are the longitudinal relaxation rates ($R_{0,1}=1/T_{0,1, S-1}$) of the GNP solution and plain water or bovine plasma, respectively and $[Mn_{2+}]$ is the manganese concentration.

Protein Binding:

Efficacy of the CA may be affected by the degree to which it binds to blood plasma proteins (Vogler, H.; et al; European Journal of Radiology 1995, 21, 1). Thus, protein binding is measured in human plasma at a concentration of 1 mmol/l by means of ultrafiltration.

Histamine Release:

Histamine release of macrophages is an important phenomenon connected to various adverse reactions to MRI CAs (Lorenz, W.; Doenicke, A. et al. *The role of histamine in adverse reactions to intraveneous agents In: Thornton, editor. Adverse Reactions of Anaesthetic Drugs. Elsevier Press* 1981, 169). Mast cells (also known as mastocytes and labrocytes), resident cells in several tissue types, containing granules rich in histamine is incubated in buffer containing GNP MRI CAs (Magnevist is used as the control) concentrations ranging from 0 to 250 mmol/l. The Iso, the concentration at which histamine release approximates 50% of the release caused by the histamine liberator compound 48/80, is calculated.

In Vivo MRI Studies to Assess the Impact of Water-Soluble GNPs as High Performance MRI CAs in Rats:

MRI investigations is performed on rats with lesions that mimic lesions in the heart, brain or muscles in humans. Induction of cerebral infarcts, brain tumors or intramuscular tumors in rats (male, Wistar rats, 170-180 g, n=3 per group) is achieved using well established protocols (Vogler, H.; et al; *European Journal of Radiology* 1995, 21, 1). Before imaging, the animals are anesthetized (isoflurane), and a catheter is fixed in a tail vein for injection of the contrast agent. Immediately after contrast agent injection, approximately 5 mL of 0.9% normal saline is injected to ensure that all the MRI CA is cleared from the infusion tubing. A 3 T clinical MR scanner (Siemens medical systems, Malvems, Pa.) is used, and $T_1$-weighted spin-echo-images are acquired. Imaging is performed before and 1 min after injection of 0.1 mmol/kg of GNPs or Magnevist (control) and 1 min after injection of an additional dose of 0.2 mmol/kg given 5 min after the first dose into the same animal. Post-contrast images are obtained in the same plane and with the same parameters as the pre-contrast study. The signal to noise ratio and the contrast to noise ratio (CNR) in the experimental and control groups are obtained in the field of interest and statistical analysis performed. Images are reviewed by two radiologists experienced in the interpretation of MR images. Efficacy of the CA is evaluated and a consensus among clinical practitioners are reached using the following criteria: a) provision of additional information toward diagnosis; b) increase in the confidence of the diagnosis; c) detection of lesions not otherwise visible; and, d) provision of important information for greater characterization of lesions seen with other pulse sequences. In cases in which lesion enhancement is evident, the agent ise judged to be of: a) no help; b) minor help; c) moderate help; or, d) major help in diagnosis.

In Vivo Pharmacokinedcs, Biodistribution and Toxicity Studies in Rats Elimination and Biodistribution:

To determine long-term elimination and biodistribution, 0.25 mmol/kg of GNP MRI CAs are injected intravenously into a tail vein of five male and five female Wistar rats, weighing 90-110 g. The animals are then placed in metabolic cages.

Urine and Feces are Collected Daily and the GNP and Manganese Content Measured:

Animals are sacrificed 7 days post-injection. Blood, liver, kidneys, spleen, bone samples (femur), brain and the remaining body are collected for measurement of GNP content by Raman spectroscopy and manganese content by inductively-coupled plasma (ICP) spectroscopy.

Pharmacokinetics:

Experiments are performed on five Wistar rats, weighing 90-110 g. Before and during the experiment, the animals are housed in individual metabolism cages. $^{125}$I-GNP ($^{125}$I radioactive half life=59.4 days) is injected into the tail vein at a dose of 0.25 mmol/kg. blood (0.5 ml), and blood is withdrawn from the jugular vein before and at 5, 10, 20 and 30 min and 1, 1.5, 2, 3, 6, and 24 h and 7 days after GNP MRI CA injection. Urine is collected quantitatively at 0.5, 1, 2, 3, 6 and 24 h and, then, daily for 7 days. Feces is collected quantitatively daily for 7 days. Aliquots of urine, feces and plasma samples are assayed radiometrically by gamma scintillation counter. Urine fractions and plasma samples (5 or 20 min and 2 h after injection) are assayed for potential metabolites using HPLC analysis.

A model-independent approach is applied using the pharmacokinetic program, TOPFIT, for the calculation of the terminal elimination half-life in plasma, as well as clearance and steady state volume of distribution from the plasma and urine data (Heinzel, G.; Woloszczak, R. et al. Pharmacokinetic and pharmacodynamic data analysis system New York: Gustav Fischer Verlag Stuttgart, Jena 1993).

Acute Toxicity:

The GNP MRI CA (2 mols/l) is injected intravenously into male and female Wistar rats (90-110 g, male to female ratio 1:1). Doses are 10, 50, 100, 250 mmol/kg and each dosage group is comprised of eight animals. The animals are monitored throughout an observation period of 7 days post injection. The $LD_{50}$ are calculated by means of probit analysis (Neter, J.; Kutner, M. H.; et al. Applied linear statistical models 1996, WCB McGraw).

Example 4

This example demonstrates that potassium permanganate-based oxidative chemical procedures used to synthesize graphite oxide or graphene nanoparticles leads to the confinement (intercalation) of trace amounts of $Mn^{2+}$ ions between the graphene sheets, and that these manganese intercalated graphitic and graphene structures show disparate structural, chemical and magnetic properties, and high relaxivity (up to 2 order) and distinctly different nuclear magnetic resonance dispersion profiles compared to paramagnetic chelate compounds. The results show that confinement (intercalation) of paramagnetic metal ions within graphene sheets, and not the size, shape or architecture of the graphitic carbon particles is the key determinant for increasing relaxivity, and thus, identifies nano confinement of paramagnetic ions as novel general strategy to develop paramagnetic metal-ion graphitic-carbon complexes as high relaxivity MRI contrast agents.

Materials and Method:

1. Graphene Nanoplatelets and Nanoribbons Synthesis

A total of 5 batches of graphene nanoplalets and nanoribbons were prepared and characterized. All the results presented except the relaxivity results are representative data of a single batch. Oxidized micro-graphite was prepared from analytical grade micro-graphite (Sigma Aldrich, New York) by modified Hummer's method as described in Example 1. In a typical exfoliation procedure, dried oxidized micro-graphite (200 mg) was suspended in a round bottom flask containing water (200 ml) and sonicated for 1 h in an ultrasonic bath cleaner (Fischer Scientific, FS60, 230W). 50 ml of this uniform solution was centrifuged and pellet was dried overnight to obtain oxidized graphene nanoplatelets. The remaining 150 ml was treated with hydrazine hydrate (1.5 ml, 37.1 mmol), and heated in an oil bath at 100° C. under a water cooled condenser for 12 h, resulting in a black precipitate. The product was isolated, and washed over a medium sintered glass filter funnel with water (500 ml) and methanol (500 ml) and dried by continuous air flow to yield reduced graphene nanoplatelets.

Graphene nanoribbons were prepared from MWCNTs (Sigma Aldrich, N.Y.) in a procedure similar to the one described in Example 1. MWCNTs (150 mg, 12.5 mequiv of carbon) were suspended in 30 ml of cone. $H_2SO_4$ for 2 h. $KMnO_4$ (750 mg, 4.75 mmol) was added, and the mixture was allowed to stir for 1 h. The reaction was then heated in an oil bath at 55-70° C. for an additional 1 h, until completion. It was cooled to room temperature, and the product was washed with water, ethanol and ether, and subsequently isolated by centrifugation.

2. Characterization of Magnetic Behavior

Magnetization of graphite, graphene and control samples was studied using a super conducting quantum interference device (SQUID) magnetometer with a sensitivity of about $10^{-8}$ emu. The samples were carefully weighed and loaded in gelatin capsules. Samples were analyzed between the applied magnetic field range of −50000 Oe to 50000 Oe between 0 and 300K. In the Field cooling and Zero Field cooling mode, a coercive field of 500 Oe was applied for studying magnetization as a function of temperature.

3. EPR Measurements

All the EPR spectra were measured at room temperature (~296 K) under similar experimental conditions on a Bruker X-band EPR Spectrometer operating at ~9.8 GHz microwave frequency with high 100 KHz magnetic field modulation frequency. The magnetic fields and g-values were calibrated with a standard solid sample of diphenyl picrylhydrazyl (DPPH, g=2.0036). The EPR of blank quartz tube was measured to calibrate EPR baseline for the EPR spectra. All EPR spectra were measured twice, first with 1 k Gauss sweep width, and next with 6 k Gauss sweep width. The solid samples of graphite, graphene and controls were loaded into Wilmad Quartz EPR tubes. The quartz EPR sample tubes were washed thoroughly with deionized water, and dried prior to loading of the samples. The EPR measurements on the aqueous samples were done by using a quartz flat tube designed for aqueous and other solvents with high dielectric constants. Before loading the liquid samples, the quartz EPR flat tube was washed thoroughly with deionized water and dried. The loading of aqueous samples into the quartz flat tube was done carefully into the flat portion of the tube for maximum sensitivity.

4. Proton Relaxivity Measurements

For relaxivity measurements, 1 mg of oxidized micro-graphite, oxidized graphene nanoplatelets, reduced graphene nanoplatelets or graphene nanoribbon samples were dispersed in 2 ml of biologically compatible 1% Pluronic F127 surfactant solution, bath sonicated at 30 W for 10 min, and finally centrifuged at 5000 rpm for 1 h. The centrifugation allowed the non-water-solubilized large and dense graphene nanoparticles to settle to the bottom, and allowed the separation of soluble graphene nanoparticles in the supernatant. The supernatant solutions were also checked for the presence of any free $Mn^2$ ions. This was achieved by first flocculating the graphene nanoparticles with HCl, and then testing the clear solution with sodium bismuthate ($NaBiO_3$) in $HNO_3$. In this reaction, manganese is oxidized from the +2 oxidation state ($Mn^{+2}$) to the +7 oxidation state ($MnO_4$) which has distinctive purple or pink color. No such color change was observed indicating that no free $Mn^{2+}$ ions were present in the supernatant solution.

The supernatants solutions containing the soluble graphene nanoparticles were used for relaxometry measurements. The longitudinal and transverse relaxation times ($T_1$, $T_2$) were measured at 20 MHz (0.47T) on a Minispec NMR spectrometer (Bruker Instruments, Woodland, Tex.). Each sample was prepared at five known concentrations by serial dilution. The temperature was maintained at 40° C. during the measurements. $T_1$ and $T_2$ relaxation times of each experimental sample and the control (1% Pluronic 127 solution) were measured using inversion recovery, and CPMG methods, respectively. The inverse of the relaxation times represent the respective relaxation rates, $R_1$ and $R_2$. A plot of relaxation rate (y-axis) versus concentration (x-axis) was created, and was fit to a linear curve. The slope of this linear fit gave the value of relaxivity. Single point relaxivity ($r_1$) was obtained during NMRD measurements. The relaxivity values ($r_1$), were calculated using the formula $r_1=(R_1-R_0)/[Mn^{2+}]$; where $R_{1,2}$ and $R_0$ are the longitudinal or transverse relaxation rates of the samples, and 1% Pluronic F127 surfactant solution respectively, and [$Mn^{2+}$] is the concentration of Manganese in the volume of solution used for relaxation measurements. The $1/T_1$ NMR dispersion (NMRD) profiles at magnetic fields corresponding to a proton Larmor frequency range 0.01-40 MHz were obtained using a fast field cycling relaxometer (SPINMASTER FFC2000, Stelar Inc, Pavia, Italy). A High Field Superconducting Dipole (HTS) electromagnet was used to acquire the relaxation data from 25 to 80 MHz range of proton Larmor frequency. The temperature was fixed to 27° C., and was controlled by a Stelar VTC-91 airflow heater, equipped with a copper-constantan thermocouple; the temperature calibration in the probe head was done with a Delta OHM digital thermometer, with an absolute accuracy of 0.5° C.

Figure 9A:
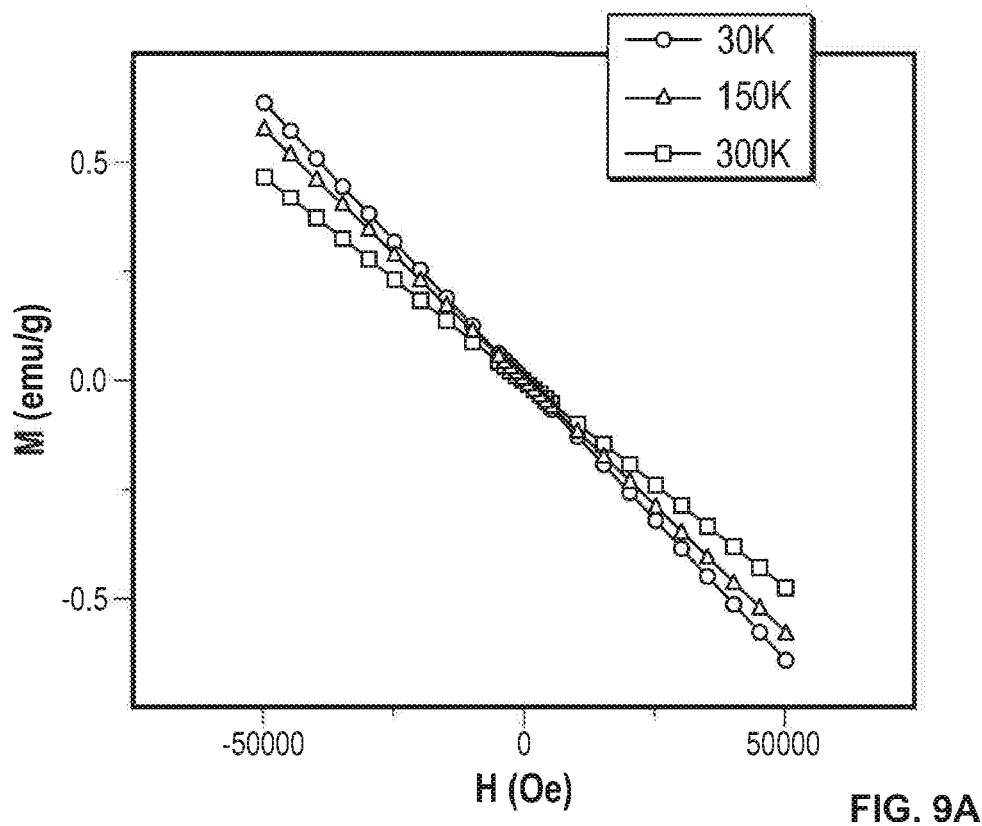
FIGS. 9(a)-9(e).: Plot of Magnetization (M) v/s Field strength (H) for (a) micro-graphite, (b) oxidized graphite (c) Oxidized Graphene nanoplatelets (d) Reduced Graphene nanoplatelets at 30K, 150 and 300K between −50,000 to 50,000 Oe (Inset shows plot between −5000 and 5000 Oe at 300K), (e) ZFC and FC magnetization plots of reduced graphene nanoplatelets.
Figure 9B:
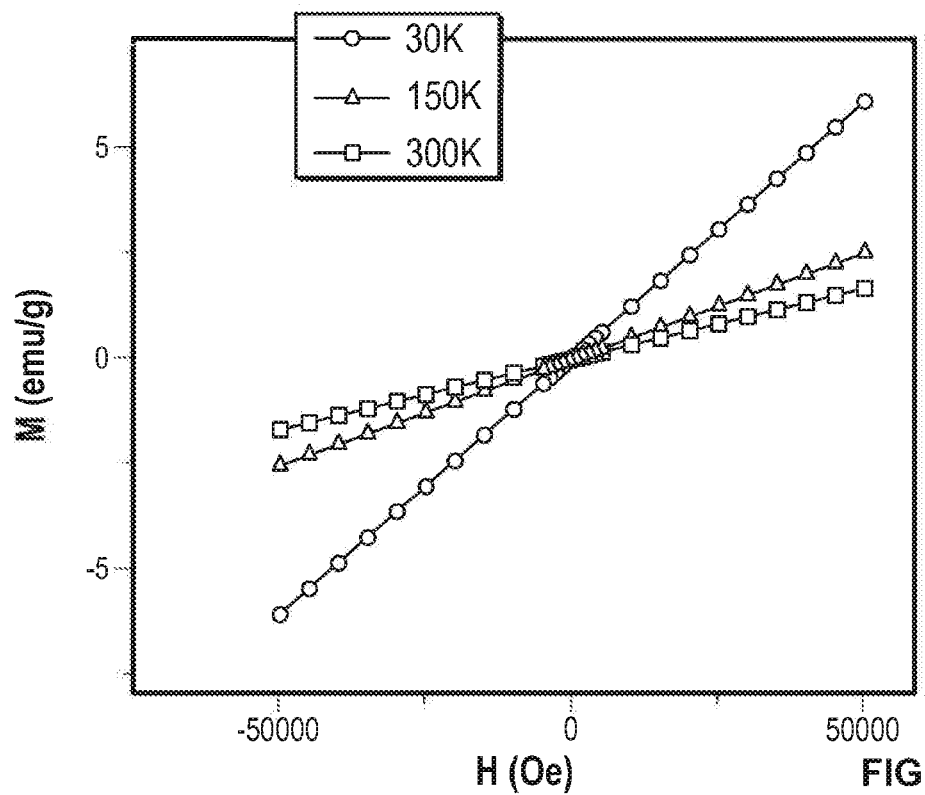
Figure 9C:
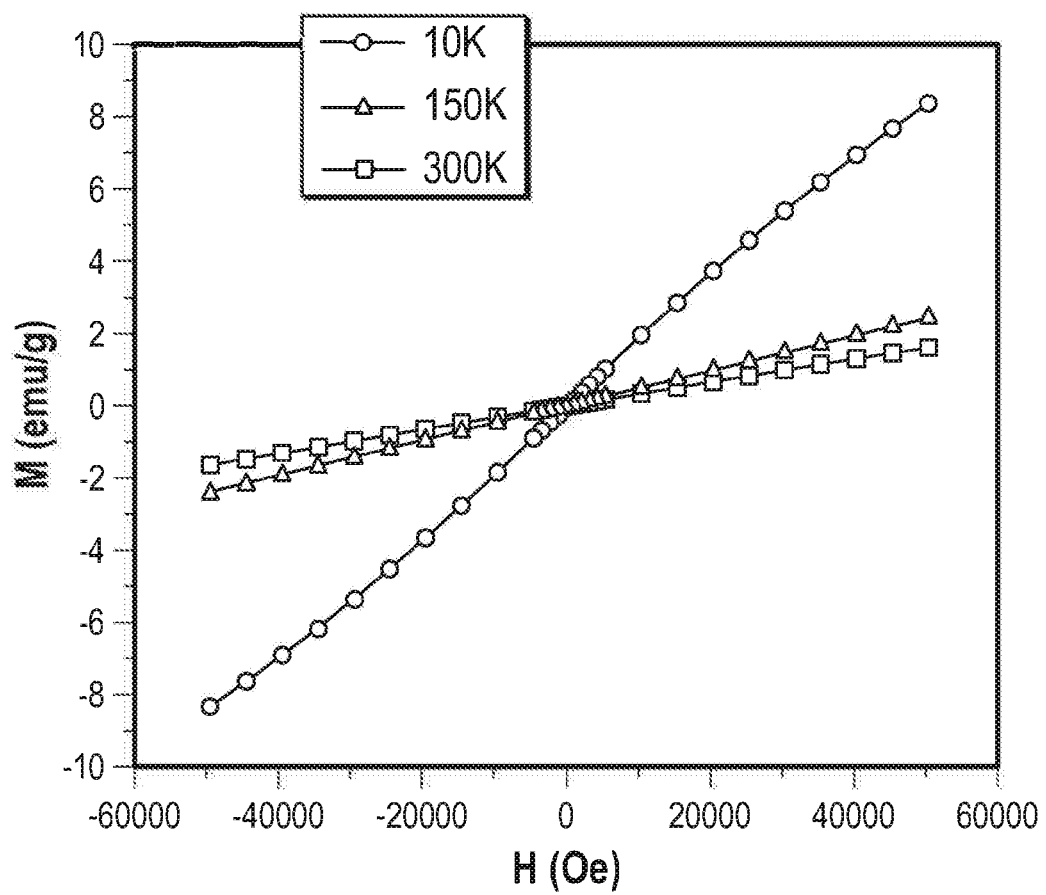
Figure 9D:
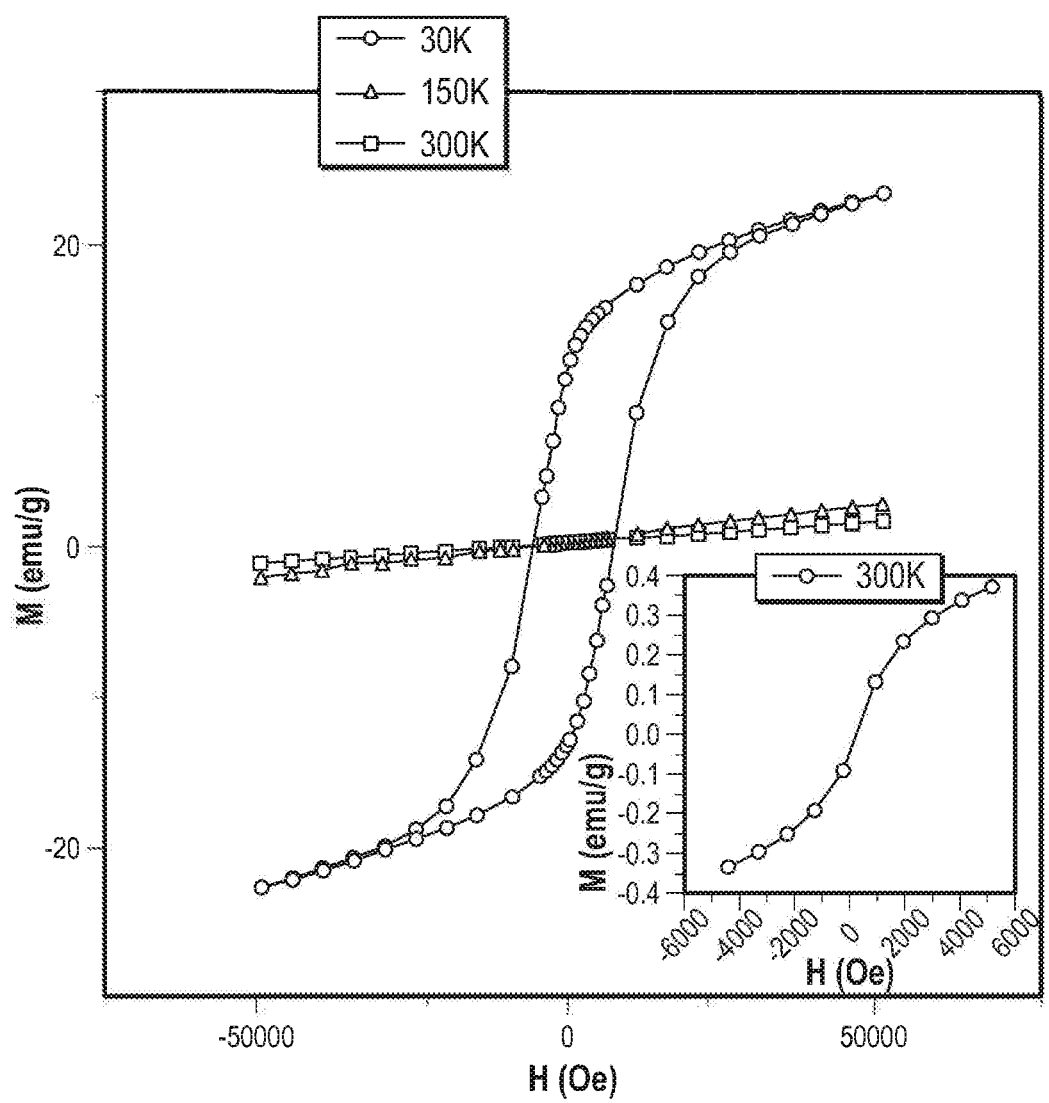
Figure 9E:
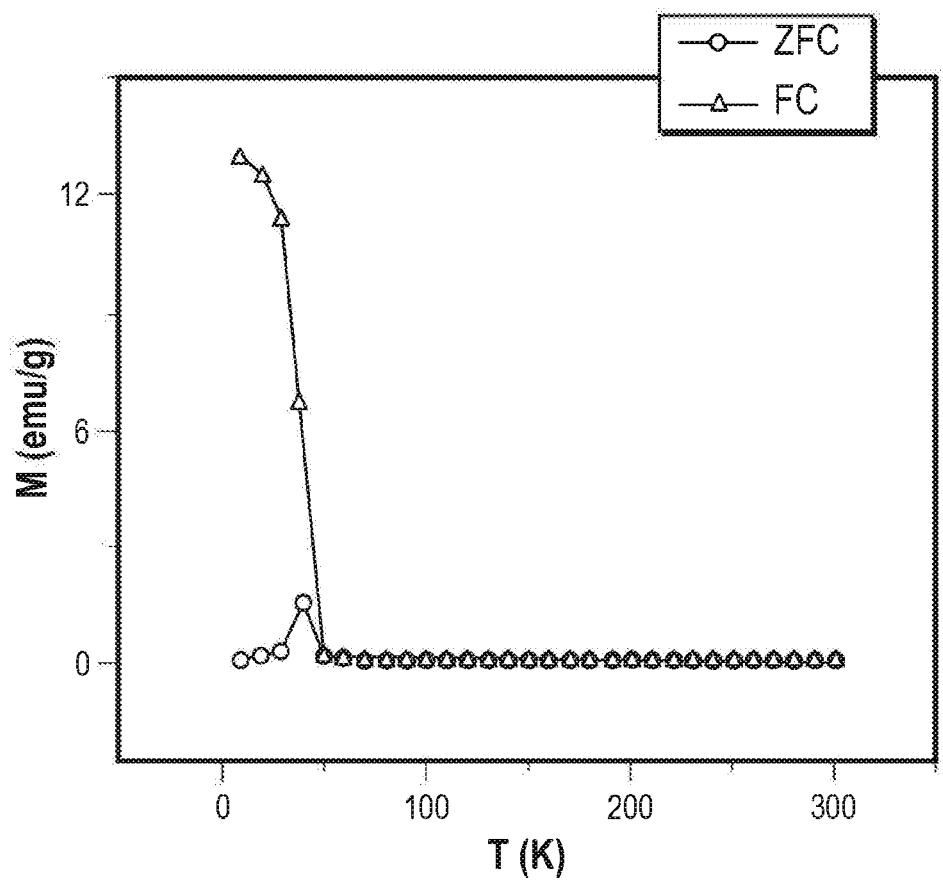

Results and Discussion:

FIGS. 9(a)-9(e) shows the SQUID magnetic characterization of oxidized graphite, oxidized graphene nanoplatelets and reduced graphene nanoplatelets. Analytical grade micro-graphite used as the starting material for the preparation of these particles was the control in these experiments. FIG. 9a shows the plot of magnetization (M) versus magnetic field strength (H) for the analytical grade micrographite (control) between −50,000 Oe and 50,000 Oe for three temperatures (30K, 150K, and 300K). The negative slope indicates a decrease in the value of magnetic moments with increase in applied magnetic field, which is characteristic of diamagnetic behavior. FIGS. 9b and 9c show the M versus H plot for oxidized graphite and oxidized graphene nanoplatelets, respectively. The plots show a linear increase in the value of the magnetic moments with field strength indicating paramagnetic behavior for both oxidized graphite and oxidized graphene nanoplatelets. The change to paramagnetism upon oxidation of graphite can be attributed to the presence of the paramagnetic $Mn^{2+}$ ions present in the sample. FIG. 9d shows the M versus H plot of reduced graphene nanoplatelets. The plot displays a ferromagnetic hysteresis curve at the lower temperature (30K) indicating superparamagnetic behavior (inset of FIG. 9d) at room temperature (300K). Room temperature superparamagnetism has been widely reported in nanoparticle clusters (<30 nm) (Whitney et al., 1993, Science 261: 1316; and Wang et al., 2004, Advanced Materials 16: 137-140), and is a size dependent phenomenon, wherein, the thermal energy of the nanoparticle is sufficient to allow flips in the magnetic spin direction, and insufficient to overcome the spin-spin exchange coupling energy. As a result, in the absence of a magnetic field, the net magnetization measured is zero, and the M versus H curve assumes an 'S' shape instead of a hysteresis loop. The zero field cooling (ZFC) and field cooling (FC) curves for the reduced graphene nanoplatelets at uniform field strength of 500 Oe and between 10K and 300K are shown in FIG. 9e. The peak in the ZFC curve reveals a blocking temperature ($T_B$) of 40K indicating a transition between ferromagnetic and superparamagnetic states. The remnant magnetization of the hysteresis curve at 30K is 12.47 emu/g and the coercivity is 6298.68 Oe and could be attributed to the single domain nature, and high shape anisotropy of the sample (Du et al., 2006, Nanotechnology 17: 4923). The results for reduced graphene nanoplatelets exhibit sharp resemblance with that of hausmannite (Du et al., 2006, Nanotechnology 17: 4923). Room temperature magnetism has been reported in carbon nanomaterials such as fullerenes, carbon nanotubes, carbon nanofoams, graphene, nanodiamonds and graphite (Makarova, 2004, Semiconductors 38: 615-638, Wang, et al., 2008, Nano Letters 9: 220-224, and Esquinazi et al., 2002, Physical Review B 66: 024429). The magnetic characteristic of these materials include spin-glass-like paramagnetic or ferromagnetic behavior attributed either to the presence of metal impurities or presence of defects in the graphite lattice structure. In case of the oxidized graphite, oxidized graphene nanoplatelets and reduced graphene nanoplatelets, the defects created in graphitic lattice structure during the oxidation or exfoliation process may contribute to the observed magnetic behavior. However, theoretical and experimental studies show the defects in graphitic structures induce very weak magnetic behavior with saturation magnetic moment values of approximately $10^{-3}$-$10^{-6}$ emu/g (Zhou et al., 2010, Thin Solid Films 519: 1989-1992. Thus, the observed magnetic behavior reported above should be mainly due to the presence of manganese.

Figure 10A:
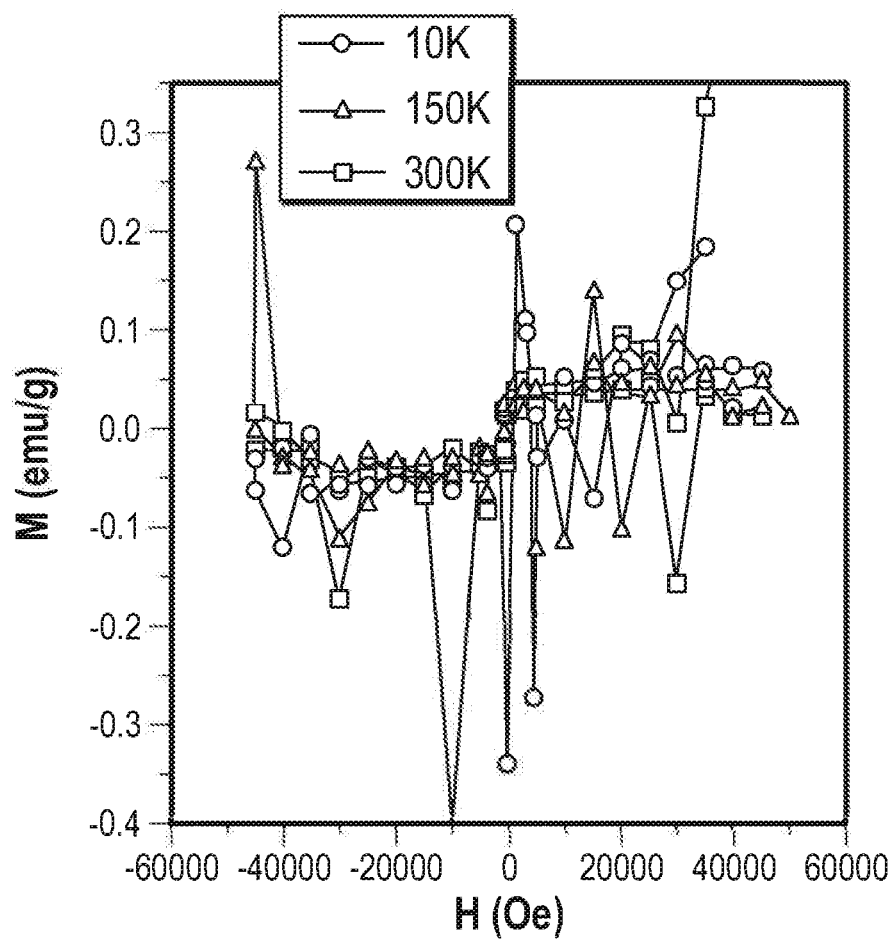
FIGS. 10(a)-10(c): Magnetization (M) v/s Field strength (H) between −50,000 Oe and 50,000 Oe at 10, 150 and 300K for (a) MWCNTs, and (b) graphene nanoribbons (Inset shows M versus H between −4000 Oe and 4000 Oe at 300K), (c) ZFC and FC plots of graphene nanoribbons.
Figure 10B:
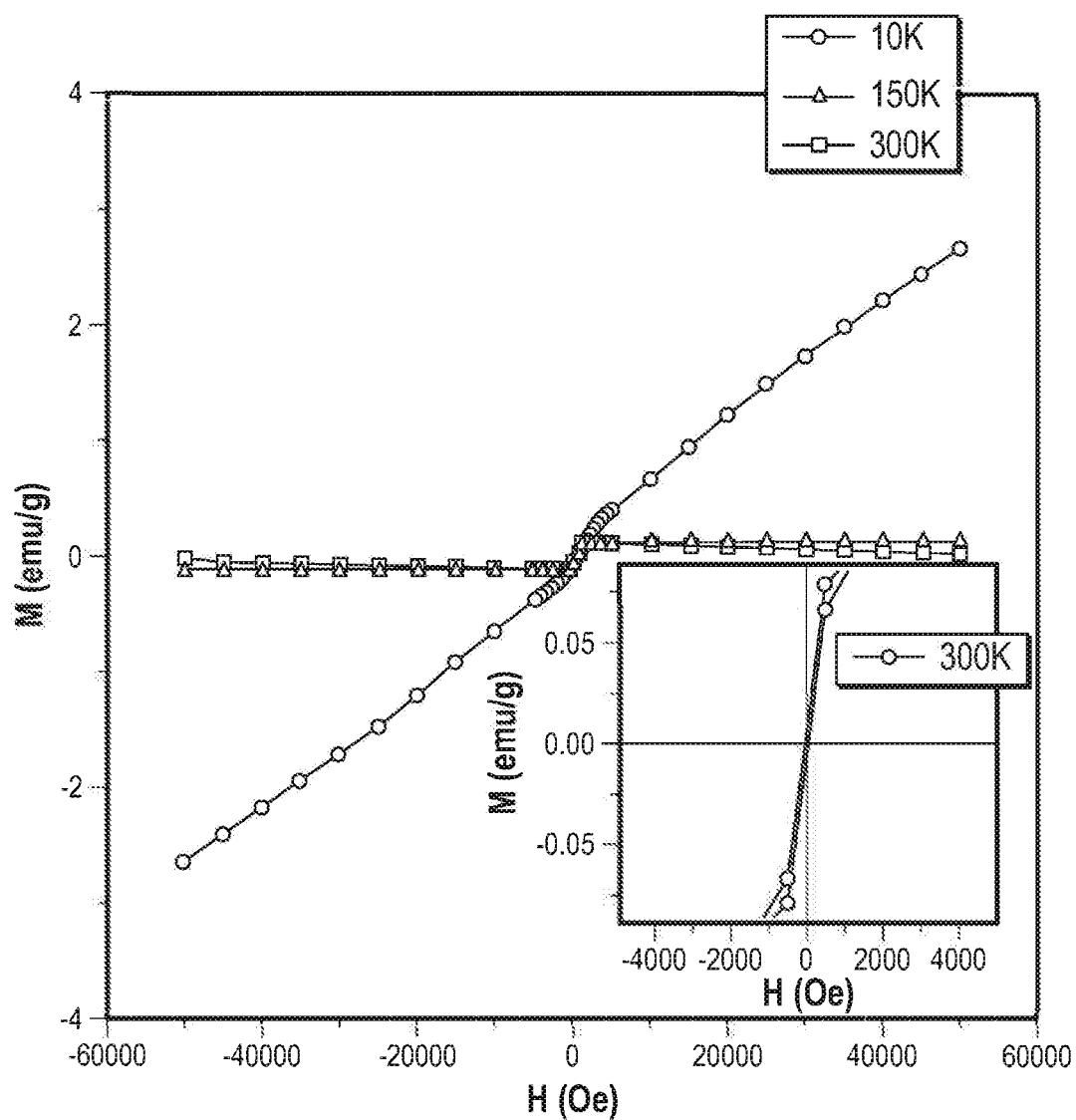
Figure 10C:
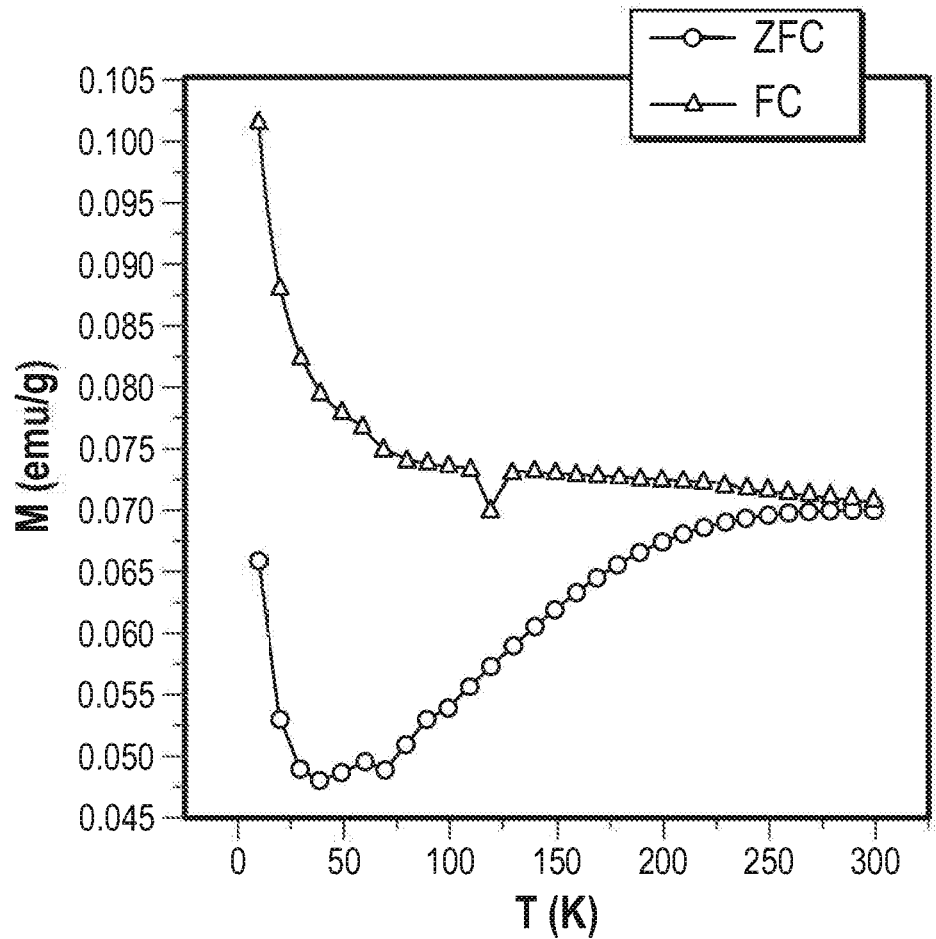
Figure 11A:
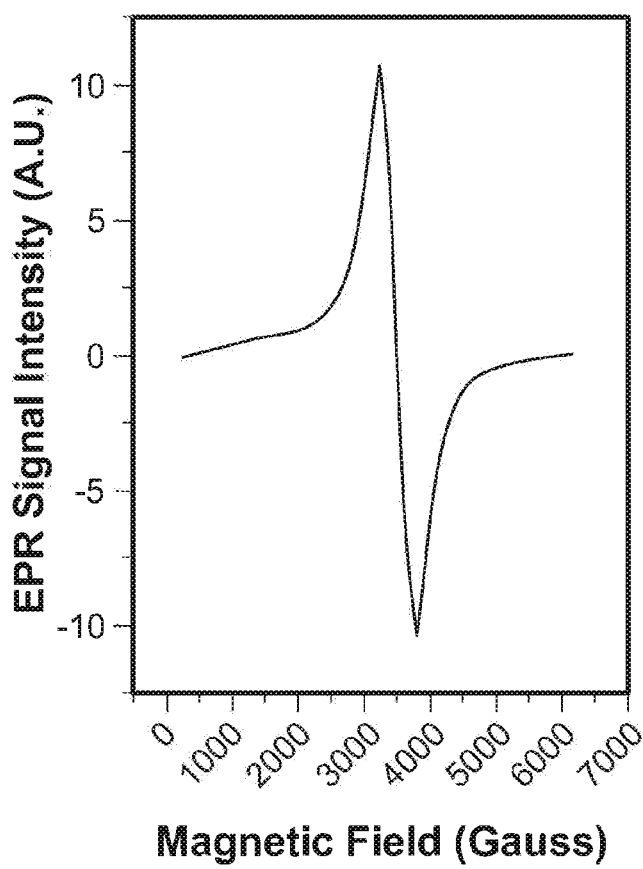
FIGS. 11(a)-11(d): Room temperature EPR spectra of solid (a) oxidized micro-graphite, (b) oxidized graphene nanoplatelets, (c) reduced graphene nanoplatelets and (d) graphene nanoribbons.
Figure 11B:
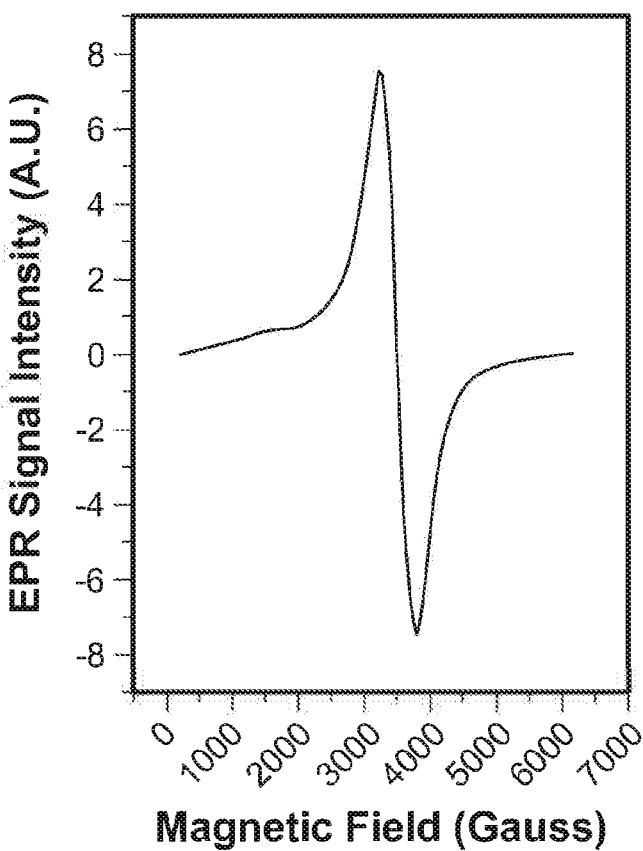
Figure 11C:
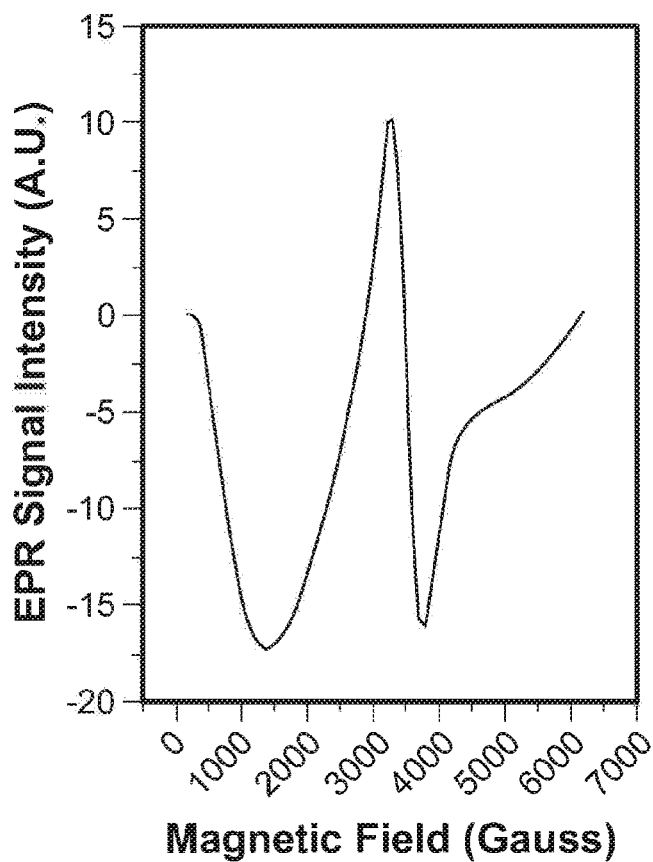
Figure 11D:
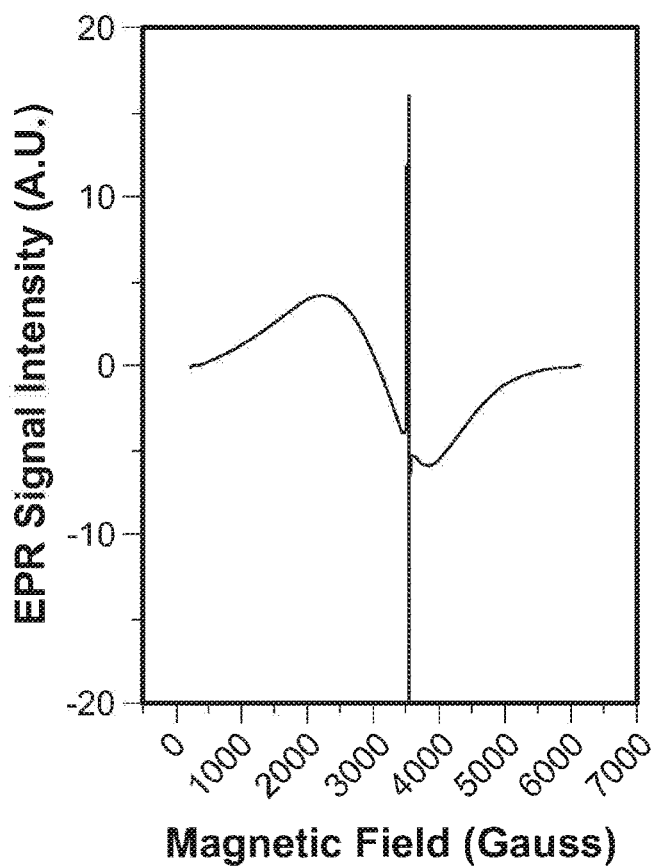
Figure 12A:
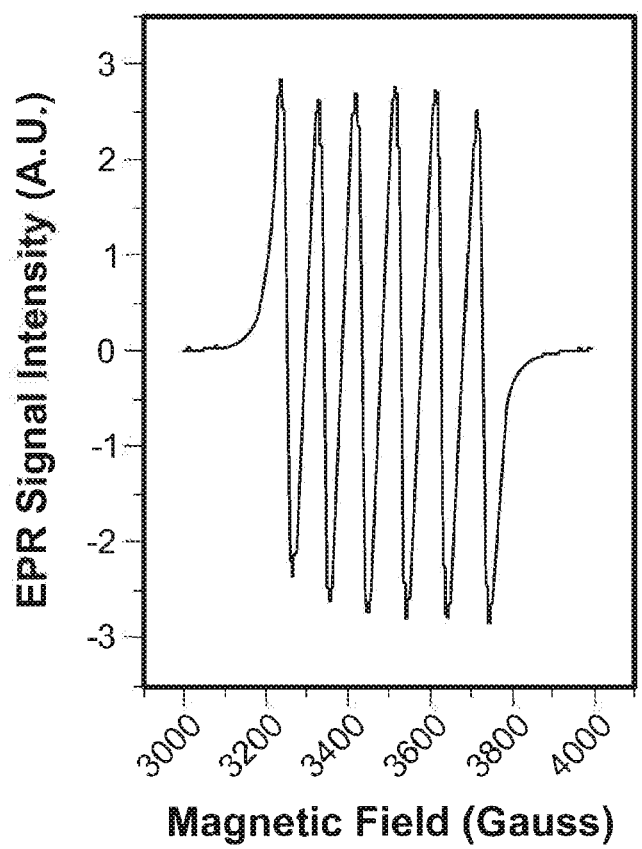
FIGS. 12(a)-12(d): Room temperature EPR spectra of aqueous solutions of (a) oxidized micro-graphite, (b) oxidized graphene nanoplatelets, (c) reduced graphene nanoplatelets and (d) graphene nanoribbons.
Figure 12B:
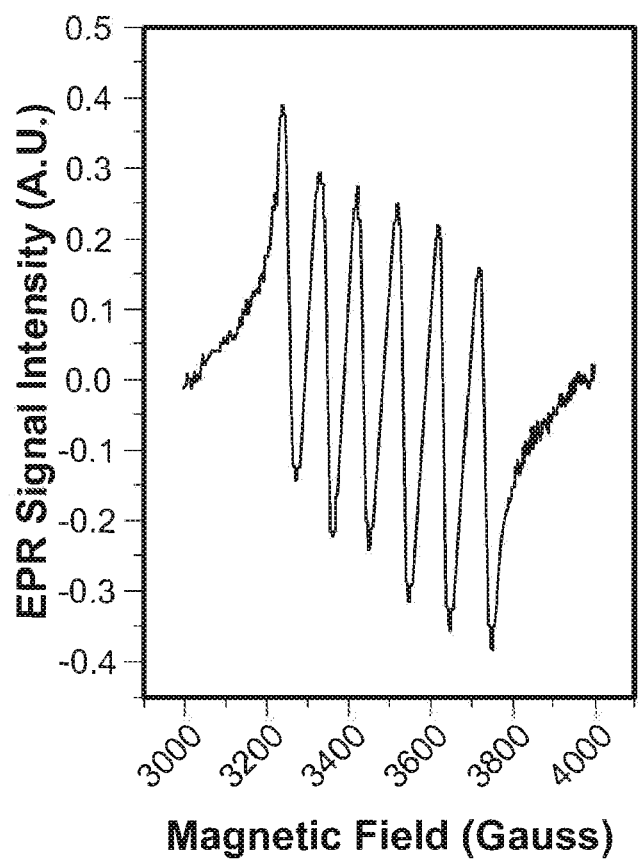
Figure 12C:
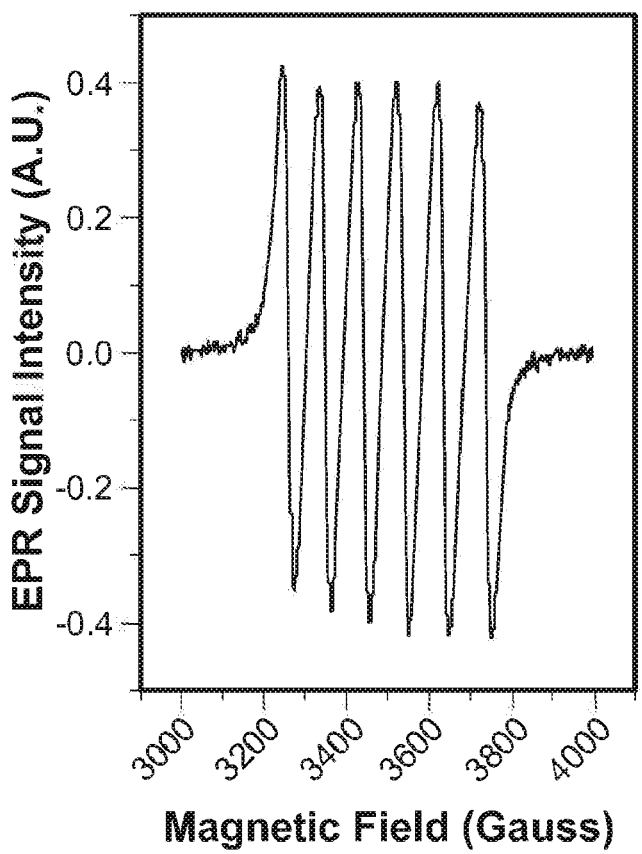
Figure 12D:
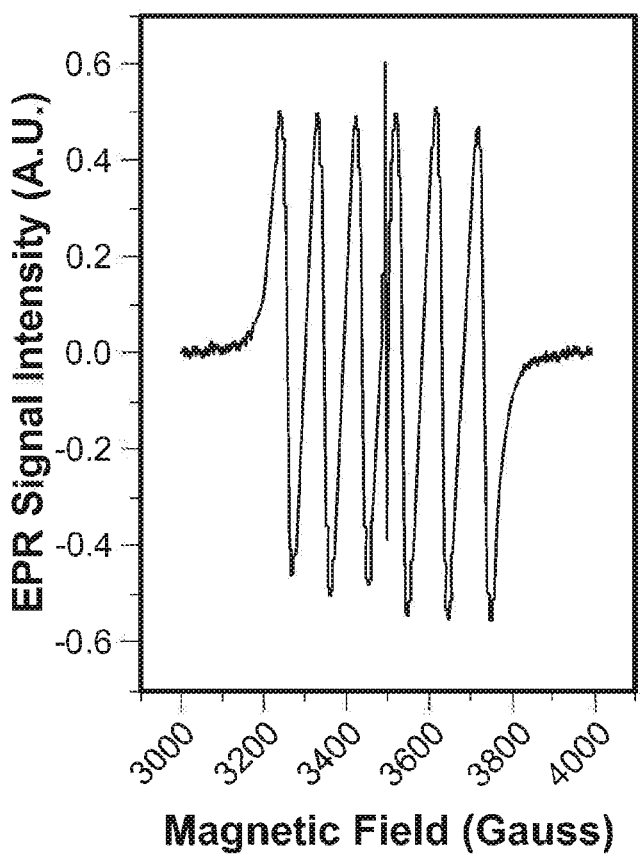
Figure 13A:
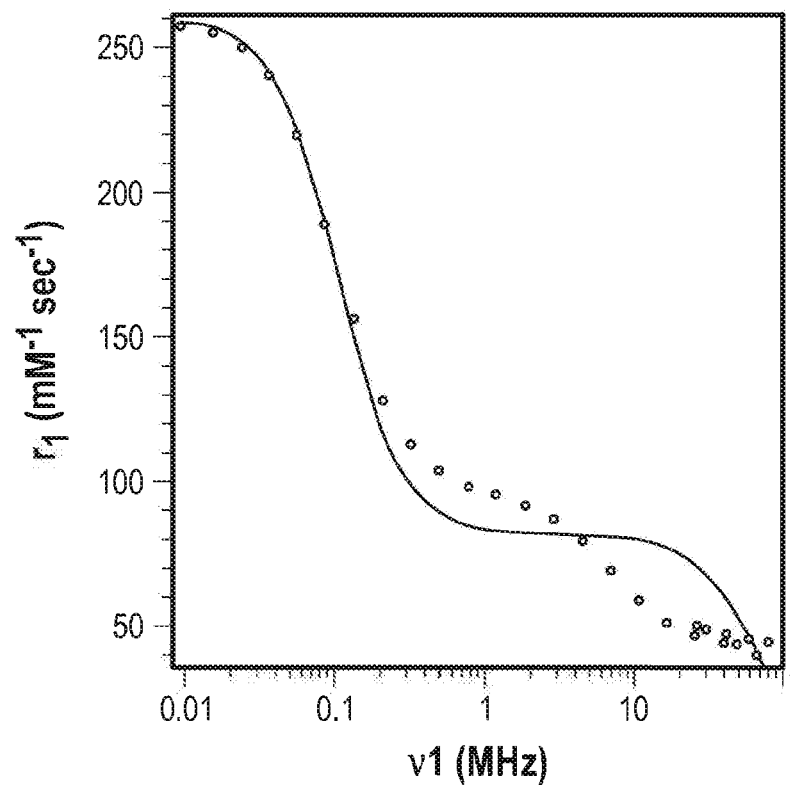
FIGS. 13(a)-13(d): Experimental NMRD profiles (dots), and best fits (solid lines) derived from SBM Theory for (a) Oxidized Graphite, (b) Graphene Nanoplatelets, (c) Reduced Graphene Nanoplatelets, and d) Graphene Nanoribbons.
Figure 13B:
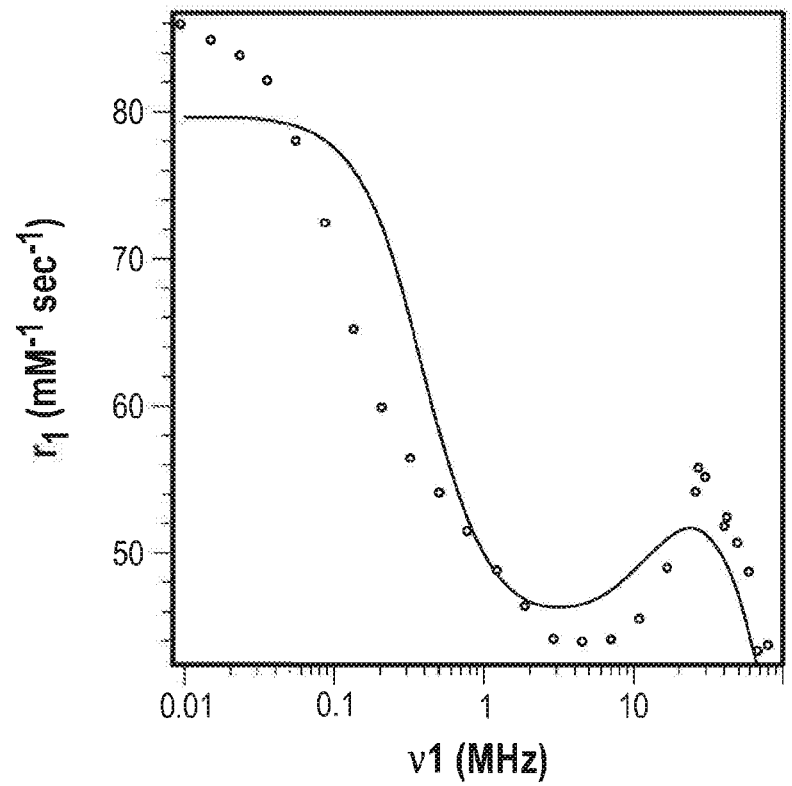
Figure 13C:
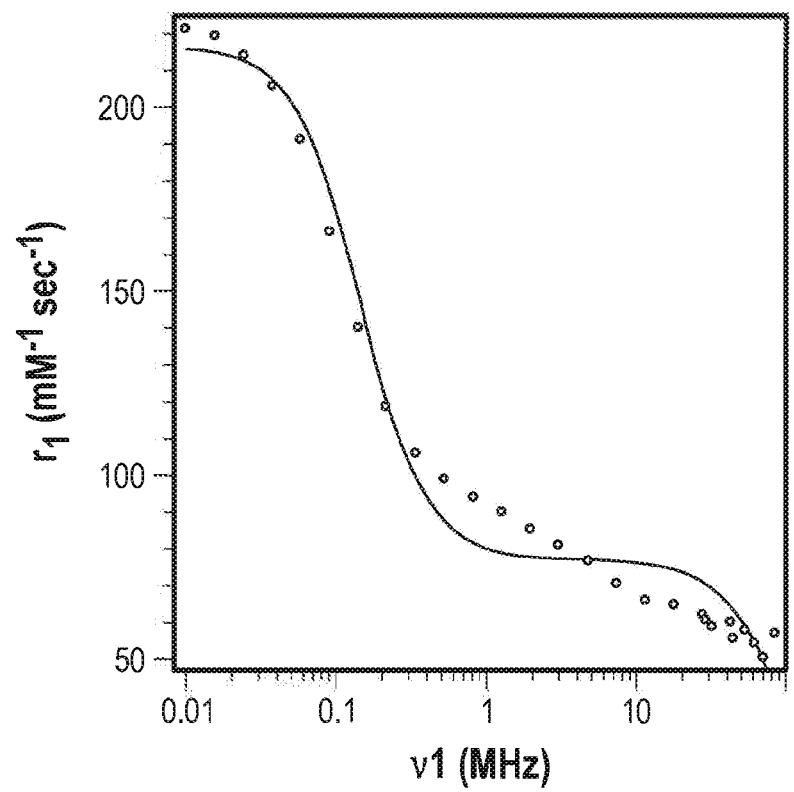
Figure 13D:
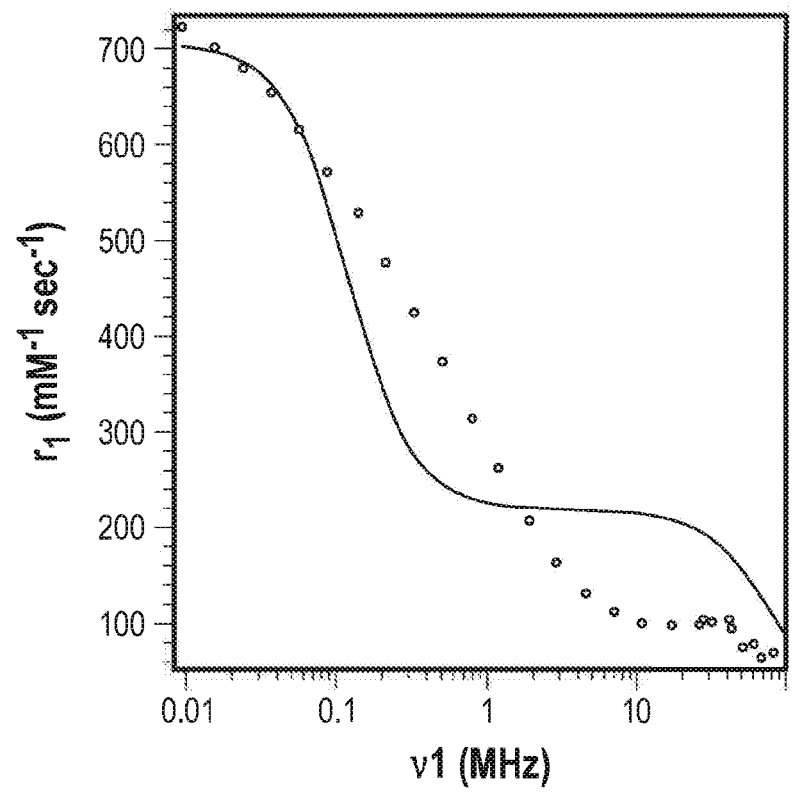

FIGS. 10(a)-10(c) shows the SQUID magnetic characterization of MWCNTs (control), and graphene nanoribbons. FIG. 10a shows the plot of magnetization (M) versus magnetic field strength (H) for the MWCNTs between −50,000 Oe and 50,000 Oe for three temperatures (10K, 150K, and 300K). The plots show no coherent magnetic pattern, and the magnetic signals are extremely weak at all three temperatures indicating diamagnetic behavior despite the presence of iron catalysts in the MWCNTs.

FIG. 10b displays the plot of M versus H for graphene nanoribbons between −50,000 Oe and 50,000 Oe for three temperatures (10K, 150K, and 300K). Even though, the M versus H curve seems to assume an 'S' shape instead of a hysteresis loop, closer analysis of the curve (see inset in FIG. 10b) indicates ferromagnetic behavior with a very low remanence. The SQUID analysis indicates ferromagnetism at 30K, 150 K and 300K. Closer analysis shows interesting magnetic properties at room temperature. The temperature dependence of the magnetization at zero-field cooled (ZFC) as well as field cooled (FC) conditions is plotted in FIG. 10c at magnetic field strength 500 Oe (temperature range 10-300 K). It is clear from the graph that all the graphene nanoribbons show ferromagnetic behavior at low temperatures, and show bifurcation of the ZFC and FC branches. The temperature at which the FC and ZFC curves bifurcate (also referred as the irreversibility temperature), as well as the blocking temperature ($T_B$) is 300 K. FIG. 10c indicates FC/ZFC plots, and a maximum value on the ZFC curve is seen at a value >300K, which is greater than room temperature. The ZFC magnetization curves show a broad maximum below the bifurcation temperature. The bifurcating FC and ZFC curves indicate thermodynamic irreversibility, and could have its origin in the effects like strong competing interaction between ferromagnetic and anti-ferromagnetic phases, and phase separations at a nanoscale due to the occurrence of a low temperature spin-glass-like state or a mixed phase (Zhou et al., 2010, Thin Solid Films 519: 1989-1992; Bie et al, 2010, Solid State Sciences 12: 1364-1367; Raley et al., 2006, Journal of alloys and compounds 423: 184-187). The saturation magnetization seen at 300K is 0.1 emu/g at 2500 Oe. The sample shows a coercive field of 250 Oe at 10 K. The magnetism results clearly indicate that the graphene nanoribbons exhibit room-temperature weak ferromagnetism. The elemental analysis of graphene nanoribbons showed that apart from manganese, trace amounts of iron (0.005 wt % or 50 μg Fe per gram) was also present in these samples. The MWCNTs used in the preparation of the graphene nanoribbons do not show any magnetic behavior even though they contain iron nanoparticles as catalyst (0.1 wt %) (Sigma-Aldrich I Certificate of Analysis-MW-CNT) which is 20 times greater than the amount found in graphene nanoribbons. Furthermore, it has been reported that presence of Fe or $Fe_3O_4$ clusters with Fe concentration of 1-500 µg Fe per gram (1 ppm) graphite contribute $2.2\times10^{-5}$ to $4\times10^{-3}$ emu/g to the magnetization (Esquinazi et al., 2002, Physical Review B 66: 024429). The above information taken together suggests that the presence of trace amounts of iron does not contribute significantly to the observed magnetic behavior of the graphene nanoribbons. Several recent studies show that point defects of oxygen vacancies in metal oxide nanostructures could result in weak ferromagnetism (Schoenhalz et al., 2009, Applied Physics Letters 94: 162503; and Kundaliya et al., 2004, Nature materials 3: 709-714), and similar defect in the manganese oxide due to its interactions with the graphene nanoribbons could be responsible for observed magnetic behavior. However, more studies are needed to confirm this hypothesis.

FIGS. 11(a)-11(d) show the EPR spectra of the oxidized micro-graphite, oxidized graphene nanoplatelets, reduced graphene nanoplatelets and graphene nanoribbons, respectively (the blank EPR spectrum of the quartz EPR tube and DPPH standard is shown in FIGS. 17A-17D). The g values, EPR line widths at half heights ($\Delta H_{1/2}$, Gauss) and electron relaxation time ($T_{2e}$) of each EPR spectra are listed in Table 3a. All samples show broad peak ($\Delta H_{1/2}$) at their respective g values. However, graphene nanoribbons show $\Delta H_{1/2}$ values 2.6 times greater than oxidized micrographite, oxidized graphene nanoplatelets and reduced graphene nanoplatelets, which have similar $\Delta H_{1/2}$ values. The large line width indicates short electron relaxation time ($T_{2e}$), and the calculated $T_{2e}$ values were between 0.19-21 nanoseconds for oxidized micrographite, oxidized graphene nanoplatelets, and reduced graphene nanoplatelets. Graphene nanoribbons have $T_{2e}$ values 0.072 nanoseconds; at least 2.9 times shorter than the other compounds. The EPR spectra of the graphene nanoribbons samples also shows a narrow peak in the center, which indicates presence of free radical species, possibly due to defect centers in the nanoribbon structures as reported (Rao et al., 2011, New J Phys 13: 113004). The free radical species have g of 2.007, and line width of 1.2 Gauss, and thus have very long electron relaxation time ($T_{2e}$) of 88.2 nanoseconds. The large line broadening in all the compounds indicates significant manganese-to-manganese dipolar interaction. A reduction in the amount of manganese in the sample should decrease the line broadening, and resolve the 6-line manganese hyperfine structure in the EPR spectrum, and consequently, decrease the electron relaxation time.

Figure 17A:
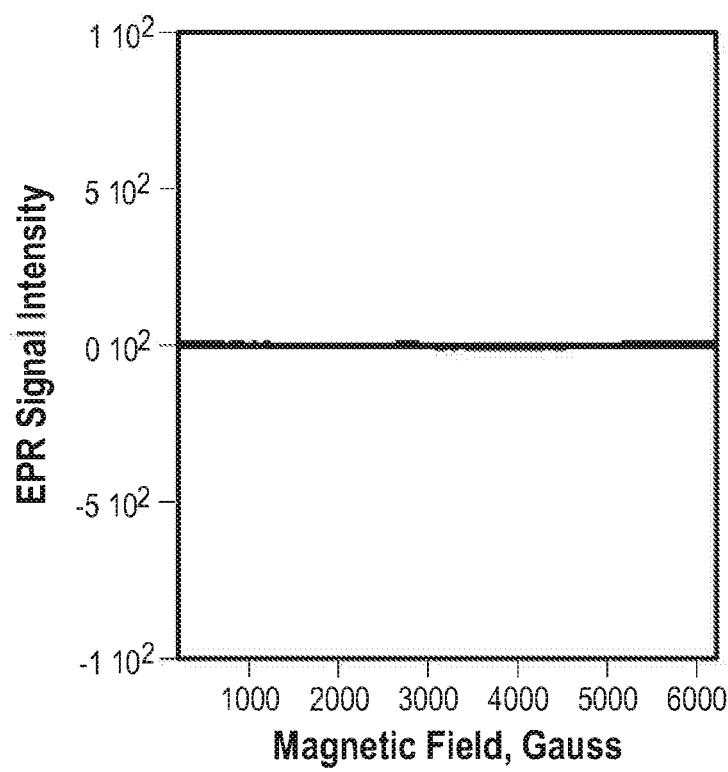
FIGS. 17(a)-17(d): EPR spectrum of the (a) Wilmad quartz EPR tubes used for the measurement of the solid samples, (b) quartz EPR flat tube used for the aqueous samples, (c) DPPH standard (solid) and (d) DPPH standard (aqueous).
Figure 17B:
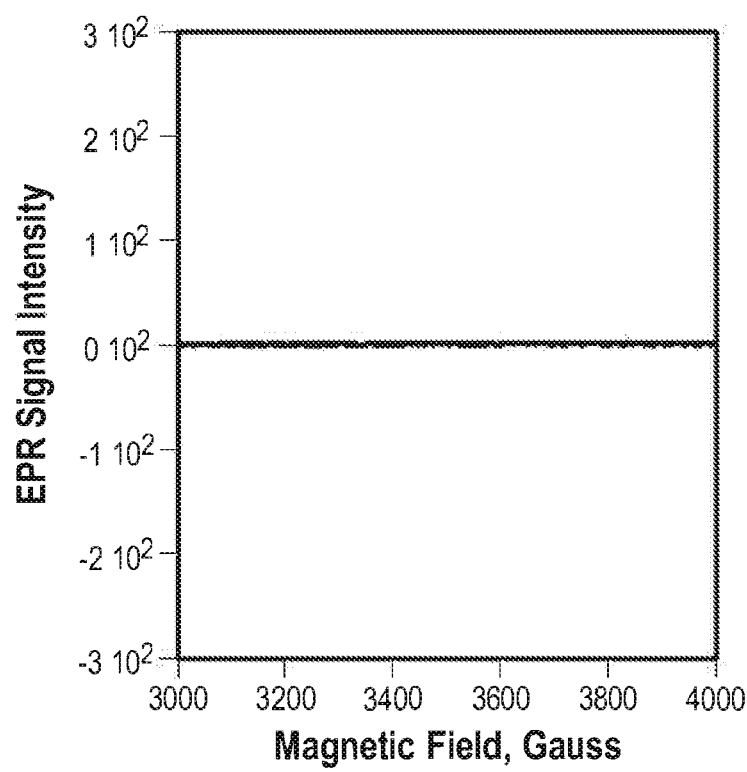
Figure 17C:
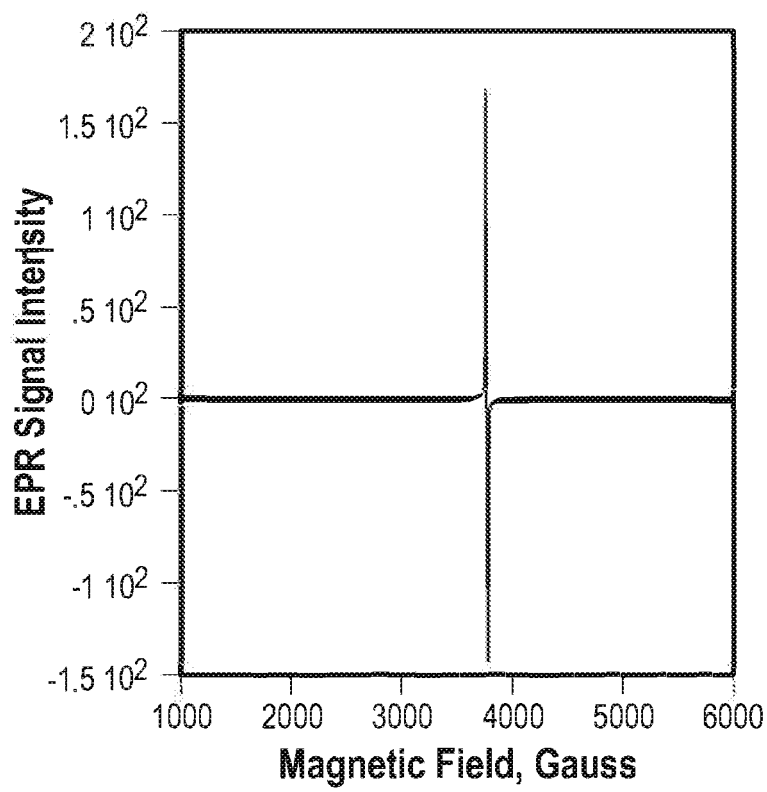
Figure 17D:
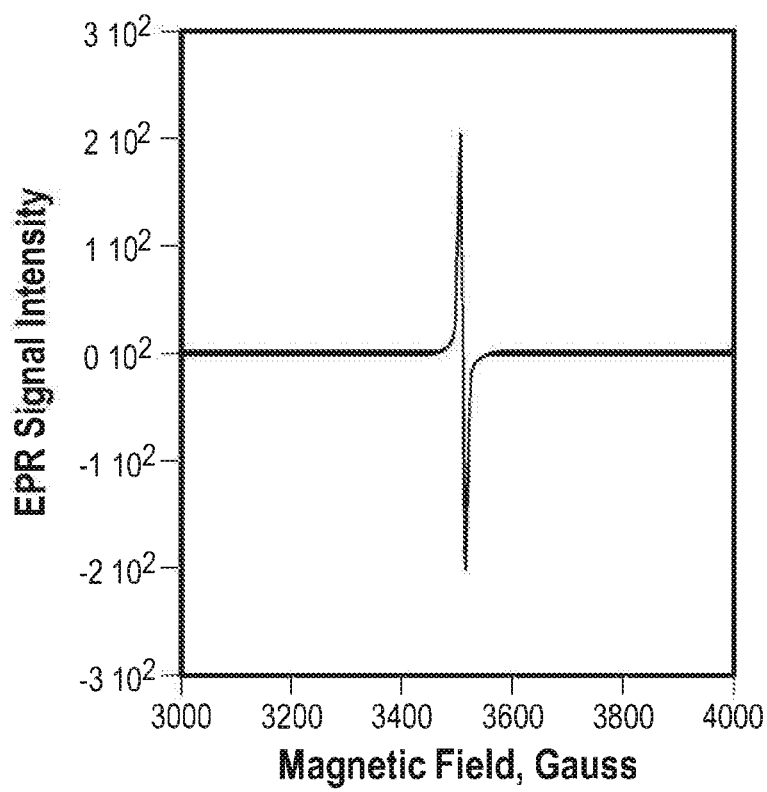
Figure 18A:
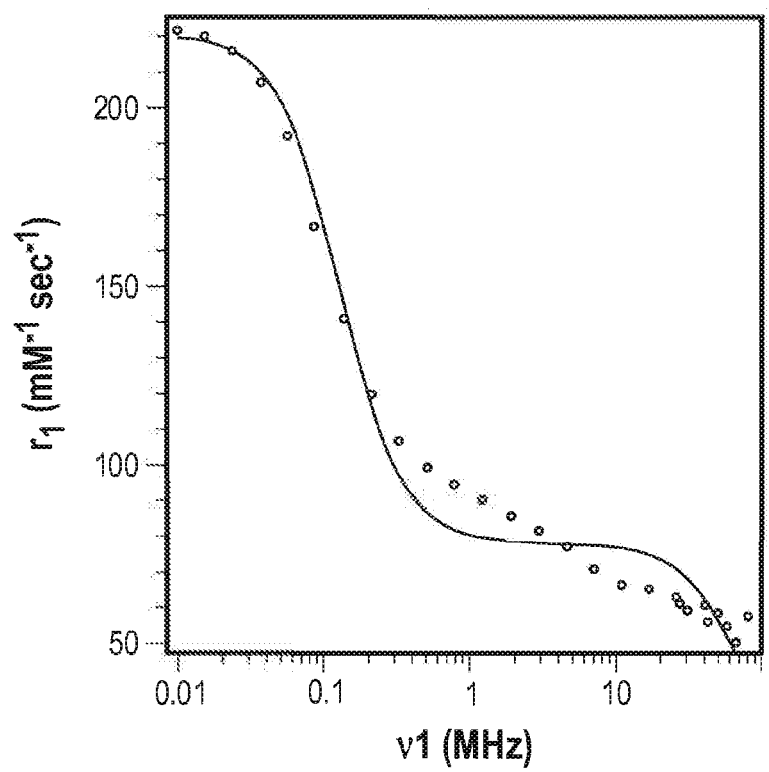
FIGS. 18(a)-18(d): Curves obtained for floating all SBM parameters to float. A) Oxidized Graphite, B) Oxidized Graphene Nanoplatelets, C) Reduced Graphene Nanoplatelets, D) Graphene Nanoribbons.
Figure 18B:
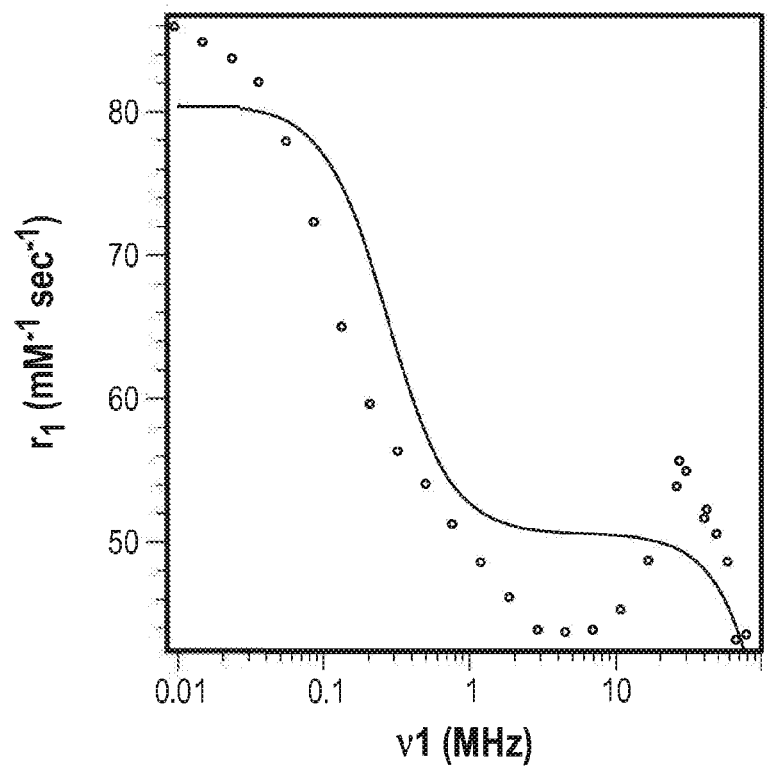
Figure 18C:
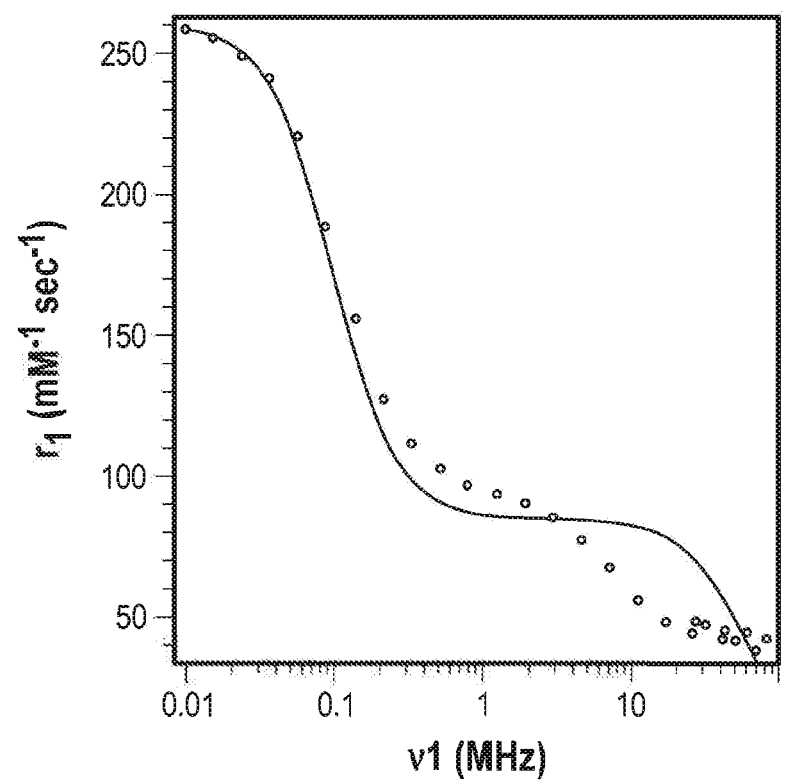
Figure 18D:
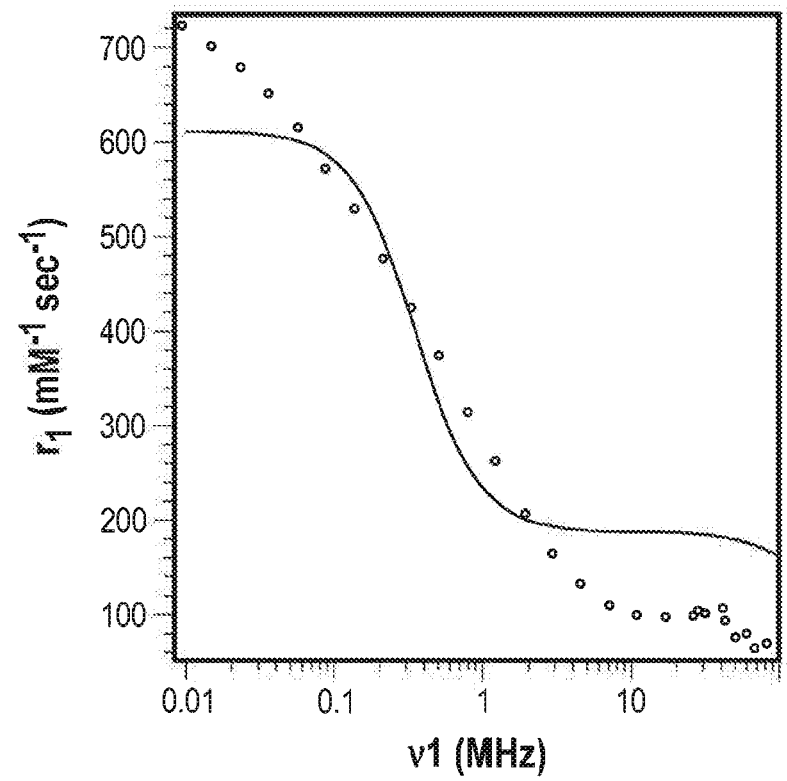
Figure 19A:
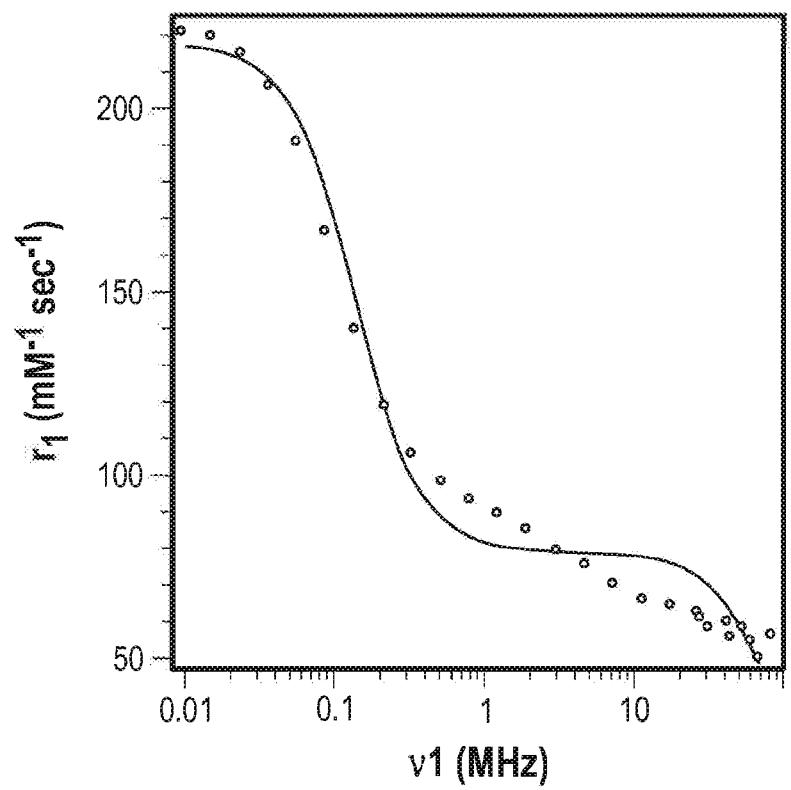
FIGS. 19(a)-19(d): Curves obtained for fixed Q=2 with remaining SBM parameters allowed to float. A) Oxidized Graphite, B) Oxidized Graphene Nanoplatelets, C) Reduced Graphene Nanoplatelets, D) Graphene Nanoribbons.
Figure 19B:
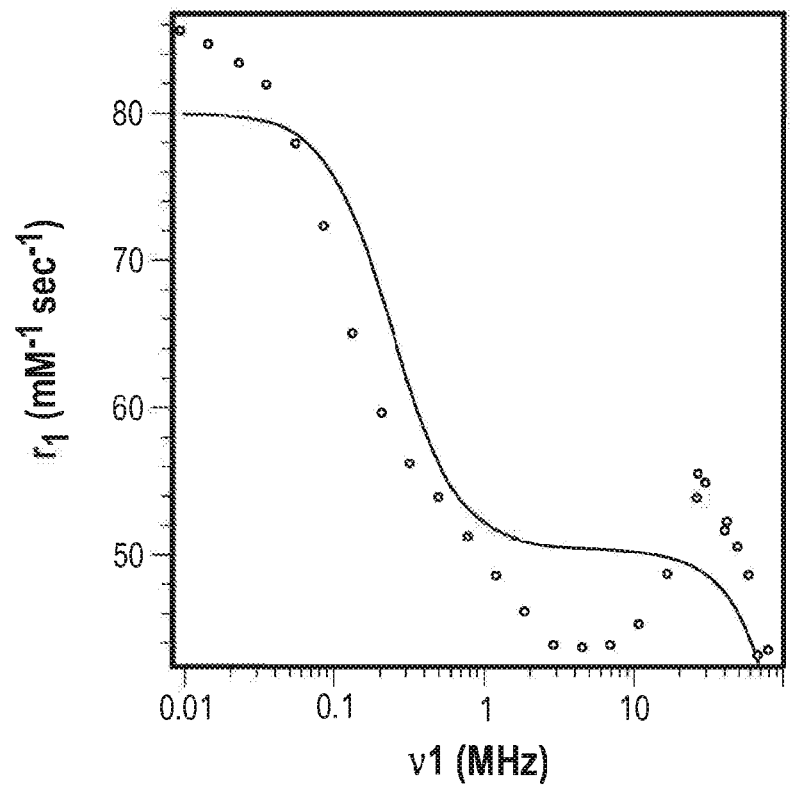
Figure 19C:
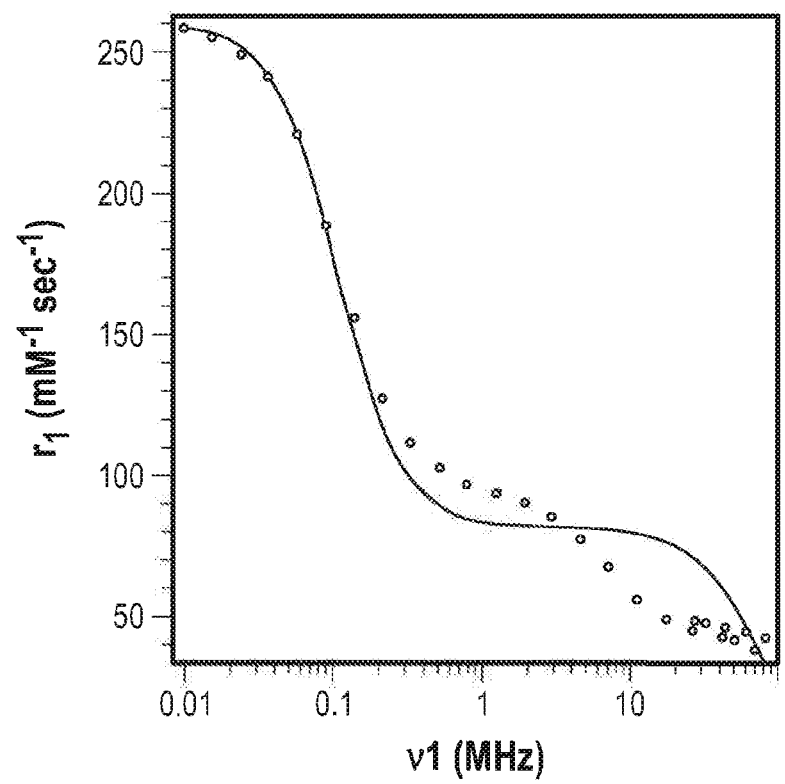
Figure 19D:
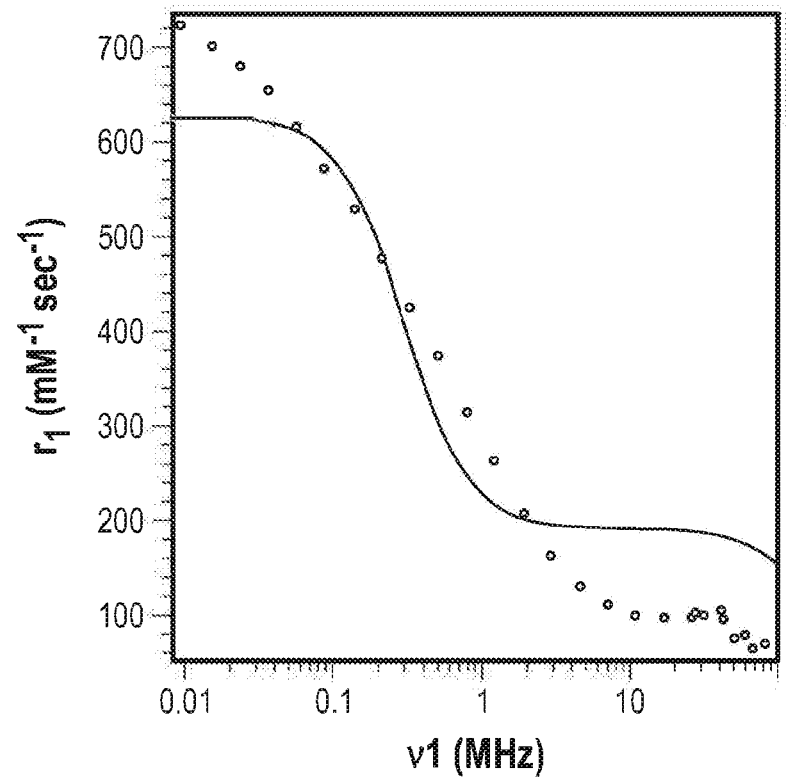
Figure 20A:
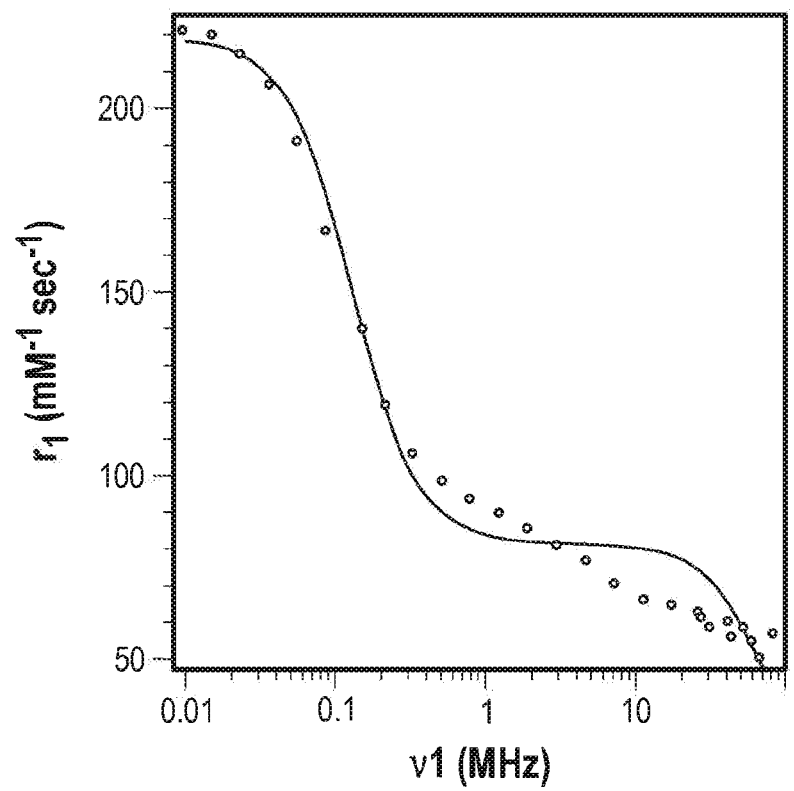
FIGS. 20(a)-20(d): Curves obtained for fixed Q=4 with remaining SBM parameters allowed to float. A) Oxidized Graphite, B) Oxidized Graphene Nanoplatelets, C) Reduced Graphene Nanoplatelets, D) Graphene Nanoribbons.
Figure 20B:
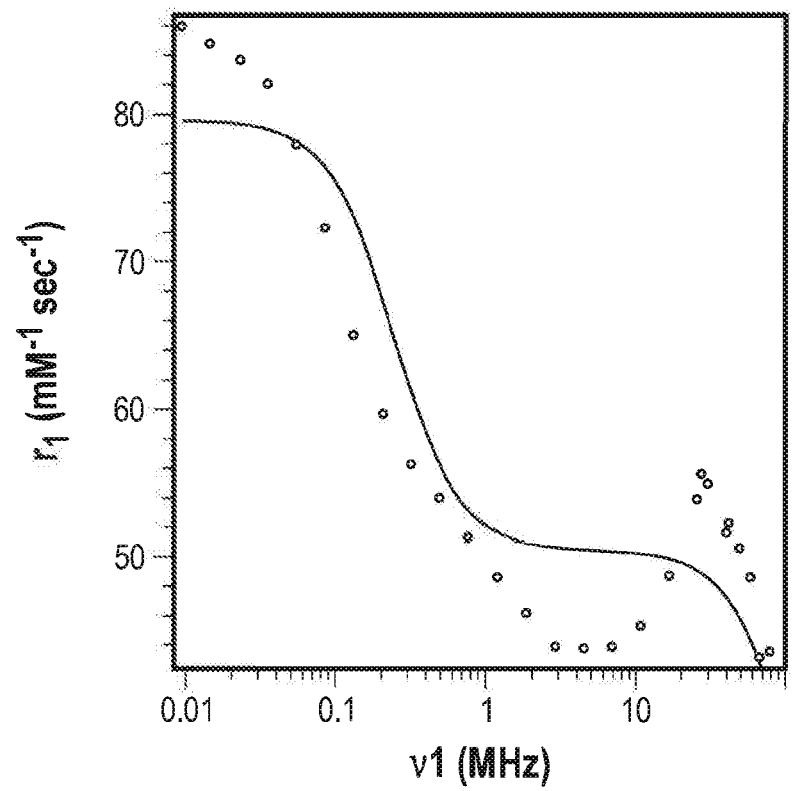
Figure 20C:
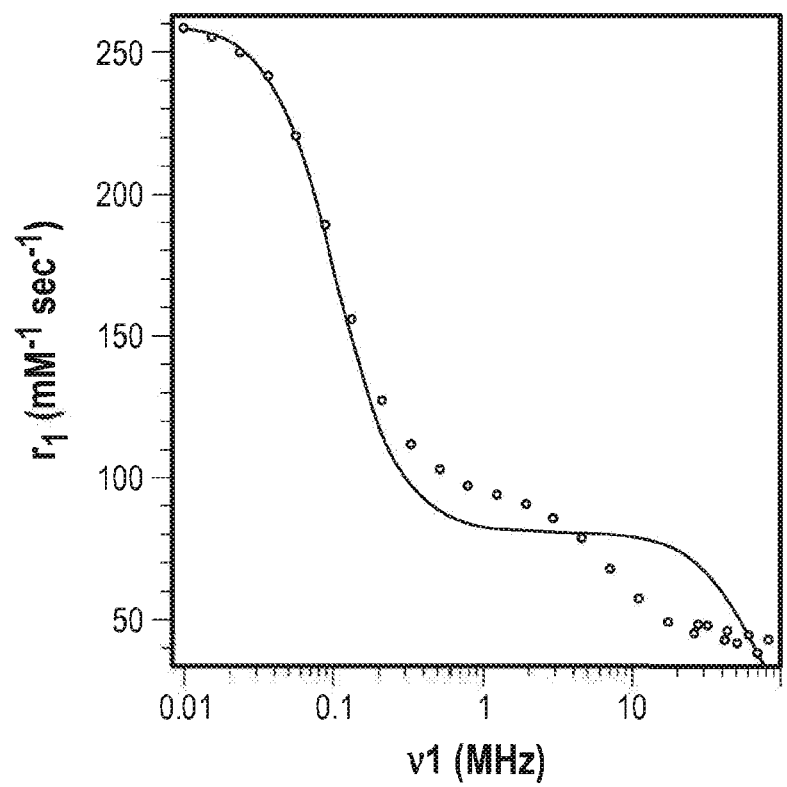
Figure 20D:
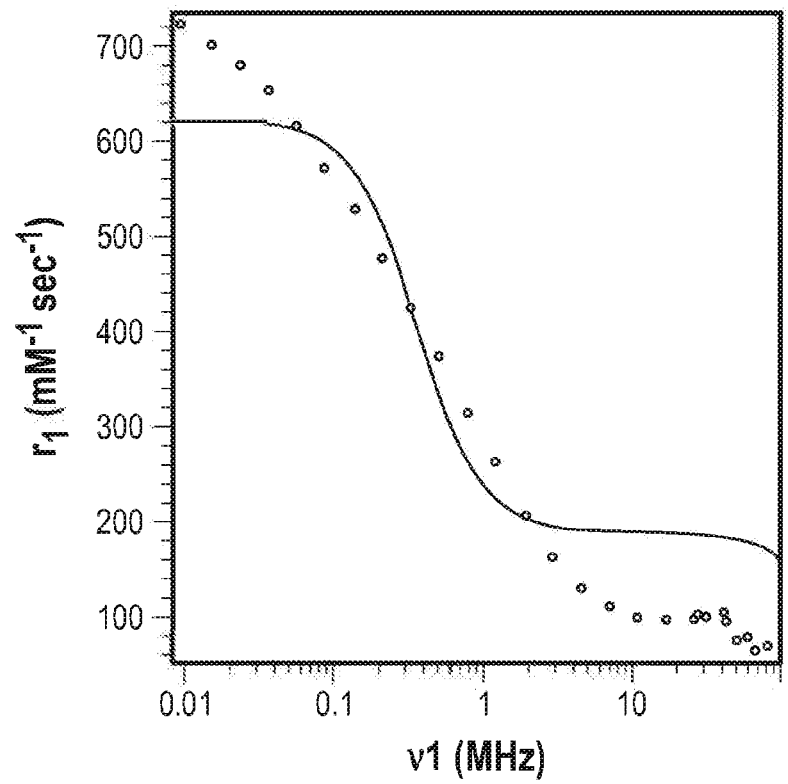
Figure 21A:
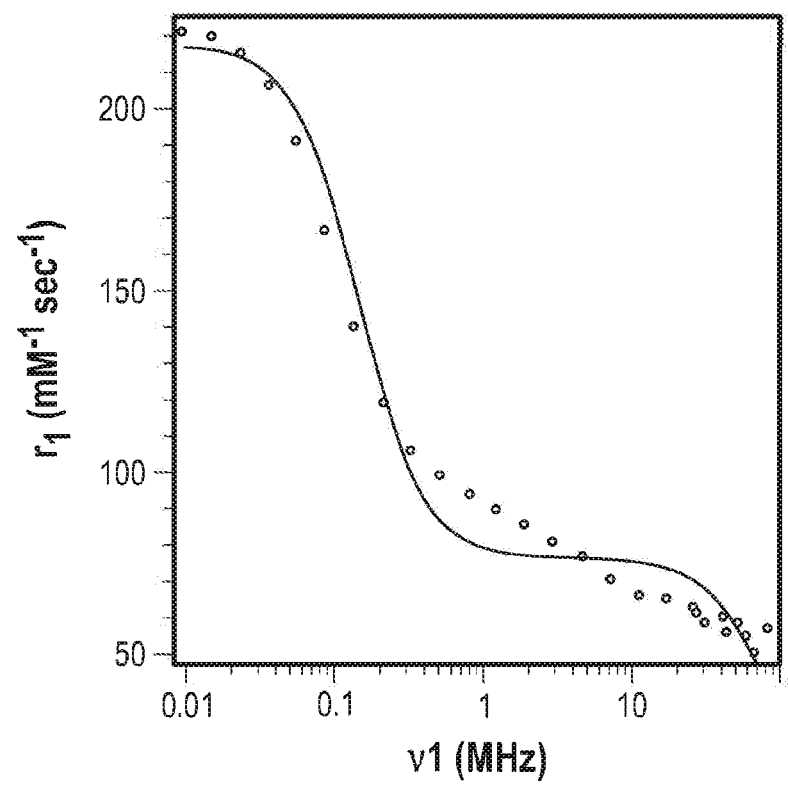
FIGS. 21(a)-21(d). Curves obtained for fixed Q=6 with remaining SBM parameters allowed to float. A) Oxidized Graphite, B) Oxidized Graphene Nanoplatelets, C) Reduced Graphene Nanoplatelets, D) Graphene Nanoribbons.
Figure 21B:
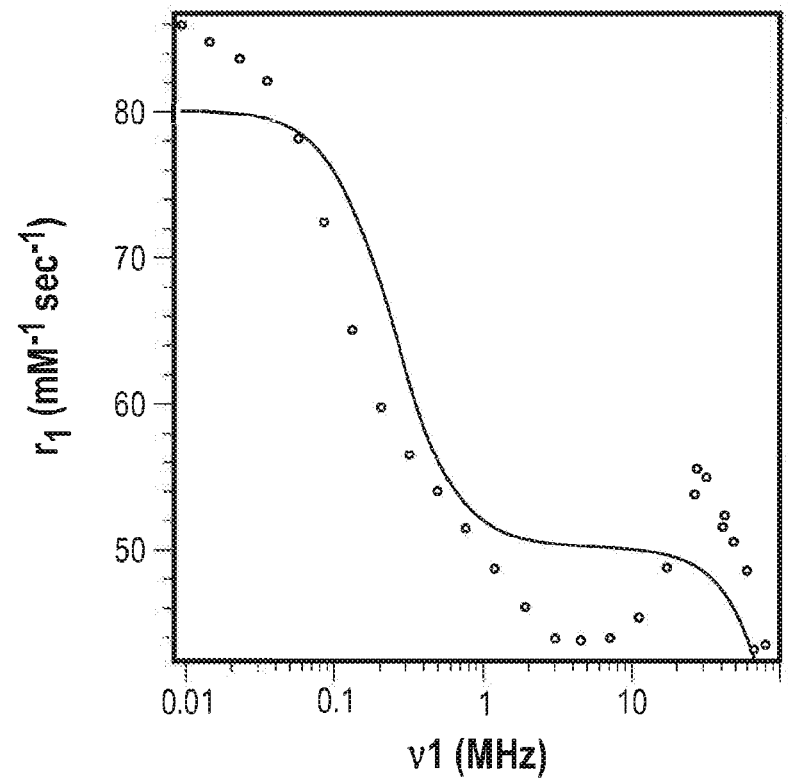
Figure 21C:
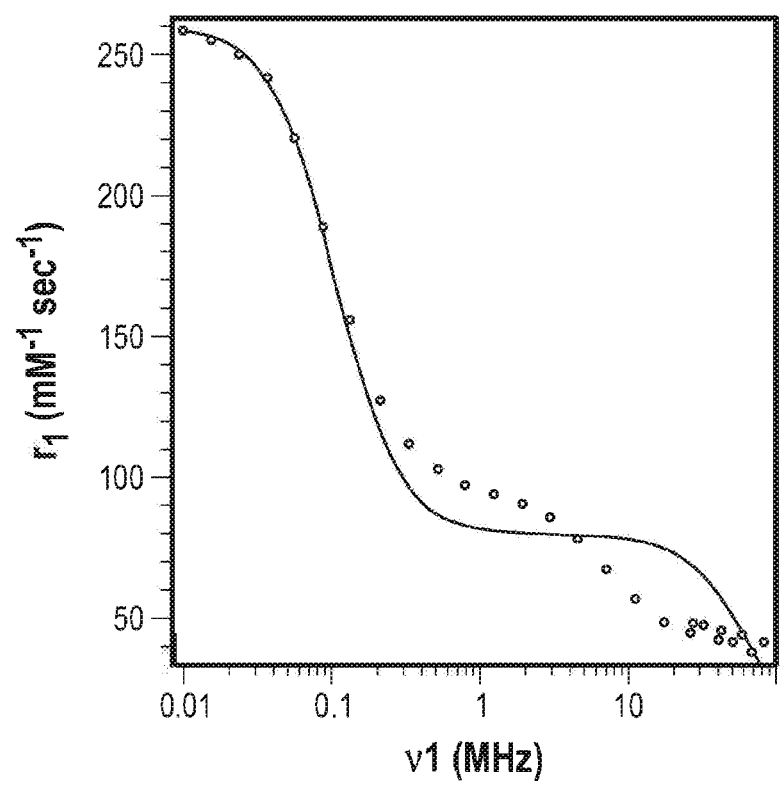
Figure 21D:
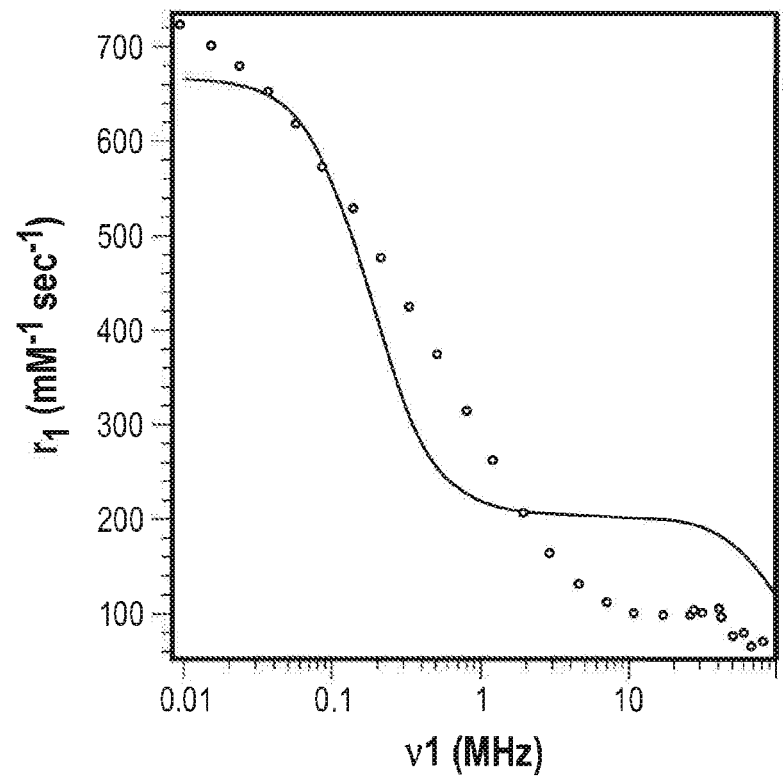
Figure 22A:
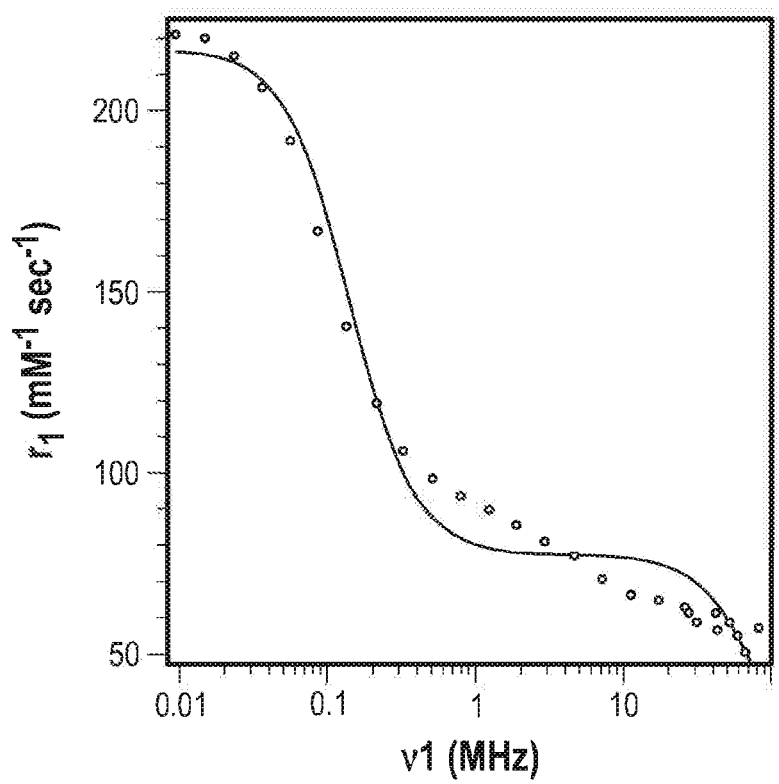
FIGS. 22(a)-22(d): Curves obtained for fixed Q=8 with remaining SBM parameters allowed to float. A) Oxidized Graphite, B) Oxidized Graphene Nanoplatelets, C) Reduced Graphene Nanoplatelets, D) Graphene Nanoribbons.
Figure 22B:
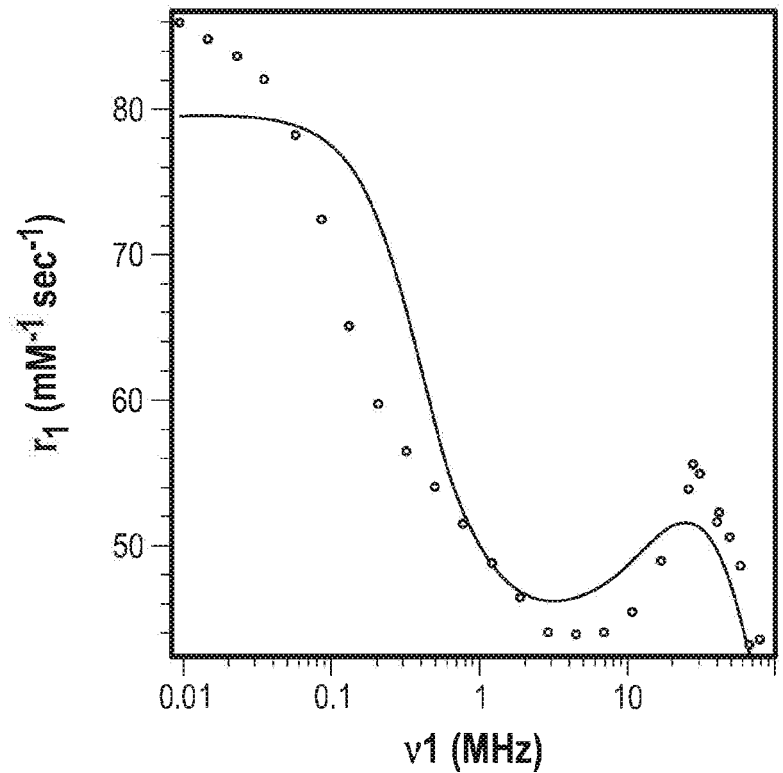
Figure 22C:
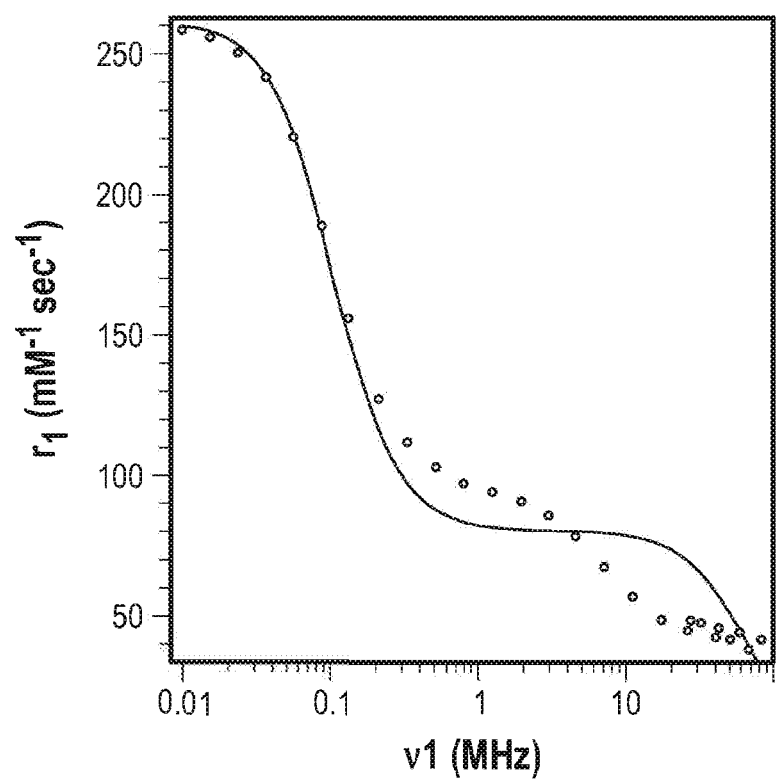
Figure 22D:
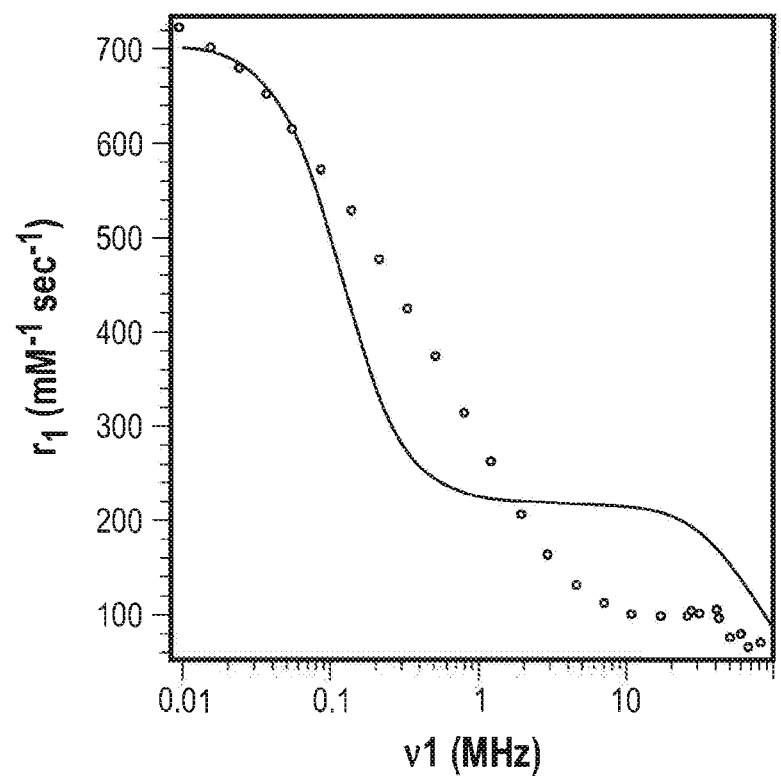
Figure 23A:
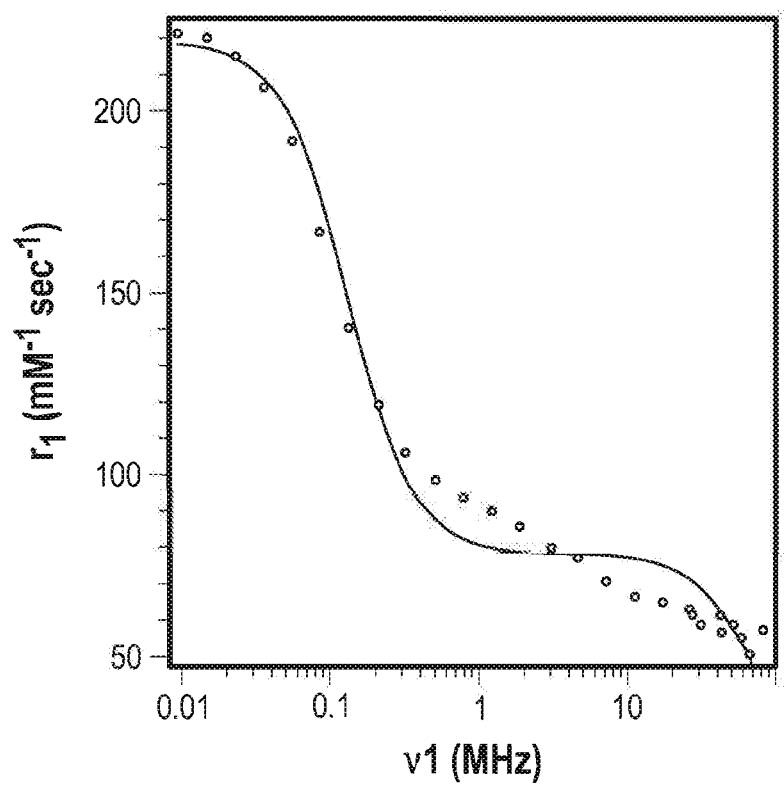
FIGS. 23(a)-23(d): Curves obtained for fixed Q=8 and Fixed $T_m$ at values shown in Table 8, with remaining SBM parameters allowed to float. A) Oxidized Graphite, B) Oxidized Graphene Nanoplatelets, C) Reduced Graphene Nanoplatelets, D) Graphene Nanoribbons. The fit for the Graphene Nanoribbons in D is surprisingly worse than expected.
Figure 23B:
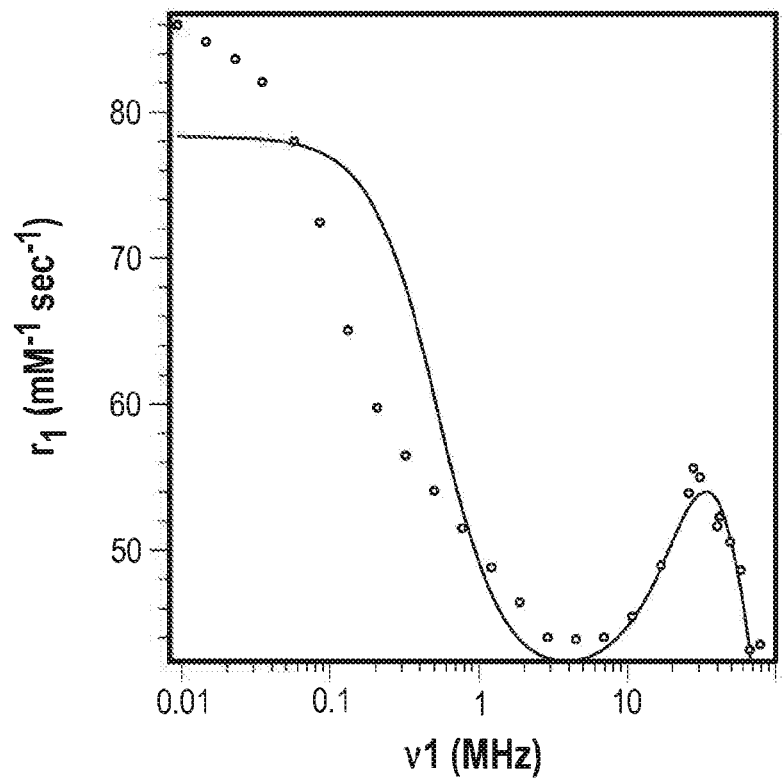
Figure 23C:
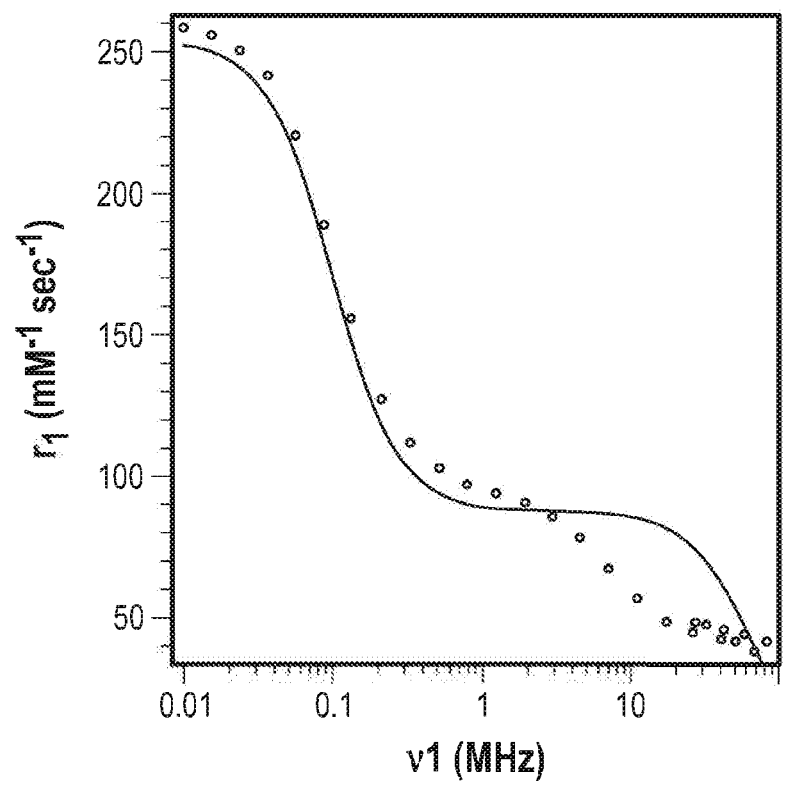
Figure 23D:
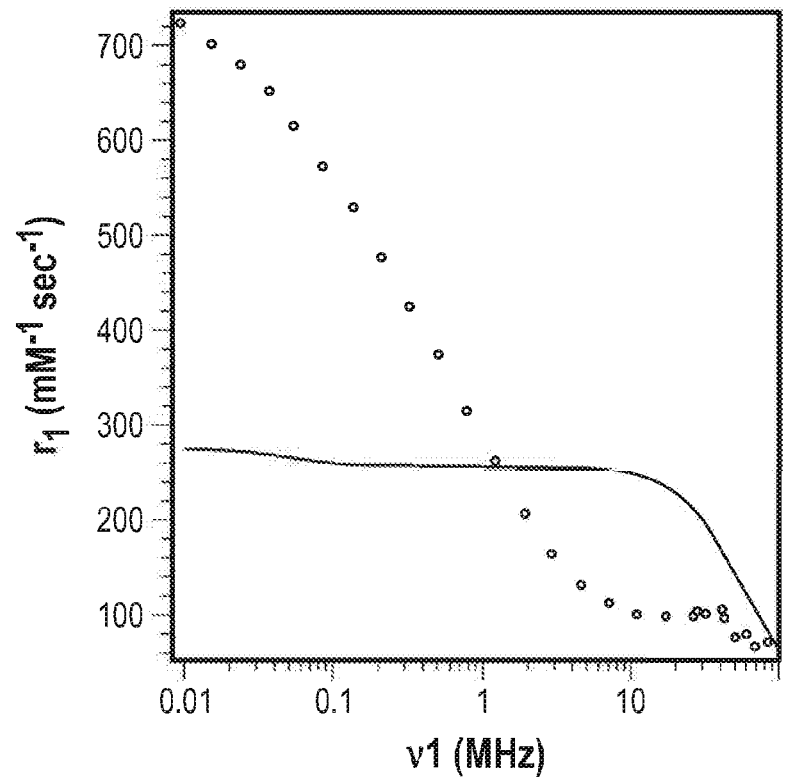

FIGS. 12(a)-12(d) show the EPR spectra of aqueous solutions of oxidized micro-graphite, oxidized graphene nanoplatelets, reduced graphene nanoplatelets and graphene nanoribbons, respectively (the blank EPR spectrum of the quartz EPR tube and the EPR spectrum of the DPPH is shown in FIGS. 17(a)-17(b)). The g values, EPR line widths at half heights ($\Delta H_{1/2}$, Gauss), hyperfine coupling constant, and electron relaxation time ($T_{2e}$) of each EPR spectra are listed in Table 3b. All the four samples show 6-line EPR characteristic of an electron coupled to Mn-55 nucleus with spin I=5/2. The EPR spectra of graphene nanoribbons also show a narrow EPR line at the center with g~2.007, and line width of 1.2 Gauss due to the presence of free radicals. The observed g values are very close to the free electron spin value, and suggest the absence of spin-orbit coupling in the ground state of manganese ions present in all four samples. The manganese hyperfine coupling ($A_{Mn}$) of approximately 95 Gauss in these samples are very close to that of aqua ions of manganese, Mn $(H_2O)_6$. The large hyperfine coupling indicates octahedral coordination in the manganese species of all four samples. The four aqueous samples also show similar narrow line width ($\Delta H_{1/2}$) values between 29.2-31.5 Gauss indicative of long electron relaxation time (T2c). The calculated $T_{2e}$ values were between 2.08-2.25 ns. The free radical species present in the graphene nanoribbons have an order of magnitude longer electron relaxation time ($T_{2e}$) of 55 ns. It should be noted that the EPR spectra only shows the Mn(II) ions. The spectra did not show presence of Mn(III) ions or other oxidation states of manganese even though, the Raman spectrum of at least reduced graphene nanoplatelets show the presence of Mn(III) ions. A possible reason of this non-detection could be that all the EPR measurements were done at room temperature. Mn(III) ions or other oxidation states of Manganese have very short electron relaxation times, and require very low sample temperatures (~77 K) to obtain an EPR spectra. Thus, low temperature measurements were also carried out on all the four samples. However, the EPR spectra (results not shown) was dominated by Mn(II) contributions, and the presence of other oxidation states of manganese could not be confirmed, suggesting that most of the manganese ions present in the four samples are present in Mn(II) state.

Relaxivity ($r_{1,2}$) is an important measure of the efficacy of an MRI contrast agent. Table 4 shows the relaxivity values at 0.47T for oxidized micro-graphite, oxidized graphene nanoplatelets, reduced graphene nanoplatelets and graphene nanoribbons at 40° C. Also included for comparative purposes are range of relaxivity values of clinically approved $Gd^+$-based and Mn2+ based chelate complexes (Rohrer et al., 2005, Investigative Radiology 40: 715-724). The table clearly shows that all four compounds show significantly higher $r_1$ and $r_2$ relaxivities compared to paramagnetic chelate complexes. At 0.47T, the $r_1$ and $r_2$ values for the graphite and graphene samples are ~8-10 times, and 19-60 times greater than paramagnetic chelate complexes. Among the graphitic and graphene samples, at 0.47T, graphene nanoribbons, and oxidized graphite showed higher (~20%) $r_1$ values than oxidized graphene nanoplatelets and reduced graphene nanoplatelets. However, the trend for $r_2$:$r_1$ ratio was reduced graphene nanoplatelets>graphene nanoribbons>oxidized micro-graphite>oxidized graphene nanoplatelets. This trend is along expected lines since, the magnetism results show that graphene nanoplatelets and graphene nanoribbons are superparamagnetic at 40° C. It is well-known that superparamagnetic materials mainly affect transverse $T_2$ relaxation, and thus, increase the $r_2/r_1$ ratio. However the $r_2/r_1$ ratio is lower than iron-based $T_2$ contrast agents that have ratios of 10 or more. $T_1$ contrast agents have $r_2/r_1$ ratios about 1-2 (Laurent et al., 2008, Chemical Reviews 108: 2064-2110). Thus, the manganese-intercalated graphitic, and graphene particles may be better suited as $T_1$ contrast agents even though at higher fields (3T or above), the reduced graphene nanoplatelets and graphene nanoribbons would give rise to $T_2^*$ effects.

The NMRD profiles between 0.01-80 MHz of aqueous solutions of oxidized graphite, oxidized graphene nanoplatelets, reduced graphene nanoplatelets and graphene nanoribbons is presented in FIGS. 13a-d. This is the first report of longitudinal $r_1$ relaxivities for these compounds over such a large magnetic field range (0.01-80). While oxidized micro-graphite and reduced graphene nanoplatelets show similar NMRD profiles, oxidized graphene nanoplatelets, and graphene nanoribbons show distinctly different profiles than these two samples. At mid-to-high magnetic field (<10 MHz), oxidized micro-graphite shows a smaller increase (50-66 mM$^{-1}$s$^{-1}$) with decrease in magnetic field, and a greater increase with decrease to lower magnetic fields (70-222 mM's$^{-1}$). Oxidized graphene nanoplatelets shows bell shaped distribution at mid-to-high magnetic fields with a maximum of 55 mM$^{-1}$s$^{-1}$ at 30 MHz, and a gradual increase up to 86 mM$^{-1}$s$^{-1}$ as the magnetic fields decrease below 10 MHz. Reduced graphene nanoplatelets shows a small increase (44-59 mM$^{-1}$s$^{-1}$) with decrease in magnetic field between 80-10 MHz, and the relaxivity increases at lower magnetic fields with a maximum value of 258 mM$^{-1}$s$^{-1}$ at 0.01 MHz. Graphene nanoribbons show a linear increase (relaxivity between 65-100 mM$^{-1}$s$^{-1}$) with decrease in magnetic fields up to 10 MHz, and then a continuous steep increase below 10 MHz reaching values of 724 mM-1s-1 at 0.01 MHz.

The NMRD profiles of these compounds are different than the profiles of other manganese-based small molecular or macromolecular complexes (Lauffer, 1987, Chem Rev 87: 901-927; and Sur et al., 1995, J Phys Chem 99: 4900-4905). For example, small molecule $Mn^{2+}$ complexes such as Mn-DTPA (DTPA=diethylene triamine penta-acetic acid) show a constant values of ~1.9 mM's$^{1}$ at fields greater than 10 MHz, and marginal increase at fields less than 10 MHz. Macromolecular complexes $Mn^{2+}$-DTPA-BSA (BSA=bovine serum albumin) show a bell-shaped relaxivity distribution at magnetic field between 10-80 MHz with a peak value of 26 mM$^{-1}$s$^{-1}$ at 20 MHz (Lauffer, 1987, Chem Rev 87: 901-927). At magnetic fields less than 10 MHz, the relaxivity is constant at ~14 mM$^{-1}$s$^{-1}$. Similar profiles have been reported for small and large molecule complexes of $Gd^{3+}$ ions (Lauffer, 1987, Chem Rev 87: 901-927). The profiles are also different than profiles of $Gd^{3+}$@$C_{60}$ (gadofullerenes) which show profiles similar to those of $Mn^{2+}$— or $Gd^{3+}$ macromolecular complexes (Toth et al., 2005, J Am Chem Soc 127: 799-805). However, the profiles of $Gd^{3+}$ @ultrashort-single-walled carbon tubes (gadonanotubes) (Ananta et al., 2010, Nature nanotechnology 5: 815-821) have features similar to those observed by $Mn^{2+}$ intercalated graphitic and graphene compounds, i.e. increase in relaxivity with decrease in magnetic field with a greater increase at magnetic fields below 10 MHz. The profile of the gadonanotubes at lower magnetic fields (<10 MHz) is most similar to that of graphene nanoribbons.

The Solomon-Bloembergan-Morgan (SBM) set of equations (see below) are considered to give the best theoretical description on how factors such as the water proton interactions with the contrast agent, magnetic properties of the contrast agent, and the molecular dynamics of the contrast agent affect the relaxation rate of the water protons at magnetic fields greater than 0.1 Tesla (Merbach et al., 2001, The Chemistry of Contrast Agents in Medical Magnetic Resonance Imaging: John Wiley & Sons. p. 471). It is widely accepted that there are three types of water molecules that can be influenced by the MRI CA: (a) the water molecules directly co-ordinated to the paramagnetic metal center of the CA are known as the inner-sphere water molecules; (b) the water molecules not co-ordinated to the magnetic metal center of the contrast agent, but chemically-bound to other molecules (e.g. ligands, chelates) of the CA are called the second sphere water molecules; and (c) the more distant water molecules that are not bound to the MRI CA, but diffuse close to it are termed the outer-sphere water molecules. Experimental nuclear magnetic relaxation dispersion (NMRD) profiles are typically fit using the SBM equations to determine these factors that influence proton relaxivity (Aime et al., 1998, Chemical Society Reviews 27: 19-29; Caravan et al., 1999, Chem Rev 99: 2293-2352; Lauffer, 1987, Chem Rev 87: 901-927; and Merbach et al., 2001, The Chemistry of Contrast Agents in Medical Magnetic Resonance Imaging: John Wiley & Sons. p. 471). Recent reports suggest that for gadonanotubes, the factors that govern their interactions with the inner-sphere water protons such as proton/water exchange rate, and the rotational correlation time are responsible for most of the observed r, relaxivity (Ananta et al., 2010, Nature nanotechnology 5: 815-821). Thus, SBM equations that describe the inner-sphere interactions were the main focus. FIGS. 13a-d show the NMRD profiles of the oxidized graphite, oxidized graphene nanoplatelets, reduced graphene nanoplatelets, and graphene nanoribbons, respectively. Also included are the corresponding best-fit, physically reasonable values (within the range of values reported for other Gd(III) and Mn(II)-based compounds) for the various inner-sphere parameters. (A discussion of our fitting approach is presented below). Table 5 lists the computed parameters, their definitions and values (Table 8 lists the fixed parameters, their definitions and values). In general, the SBM equations provide an acceptable fit at high fields (>10 MHz) or low field (<0.5 MHz). Overall, the fits were more accurate for oxidized micro-graphite, and reduced graphene nanoplatelets than for oxidized graphene nanoplatelets and nanoribbons. This indicates that the SBM equations may not be an entirely satisfactory model for all the compounds synthesized here. Nevertheless, the parameters returned by the curve-fitting algorithm were discussed below to examine if they are in line with those reported elsewhere.

The parameter $\Delta^2$ represents the zero-field splitting energy of the paramagnetic metal's electrons. Even in the absence of an applied field, which is normally used to produce Zeeman splitting, splitting can still occur due to random motions and distortions of the complex. The fields generated by these interactions produce energy which induces relaxation in the nearby protons. The correlation time for this splitting is termed $\tau_v$. These two parameters are important in determining the effectiveness of the paramagnetic center. $\Delta^2$ is generally in the range of $10^{18}$-$10^{20}$ s$^{-2}$. The values found from the fits are well within the accepted range. The value of r, is generally accepted as being from 1-100 picoseconds (Lauffer, 1987, Chem Rev 87: 901-927). The values we have found are in this range. In case of r, the rotational correlation time, values in the 10 ps to 2 ns range were reported (Aime et al., 2002, Journal of Biological Inorganic Chemistry 7: 58-67; Lauffer, 1987, Chem Rev 87: 901-927; and Toth et al., 2005, J Am Chem Soc 127: 799-805), while for gadonanotubes values dropping into the nanosecond to microsecond range were also reported (Ananta et al., 2010, Nature nanotechnology 5: 815-821). The results obtained for the micro-graphite and graphene samples are in the nanosecond time scale. The parameter q represents the number of fast-exchanging water molecules within the inner sphere, and its value was 8 for all the samples. These values fall outside the range of values for q obtained for various paramagnetic complexes, which are between 1 and 6. However, q values as high as high as 20 have reported for gadofullerenes (Toth et al., 2005, J Am Chem Soc 127: 799-805). Theoretical studies on Manganese intercalation within graphene suggest coordination of manganese to the graphene sheets with 1-3 co-ordination bonds (Mao et al., 2008, Nanotechnology 19: 205708). Assuming most of the intercalated graphene is $Mn^{2+}$ in the high spin state, the co-ordination number can be between 4 and 8 and thus, the possible co-ordination sites for water molecules will be between 1 and 7, and value obtained from the NMRD fits is close to this value. Additionally, the EPR results also indicate that this value is reasonable. The parameter $\tau_M$, the water-residence lifetime has a dual effect on the relaxivity. On one hand, the longer a water molecule is resident in the inner sphere, the more time the paramagnetic center can influence its spin. However, if its resident time is too long, it blocks the ability of other water molecules from co-ordinating to the paramagnetic metal center, and can reduce the overall relaxivity. Hence, the optimum relaxivity is somewhere between the possible extremes. Literature reports show a wide range $\tau_M$ values. Small molecule complexes are generally in the range of 11-100 ps, while macromolecules such as paramagnetic liposomes (Hak et al., 2009, European Journal of Pharmaceutics and Biopharmaceutics 72: 397-404), gadofullerenes (Toth et al., 2005, J Am Chem Soc 127: 799-805), gadonanotubes (Ananta et al., 2010, Nature nanotechnology 5: 815-821) have values between 100-500 ns. The values found from the fits range between a few to hundreds of nanoseconds. To corroborate this data, $^{17}O$ measurements were performed at 14T, and the water exchange correlation time $(\tau_M)$ was estimated by analyzing the data according to the Swift and Connick theory (see below) (Swift et al., 1962, J Chem Phys 37: 307). The $\tau_M$ value was estimated to be hundreds of ns for all samples at 27° C. While these values corroborate well with the $\tau_M$ values obtained from NMRD fits oxidized micro-graphite and oxidized graphene nanoplatelets, they are 100 times greater than the values of reduced graphene nanoplatelets and graphene nanoribbons. The NMRD fits obtained by fixing the values of $\tau_M$ at hundreds of nanoseconds for these two samples gave good fits, and reasonable values for other parameters in case of reduced graphene nanoplatelets, however, a poor fit was obtained for graphene nanoribbons (See FIGS. 23A-23D). The separation distance, $r_{MnH}$ between the water protons and the paramagnetic metal ion ($Mn^{2+}$ ion in this case) is raised to the $6^{th}$ power in the SBM equations. Thus, it has a very large influence on relaxivity, with shorter the distance, larger the influence. In this work, we found that allowing the parameter to vary slightly, rather than hold it fixed at the most commonly reported value of 2.9 angstroms (Troughton et al., 2004, Inorg Chem 43: 6313-6323). The fitting values we obtained were in any case very close to the nominal value, but due to the extreme sensitivity of the SBM equations toward this value, it allowed for improved fits.

Multiple approaches have been developed wherein the above factors that affect the relaxation mechanism have been altered to design new high-efficiency $Mn^{2+}$-based or $Gd^{3+}$-based $T_1$ MRI CA (Table 6). These approaches have focused on altering one or more of the following parameters: (1) increasing the number of inner-sphere water molecules (q); (2) decreasing the inner-sphere water residence lifetime $(\tau_M)$, and increasing the rotational correlation time $(\tau_R)$ of the contrast agent (CA); (3) decreasing the $r_{MnH}$a by altering bond angles and orientation when designing chelates (Caravan et al., 2009, Contrast Media Mol Imaging 4: 89-100). In the case of $Mn^{2+}$ based macromolecular contrast agents, at 20 MHz, $r_1$ values as high as 55 $mM^{-1}$ have been reported compared to $Mn^{2+}$ ions without any chelate or chelated with various small molecule polycarboxylic acid ligands which show $r_1$ values between 4-10 $mM^{-1}s^{-1}$. The two parameters that have been manipulated in these studies are $\tau_M$ and/or $\tau_R$. The results of this work introduce a novel general approach to enhance the $r_1$ relaxivity by confining the paramagnetic metal between graphene sheets, allowing the characteristic parameters q, $\tau_R$, and $\tau_M$ to be modified accordingly. The results indicate that confinement (intercalation) of paramagnetic metal ions within graphene sheets, and not the size, shape or architecture of the graphitic carbon particles is the key determinant for increasing relaxivity, and thus, identifies nano confinement of paramagnetic ions as novel general strategy to develop metal-ion graphitic-carbon complexes as high relaxivity MRI CA.

The physiochemical characterization, and the promising relaxivity results of the graphitic, and graphene structures reported in the these examples open avenues for in vitro and in vivo studies to assess their safety and efficacy as MRI CAs. According to a recent report, in the US, approximately 43% of the 27.5 million clinical MRI procedures use CAs and the MRI CA market is projected to grow to $1.87 billion in 2012 ((2011) Imaging Agents. Global Industry Analysts, Inc: http://www.strategyr.com/ImagingAgents_Market_Report.asp). Most clinical MRI CAs are gadolinium-($Gd^{3+}$) ion-based $T_1$ paramagnetic CAs, that enhance MR signals to generate bright positive contrast. The recent discovery of nephrogenic systemic fibrosis (NSF) in some patients with severe renal disease or following liver transplant has generated concern leading to Food and Drug Administration (FDA) restrictions on clinical use of the $Gd^{3+}$-ion based MRI CA (US FDA Information on gadolinium-containing contrast agents 2008, http://wwwfdagov/cder/drug/infopage/gcca/). Manganese, which was reported early on as an example of paramagnetic contrast material for MRI, has again received attention as a possible alternative to gadolinium (Pan et al., 2010, Revisiting an old friend: manganese based MRI contrast agents. Wiley Interdisciplinary Reviews: Nanomedicine and Nanobiotechnology). Unlike the lanthanides, it is a natural cellular constituent resembling $Ca^{2+}$, and often functions as a regulatory cofactor for enzymes and receptors. Normal daily dietary requirement for manganese is 0.1-0.4 milligrams, while normal serum levels are 1 nano-molar. Manganese toxicity has only been reported following long-term exposure or at high concentrations resulting in neurological symptoms (Pan et al., 2010, Revisiting an old friend: manganese based MRI contrast agents. Wiley Interdisciplinary Reviews: Nanomedicine and Nanobiotechnology). Thus, further development of the micro- and nano-particles reported in this work could lead to development of a new class of $Mn^{2+}$-carbon nanostructure complexes as high-efficacy MRI CAs.

TABLE 3a

EPR parameters of solid samples of oxidize micro-graphite, oxidized graphene nanoplatelets, reduced graphene nanoplatelets and graphene nanoribbons.

| Sample | g-value | EPR Line width ($\Delta H_{1/2}$, Gauss) for g~2.0 | Electron relaxation time ($T_{2e}$, nanoseconds) |
|---|---|---|---|
| Oxidized micrographite | 2.007 | 552.0 | 0.19 |
| Oxidized graphene nanoplatelets | 2.007 | 544.4 | 0.20 |
| Reduced graphene nanoplatelets | 2.008 | 505.2 | 0.21 |
| Graphene nanoribbons | 2.313 | 1472.0 | 88.2 |

TABLE 3b

EPR parameters of aqueous samples of oxidize micro-graphite, oxidized graphene nanoplatelets, reduced graphene nanoplatelets and graphene nanoribbons.

| Sample | g-value | EPR Line width ($\Delta H_{1/2}$, Gauss) for g~2.0 | Hyperfine Coupling Constant $A_{Mn}$, Gauss | Electron relaxation time ($T_{2e}$, nanoseconds) |
|---|---|---|---|---|
| Oxidized micro-graphite | 2.0067 | 29.2 | 94.5 | 2.25 |
| Oxidized graphene nanoplatelets | 2.0068 | 31.5 | 96.4 | 2.08 |
| Reduced graphene nanoplatelets | 2.0070 | 30.0 | 95.4 | 2.19 |
| Graphene nanoribbons | 2.0068 | 30.2 | 95.2 | 2.17 |

TABLE 4

Relaxivity of oxidized graphite, oxidized graphene nanoplatelets, reduced graphene nanoplatelets and graphene nanoribbons dispersed in 1% Pluronic F127 solutions compared with clinically used MRI contrast agents.

| Sample | $r_1$ (mM$^{-1}$s$^{-1}$) | $r_2$ (mM$^{-1}$s$^{-1}$) | $r_2/r_1$ |
|---|---|---|---|
| Oxidized graphite | 63 (61-78) | 171 (169-184) | 2.7 |
| Oxidized Graphene nanoplatelets | 52 (50-54) | 114 (114-131) | 2.2 |
| Reduced graphene nanoplatelets | 47 (34-49) | 415 (389-430) | 8.9 |
| Graphene nanoribbons | 62 (53-71) | 303 (275-310) | 4.9 |
| Clinical Mn$^{2+}$Chelate Complexes[†] | 1.8-2.0 | 2.0-2.2 | — |
| Clinical Gd$^{3+}$Chelate Complexes[††] | 3.4-5.8 | 3.6 ± 7.0 | — |

[†]Sigma- Aldrich I Certificate of Analysis- MWCNT
[††]Rohrer et al., 2005, Investigative Radiology 40: 715-724

TABLE 5

Computed parameters representing best fit to SBM equations.

| Parameter | Definition | Oxidized Graphite | Oxidized Graphene Nanoplatelets | Reduced Graphene Nanoplatelets | Graphene Nanoribbons |
|---|---|---|---|---|---|
| $\Delta^2$ | Zero-field splitting energy (ZFS) | $1.0 \times 10^{18}$ | $6.12 \times 10^{18}$ | $1.0 \times 10^{18}$ | $1.0 \times 10^{18}$ |
| $\tau_V$ (sec) | Correlation time for splitting | $1.18 \times 10^{-12}$ | $1.09 \times 10^{-11}$ | $1.99 \times 10^{-12}$ | $1.0 \times 10^{-12}$ |
| $\tau_R$ (sec) | Tumbling time of complex | $1.95 \times 10^{-9}$ | $1.77 \times 10^{-9}$ | $3.85 \times 10^{-9}$ | $3.69 \times 10^{-9}$ |
| q | Hydration number | 8 | 8 | 8 | 8 |
| $\tau_M$ (sec) | Residence time of inner sphere water molecules | $1.42 \times 10^{-7}$ | $7.29 \times 10^{-7}$ | $7.06 \times 10^{-9}$ | $5.06 \times 10^{-9}$ |
| $r_{MnH}$ (m) | Manganese-Hydrogen Bond Radius | $3.76 \times 10^{-10}$ | $3.73 \times 10^{-10}$ | $3.94 \times 10^{-10}$ | $3.26 \times 10^{-10}$ |

TABLE 6

Relaxivity ($r_1$) of Mn$^{2+}$-based or Gd$^{3+}$-based $T_1$ MRI contrast agents, and the dominant SBM parameter(s) that influence the relaxation mechanism.

| Type of Compound | Mn$^{2+}$-based Highest $r_1$ (mM$^{-1}$s$^{-1}$) | Mn$^{2+}$-based Magnetic field (MHz) | Gd$^{3+}$-based Highest $r_1$ (mM$^{-1}$s$^{-1}$) | Gd$^{3+}$-based Magnetic field (MHz) | Parameter(s) |
|---|---|---|---|---|---|
| liposomal complex[1,2] | 35 | 20 | 11 | 25 | $\tau_M$ |
| Chelate complexes that non-covalent binding to Protein[1,3,4] | 55 | 20 | 130 | 20 | $\tau_R$ |
| Dendrimer complex[4,5] | 4.7 | 200 | 20 | 130 | $\tau_R$ |
| Viral capsid complexes[6] | Not available | Not available | 42 | 30 | q, $\tau_R$ |
| Small molecule complexes non-covalently functionalized to carbon nanotubes[7] | Not available | Not available | 50 | 20 | $\tau_R$ |

TABLE 6-continued

Relaxivity ($r_1$) of $Mn^{2+}$-based or $Gd^{3+}$-based $T_1$ MRI contrast agents, and the dominant SBM parameter(s) that influence the relaxation mechanism.

| Type of Compound | $Mn^{2+}$-based | | $Gd^{3+}$-based | | |
|---|---|---|---|---|---|
| | Highest $r_1$ (mM$^{-1}$s$^{-1}$) | Magnetic field (MHz) | Highest $r_1$ (mM$^{-1}$s$^{-1}$) | Magnetic field (MHz) | Parameter(s) |
| Small molecule complexes covalently functionalized to nano-diamonds[8] | Not available | Not available | 59 | 60 | $\tau_R$ |
| Metallofullerenes[9-11] | Not available | Not available | 8-100 | 20-50 | q, $\tau_R$ |
| Metallonanotubes[12-13] | Not available | Not available | 400-635 | 0.01 | q, $\tau_M$, $\tau_R$ |

[1]Lauffer, 1987, Chem Rev 87: 901-927
[2]Hak et al., 2009, European Journal of Pharmaceutics and Biopharmaceutics 72: 397-404
[3]Troughton et al., 2004, Inorg Chem 43: 6313-6323
[4]Pan et al., 2010, Revisiting an old friend: manganese based MRI contrast agents. Wiley Interdisciplinary Reviews: Nanomedicine and Nanobiotechnology
[5]Bryant et al., 1999, Journal of Magnetic Resonance Imaging 9: 348-352
[6]Datta et al., 2009, Accounts Chem Res 42: 938-947
[7]Richard et al., 2008, Nano Letters 8: 232-236
[8]Manus et al., 2009, Nano Letters 10: 484-489
[9]Toth et al., 2005, J Am Chem Soc 127: 799-805
[10]Kato et al., 2003, J Am Chem Soc 125: 4391-4397
[11]Fatouros et al., 2006, Radiology 240: 756-764
[12]Sitharaman et al., 2005, Chem Commun: 3915-3917
[13]Ananta et al., 2010, Nature nanotechnology 5: 815-821

Structural, Chemical and Elemental Analysis:
1. Structural Characterization and Raman Analysis Scanning electron microscopy (SEM, JSM 5300, JEOL) was performed at 80 kV on the oxidized micro-graphite samples to characterize their size and structure. High Resolution Transmission Electron Microscopy (TEM) imaging analysis was performed on the graphene nanoplatelets and nanoribbons samples using a high resolution analytical transmission electron microscope (JEOL JEM2010 OF (FEG-TEM)). Imaging was carried out at 200 kV accelerating voltage. TEM samples were prepared by dispersing the dry powders in 1:1 ethanol:water to form a homogeneous mixture. The suspension was then deposited on to a 300 mesh Cu grid covered with a lacey carbon film. For the aberration ($C_s$) corrected TEM characterization, the experiments were performed in a Titan cubed 300-60 kV operated at 80 kV equipped with a spherical aberration corrector for the objective lens. Images were commonly recorded for 0.4 seconds. The Electronic Energy Loss Spectra (EELS) detector in this case used to collect the spectra was Tridiem. RAMAN spectral analysis of graphite, oxidized graphite, and all graphene samples was performed between 200 to 3000 cm$^{-1}$ using a Thermo Scientific DXR Raman confocal microscope at 530 nm diode laser excitation wavelength and room temperature.

Figure 14A:
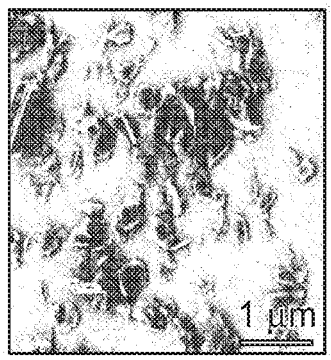
FIGS. 14(a)-14(g): Representative SEM image of (a) oxidized micro-graphite and TEM images of (b,c) reduced graphene nanoplatelets and (d,e) graphene nanoribbons. Arrows in (e) show the multiple layers of graphene nanoribbon sheets. (f) TEM images at 200 kV for reduced graphene nanoplatelets Shows ~20 nm wide few layered and multilayered reduced graphene nanoplatelets. (g) AFM Section analysis of graphene nanoplatelets dispersed on silicon substrate, showing a uniform thickness of ~1.137 nm.
Figure 14B:
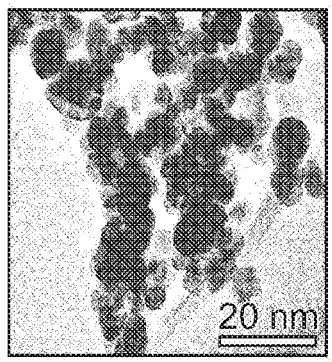
Figure 14C:
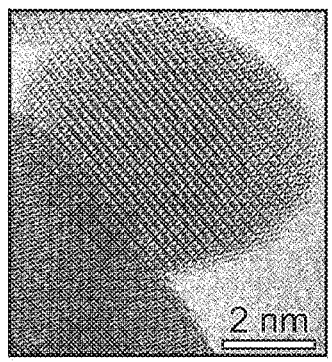

FIG. 14(a) displays the scanning electron microscopy image of the oxidized micro-graphite particles. The images indicate that oxidized micrographite particles exist as fractured structure, and have sizes (longest length of fractured structure) between 3-4 µm with an average size of 2.5 µm. FIGS. 14(b) and 14(c) display representative low and high magnification TEM images of reduced graphene nanoplatelets, respectively, which provide their structural and morphological information. The structural properties of the graphene nanoparticles are similar to recent reports on the large scale production of graphene nanoplatelets and graphene nanoribbons (Stankovich et al., 2006, Journal of Materials Chemistry 16: 155-158; Stankovich et al., 2007, Carbon 45: 1558-1565; Stankovich et al., 2006, Carbon 44: 3342-3347; Li et al., 2008, Nature nanotechnology 3: 101-105; Kosynkin et al., 2009, Nature 458: 872-876; Higginbotham et al., 2010, ACS nano 4: 2059-2069; Geng et al., 2009, Journal of colloid and interface science 336: 592-598). As seen in FIG. 14b, the reduced graphene nanoplatelets are circular in shape with an average width of ~20 nm. Some platelets appear darker than the others, and this is due to the presence of multi-layered graphene sheets. The lighter ones, which are almost transparent, are single or double layered graphene sheets. FIG. 14(c) reveals the atomic lattice fringe structure of the individual graphene sheets; the lattice grid lines and hexagonal carbon atom rings are clearly visible (Lu et al., 2009, Nano Research 2: 192-200). AFM section analysis of the reduced graphene nanoplatelets dispersion on a Si substrate revealed a uniform thickness of ~1.137 nm (FIG. 14g). Pristine graphene sheets have an atomic layer thickness (Van der Waals) of 0.34 nm. The presence of covalent bonds with carboxyl and hydroxyl groups, and displacement of sp$^3$ carbon atoms in the graphene nanoplatelet structure has been reported to be the reason for the increase in the thickness (Stankovich et al., 2007, Carbon 45: 1558-1565). Oxidized graphene oxide nanoparticles show similar sizes and architecture (FIG. 14f).

Figure 14D:
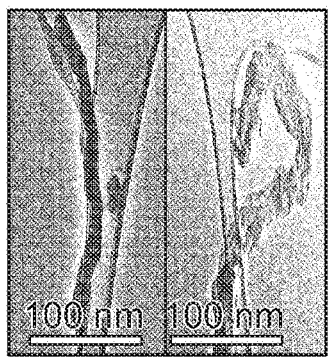
Figure 14E:
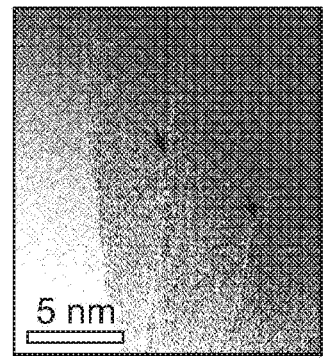
Figure 14F:
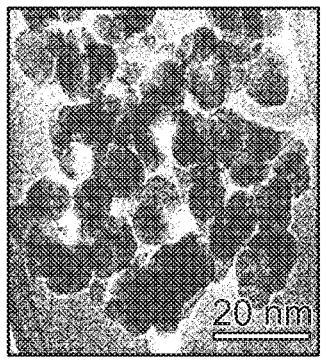
Figure 14G:
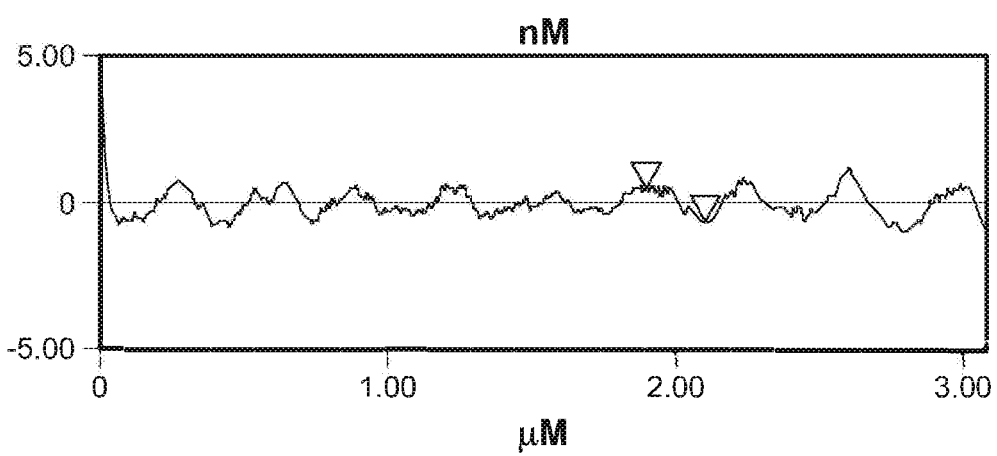

FIG. 14(d) and e display representative low and high magnification TEM images of graphene nanoribbons, respectively. As seen in FIG. 14(d), the graphene nanoribbons have fully unzipped layers of graphene sheets. The high resolution TEM image in FIG. 14(e) clearly shows that the nanoribbons are multilayered (arrows) due to successive unzipping of the concentric walls of MWCNTs. The graphene oxide nanoribbons structure appears mostly uniform and smooth, with few defects. The starting material, MWCNTs, have an outer diameter of 40-70 nm, and length of 500-2000 nm. Since the MWCNTs are cylinders, upon unzipping, they should open up completely to have breadths of ~125-220 nm (π×diameter) and lengths of 500-2000 nm. The analysis of the TEM images indicates that the width of the graphene nanoribbons is ~120 nm which is greater than the outer diameter of the outermost tubes of MWCNTs of 70 nm verifying the process of unzipping. However, this width is slightly lower than the range required for fully flat ribbons (125-220 nm) suggesting that, the graphene nanoribbons upon unzipping may not be fully flat sheets, but retain some curvature of the MWCNTs. The TEM images also show that the graphene nanoribbons have lengths of ~600-2000 nm similar to the MWCNTs.

Figure 15A:
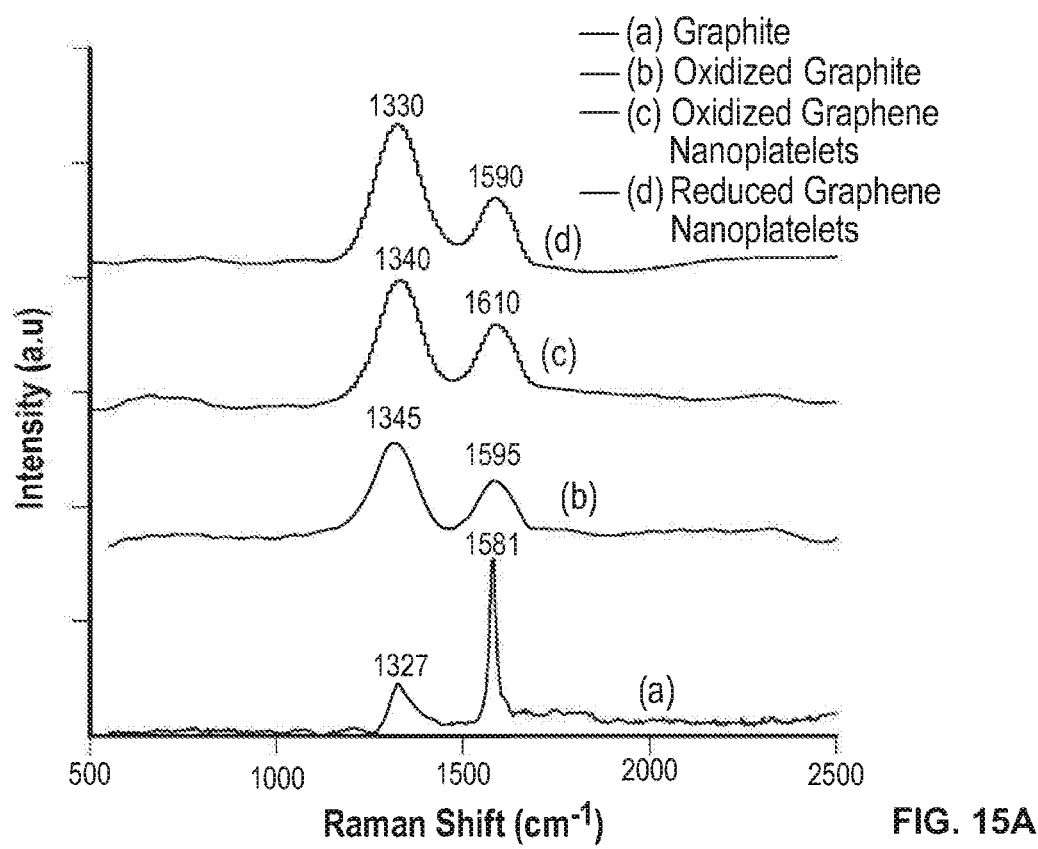
FIGS. 15(a)-15(c): Raman spectrum with the D and G bands peaks for (a) graphite, oxidized graphite, oxidized graphene nanoplatelets and reduced graphene nanoplatelets, and (b) MWCNTs and graphene nanoribbons (c) Comparison of Raman spectra between Hausmannite ($Mn_3O_4$), oxidized graphite and reduced graphene nanoplatelets at 532 nm showing spectral peaks at 657, 370 and 320 $cm^{-1}$.

FIG. 15(a) shows the Raman spectra of oxidized micro-graphite, oxidized graphene nanoplatelets and reduced graphene nanoplatelets. Also included as control, is the Raman spectra of pristine micro-graphite. The spectrum of pristine micro-graphite shows a prominent sharp peak at 1581 cm$^{-1}$ indicating the G-band which is attributed to the doubly degenerate zone center $E_{2g}$ mode (Tuinstra et al., 1970, Raman spectrum of graphite. The Journal of Chemical Physics 53: 1126). In case of oxidized graphite, there is a broadening of the G band, and a peak shift to 1595 cm$^1$. Further, zone boundary phonons give rise to the D band at 1345 cm$^{-1}$, which becomes prominent indicating increase in the disorder sp$^2$ domains, and reduction of the crystal size due to oxidation. Due to oxidation of graphite, there is an increase in the ratio of intensity of the D to G peaks ($I_D/I_G$), from 0.407 for graphite to 1.2 for oxidized graphite (Tuinstra et al., 1970, Raman spectrum of graphite. The Journal of Chemical Physics 53: 1126). The spectra of oxidized graphene nanoplatelets, and reduced graphene nanoplatelets show a further increase in $I_D/I_G$ to 1.3 and 1.44, respectively. In case of reduced graphene nanoplatelets, the peaks of D and G bands are shifted closer to the values of graphite (1330 cm$^{-1}$ and 1590 cm$^{-1}$ respectively), suggesting the removal of the oxygen during reduction, and some restoration of sp$^2$ carbon atoms. However, $I_D/I_G$ ratio is higher compared to oxidized graphene nanoplatelets possibly due to the reduction of the average size of sp$^2$ domains in addition to an increase in the number of such small sized disorder domains (Stankovich et al., 2007, Carbon 45: 1558-1565).

Figure 15B:
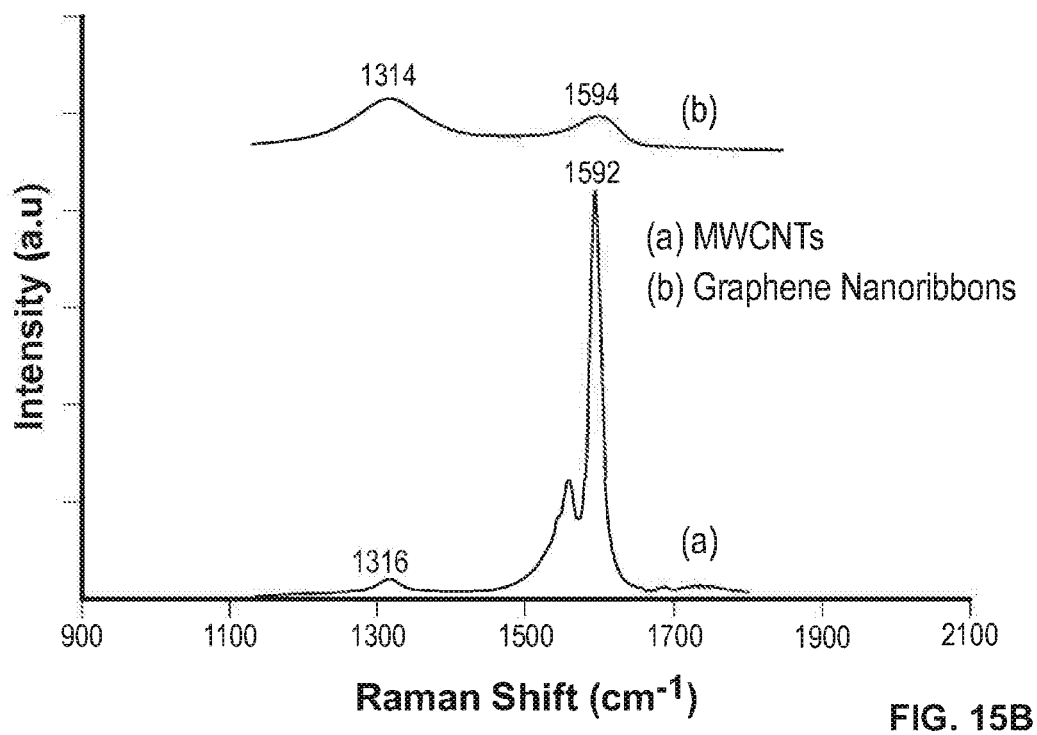

FIG. 15(b) shows the Raman spectrum of graphene nanoribbons and MWCNTs. The spectrum for graphene nanoribbons has a broad G band, which is red-shifted at 1600 cm$^{-1}$ compared to MWCNT and has a prominent D band at 1310 cm$^{-1}$. There is an increase in $I_D/I_G$ value from 0.045 for MWCNTs to 1.57 for the graphene nanoribbons, similar to previous reports (Kosynkin et al., 2009, Nature 458: 872-876). The red-shift in the G band for the graphene nanoribbons is due to the oxidative unzipping of MWCNTs, and is similar to the shift in spectra for oxidized graphene nanoplatelets, due to oxidation of graphite (FIG. 15(a)).

Figure 15C:
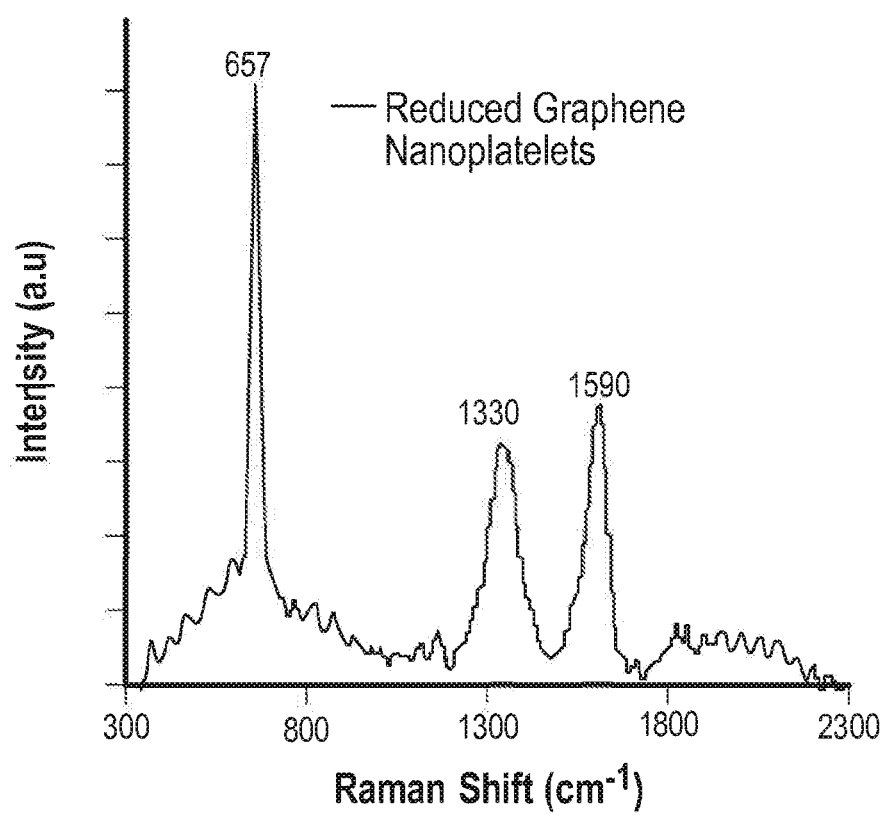
Figure 15C:
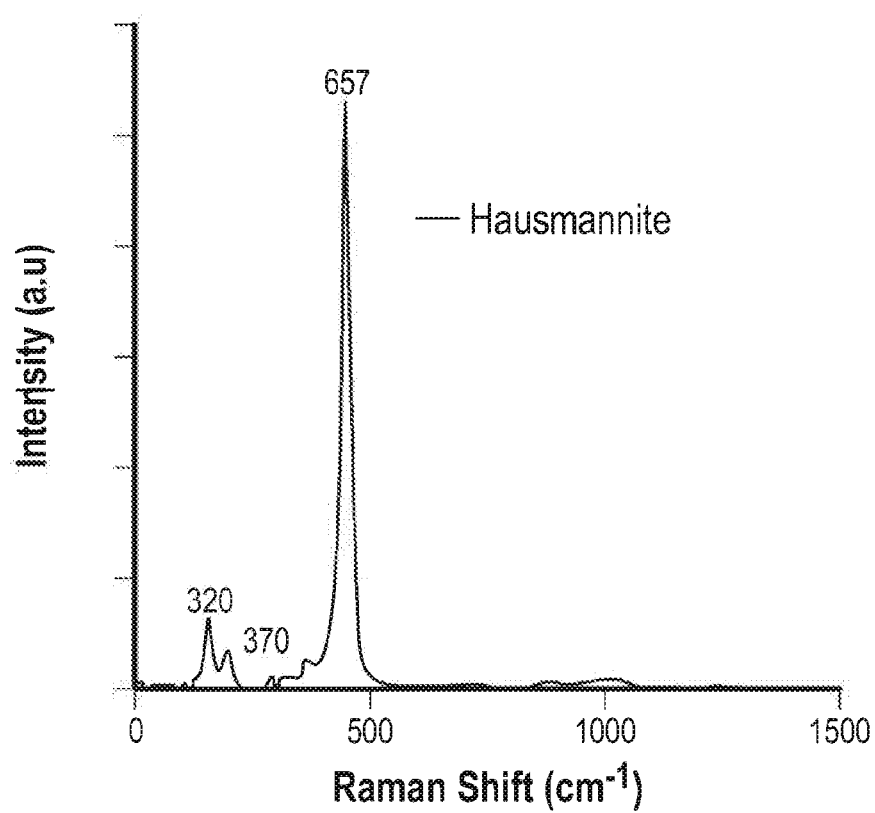

The Raman spectra of reduced graphene nanoplatelets also show additional peaks at around 657 cm$^{-1}$, 370 cm$^{-1}$ and 320 cm$^{-1}$ (FIG. 15(c)). In order to identify the peaks, a Raman spectral database search (using the RRUFF™ project collection, http://rruff.info/R040090) attributed the peaks to Hausmannite ($Mn_3O_4$); a complex oxide containing di-valent and tri-valent manganese. Hausmannite is the most stable oxide of manganese, and is formed when any other oxides, hydroxides, carbonates, nitrates or sulphates of manganese are calcinated (Southard et al., 1942, Journal of the American Chemical Society 64: 1769-1770; Ursu et al., 1986, Journal of Physics B: Atomic and Molecular Physics 19: L825; and Bie et al., 2010, Solid State Sciences 12: 1364-1367). In our case, the high temperature (~100° C.) heating during the synthesis of the reduced graphene nanoplatelets may have led to hausmannite formation. The detection of hausmannite peaks was sensitive to the orientation of the sample, and sample spot size indicating of its presence in very small amounts. The EPR spectra (see FIGS. 11A-12D) of the sample also did not detect any Mn (III) ion, further corroborating that hausmannite may be present in relatively small amounts compared to oxides of divalent manganese.

Figure 16A:
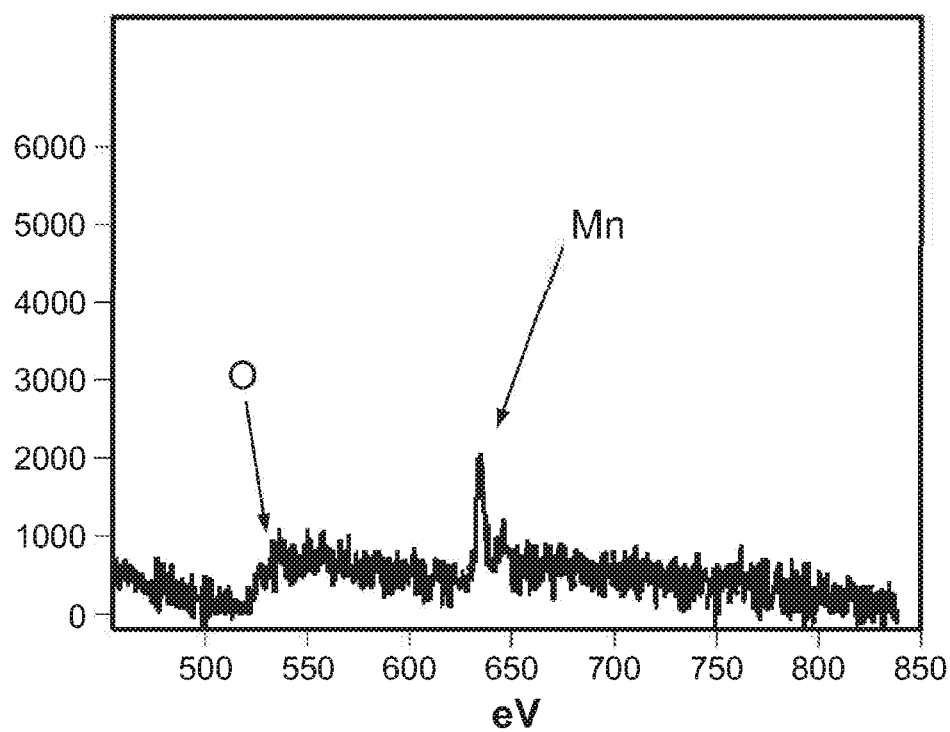
FIGS. 16(a)-16(b): EELS spectrum for (a) reduced graphene nanoplatelets and (b) oxidized graphene nanoplatelets showing a oxygen peak at 530 eV.
Figure 16B:
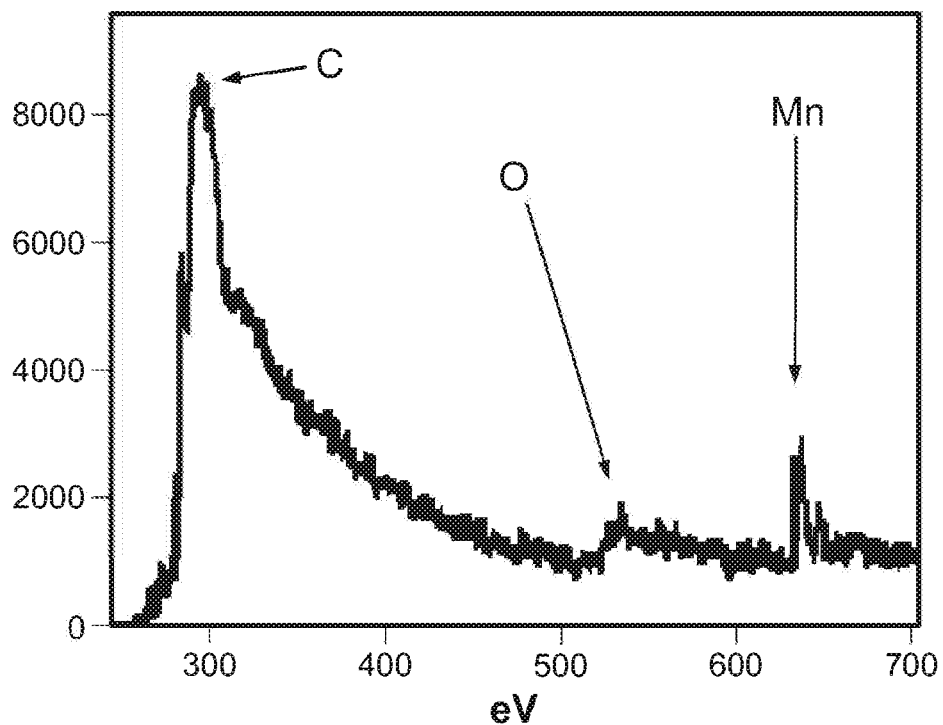

Unlike reduced graphene nanoplatelets, no hausmannite peaks were detected in Raman spectra of the oxidized micro-graphite, oxidized graphene nanoplatelets or nanoribbons samples. Electron energy loss spectroscopy (EELS) of oxidized and reduced graphene nanoplatelets detected manganese and oxygen (FIG. 16(a)-16(b)). However, EELS spectroscopy of graphene nanoribbons (at the center or the edges) did not show any manganese. Additionally, trace elemental analysis (Table 7a-b) of all the samples (oxidized micrographite, oxidized graphene nanoplatelets, reduced graphene nanoplatelets and graphene nanoribbons) detected the presence of manganese. Thus, the Raman spectroscopy results taken together with EELS and elemental analysis measurements indicate that, in case of oxidized micro-graphite, oxidized graphene nanoplatelets, reduced graphene nanoplatelets and graphene nanoribbons, divalent manganese in the form of manganese sulfate or manganese oxide maybe intercalated between graphene layers, since the reaction of potassium permanganate with sulfuric acid leads to formation of divalent manganese. Additionally, trace amounts of hausmannite may be intercalated between the graphene layers for reduced graphene nanoplatelets (Sorokina et al., 2005, Russian Journal of General Chemistry 75: 162-168).

2. Elemental Analysis

The solid and liquid graphene nanoplatelets and nanoribbon samples were analyzed by Inductively-coupled plasma optical emission spectroscopy (ICP-OES) at two microanalytical analytical testing laboratories (Columbia Analytical Services, Tucson, Ariz. and Galbraith Laboratories, Inc., Knoxville, Tenn.) to confirm, and determine the concentration of manganese and potassium. Additionally, iron content analysis was carried out for the graphene nanoribbon samples, since iron is used as a catalyst in the preparation of MWCNTs (the starting material). For the ICP analysis, solid and liquid graphene nanoplatelets and nanoribbon samples (known weight or concentration) were treated with concentrated $HNO_3$, and carefully heated to obtain a solid residue. They were next treated with 30% $H_2O_2$, and heated again to remove any carbonaceous material. The remaining solid residue was dissolved in 2% $HNO_3$, and analyzed by ICP.

Table 7a and 7b presents the trace elemental analysis of solid and aqueous samples, respectively, of the oxidized micro-graphite, oxidized graphene nanoplatelets, reduced graphene nanoplatelets and graphene nanoribbons. For the solid samples (Table 7a), since potassium permanganate was used in the preparation of these nanoparticles, the concentration of potassium and manganese in these samples were analyzed. Additionally, iron elemental analysis was also performed on the graphene nanoribbons, since iron catalysts were present in the MWCNTs; the starting material used in the graphene nanoribbon preparation. All the solid samples showed potassium between 0.22-0.52 wt %. Graphene nanoribbons showed at least 4 times lower amounts of manganese (0.93 wt %) compared to the other solid samples which showed manganese between 3.84-5.11 wt %. For the aqueous samples (Table 7b), concentrations of manganese were analyzed for all samples, since they are needed for the calculation of the relaxivity of these samples. For the graphene nanoribbons solutions, iron elemental analysis was also performed as it could also contribute to the calculated relaxivity values. The concentrations of manganese in the all aqueous samples were variable between 0.27-1.48 ppm.

This broad range of values in concentration is due to the variable propensity of the different samples (see method section on proton relaxivity measurement) to form stable suspensions in 1% Pluronic F127 solution. No iron was detected in the aqueous solutions of graphene nanoribbons. This non-detection of iron may be due to the following reason. The concentration of the graphene nanoribbons used for the relaxivity is 10 μg/ml. A 300 μl volume solution was used for the relaxivity experiments, and the trace elemental analysis. Thus, the total amount of graphene nanoribbons is 3 μg. If one considers Fe concentration to be 0.005% of 3 μg, the amount of Fe would be 0.15 ng, which is well below the detection limit of ICP system (detection limit ~1 ng).

3. Solomon-Bloembergan-Morgan Theory of Relaxivity

Following are the set of SBM equations (Toth et al., 2001, The Chemistry of Contrast Agents in In: Merbach A, Toth E, editors. The Chemistry of Contrast Agents in Medical Magnetic Resonance Imaging: Wiley).

$$R_1 = \frac{P_M}{[Mn]} \frac{q}{T_{1m} + \tau_m} \quad (1)$$

$$R_2 = \frac{P_M}{[Mn]} \frac{q}{T_{2m} + \tau_m} \quad (2)$$

where $P_m$, the mole fraction of Mn, is defined in Equation 13.

$T_{1m}$ and $T_{2m}$, the net proton relaxation times, are given by:

$$\frac{1}{T_{1m}} = C_{DD}\left(\frac{3\tau_{c1}}{1+(\omega_I\tau_{c1})^2} + \frac{7\tau_{c2}}{1+(\omega_S\tau_{c2})^2}\right) + \frac{2}{3}S(S+1)\left(\frac{A}{\hbar}\right)^2\left(\frac{\tau_e}{1+\omega_S^2\tau_e^2}\right) \quad (3)$$

$$\frac{1}{T_{2m}} = \frac{1}{2}C_{DD}\left(4\tau_{c1} + \frac{3\tau_{c1}}{1+(\omega_I\tau_{c1})^2} + \frac{13\tau_{c2}}{1+(\omega_S\tau_{c2})^2}\right) \quad (4)$$

$C_{dd}$ contains the physical constants which govern dipole-dipole interactions: $\tau_{c1}$ $$C_{DD} = \frac{2}{15}\frac{\gamma_I^2 g^2 \mu_B^2}{r_{Gd-H}^6}\left(\frac{\mu_0}{4\pi}\right)^2 S(S+1) \quad (5)$$

The relaxation effectiveness of the paramagnetic centers are:

$$\frac{1}{T_{1e}} = \frac{1}{50}[4S(S+1) - 3]\Delta^2\tau_v\left[\frac{1}{1+\tau_v^2\omega_S^2} + \frac{4}{1+4\tau_v^2\omega_S^2}\right] \quad (6)$$

$$\frac{1}{T_{2e}} = \frac{1}{25}[4S(S+1) - 3]\Delta^2\tau_v\left[3 + \frac{5}{1+\tau_v^2\omega_S^2} + \frac{2}{1+4\tau_v^2\omega_S^2}\right] \quad (7)$$

As before, the transfer efficiency from the paramagnetic center to the H protons via dipole-dipole interactions is mediated by the correlation times $\tau_{c1}$ and $\tau_{c2}$ which are given by:

$$\frac{1}{\tau_{c1}} = \frac{1}{T_{1e}} + \frac{1}{\tau_R} + \frac{1}{\tau_m} \quad (8)$$

$$\frac{1}{\tau_{c2}} = \frac{1}{T_{2e}} + \frac{1}{\tau_R} + \frac{1}{\tau_m} \quad (9)$$

For scalar interactions the relevant correlation time is $\tau_e$ which is given by:

$$\frac{1}{\tau_e} = \frac{1}{T_{2e}} + \frac{1}{\tau_m} \quad (10)$$

Finally, we have $$\omega_I = 2\pi\nu_I \quad (11)$$

and $$\omega_S = 658\omega_I = 658(2\pi\nu_I) \quad (12)$$

where $\omega_I$ and $\omega_S$ are the Larmor frequencies of the paramagnetic metal's electron spin, and the water proton's nuclear spin, respectively.

$P_M$ is the mole fraction of the Manganese ($Mn^{+2}$) with respect to the total number of moles of $Mn^{+2}$ and water ($H_2O$). The concentration of $Mn^{+2}$ used here was 1 mM.

$$P_M = \frac{m_{Mn}}{m_{Mn} + m_{H_2O}} \approx \frac{m_{Mn}}{m_{H_2O}} = \frac{10^{-3}}{55.56} = 1.8 \times 10^{-5} \quad (13)$$

The remaining physical constants in the above equations are given below in Table 8.

The mechanism by which paramagnetic complexes improve relaxivity is via coupling of the electron spin of the paramagnetic ion to the proton spin. This coupling occurs by two primary methods: scalar (through bonds) and dipole-dipole (DD) (through space) interactions. DD interactions are generally stronger, but depend on the orientation of the spin system of the paramagnetic ion with respect to the orientation of the H atoms in the water molecule. Since the molecules are continually tumbling with respect to each other, the rotational coherence time $\tau_R$ which is roughly a measure of the time the molecules rotate by a radian with respect to each other, is an important factor for DD interactions. The longer the $\tau_R$, the more effective is the influence of the paramagnetic center. However, for scalar coupling, the physical orientation is irrelevant, as the influence is exerted through the bonds of the compound. For this reason, $\tau_R$ is present in Equations 8 and 9, above, which govern DD interactions for $T_1$ and $T_2$, respectively, but is absent in Equation 10, which governs scalar interactions. The total strength of interaction is the sum of the DD and scalar contributions, and is reflected in Equation 3, where the first term represents the DD contribution, and the second term, the scalar contribution.

A key factor in modeling the contribution of the inner sphere is to identify the number of water molecules that can bind to the paramagnetic center at any given time. Equation 1 tells us that the relaxivity is directly proportional to this hydration number, q. Another point which is apparent from Equation 1 is that aside from the concentration of the contrast agent, the relaxivities $r_1$ and $r_2$ are determined by the total relaxation times of the bound inner sphere water molecules $T_{1m}$ and $T_{2m}$ respectively, and by the residence lifetime $\tau_m$, the length of time the water molecule stays bound to the paramagnetic center before detachment and replacement by another water molecule. In turn, the factors $T_{1m}$ and $T_{2m}$ are dependent on the factors $T_{1e}$ and $T_{2e}$, which are the electron relaxation times of the paramagnetic center. These are defined in Equations 6 and 7 respectively, for the longitudinal and transverse cases, and depend among other things upon the applied field. The effectiveness of the transfer of relaxivity from the electrons of the paramagnetic center to the protons is governed by Equations 8 and 9 for the DD case, and Equation 10 for the scalar case. Aside from the strength of the paramagnetic agent, Equations 8 and 9 tell us that the effectiveness of transfer of the RF fields generated by the electrons of the contrast agent to the protons is also a critical factor in the overall relaxivity. This transfer is mediated by the tumbling time $\tau_R$ and the residence lifetime $\tau_M$. The longer these are, the more effective the transfer.

The SBM equations were fit to the experimental data using the least squares algorithm (FindFit in Mathematica®). Constraints were used to limit the possible solutions, as curve-fitting algorithms are notorious for producing physically unrealizable or meaningless solutions. The data were also fit to the Levenberg-Marquardt algorithm which produced better fits, but the returned parameters were often nonsensical, such as negative values, and/or differing by many orders of magnitude from accepted values. Because the Levenberg-Marquardt algorithm cannot be used with preset constraints, the minimize option in the FindFit function was used that allow the use of constraints, and returned results rapidly. It should also be noted that while fitting the NMRD data, the parameters returned by the algorithm may represent only a local minimum, and not the global minimum. It is possible that better solutions may exist. However, these are very difficult to locate and verify. In addition, slight adjustments to one parameter can cause widely fluctuating changes in the other parameters.

A number of curve fitting experiments were performed to best analyze the NMRD data for each of the four materials reported here. There is a tradeoff between the number of variables that are allowed to float, and are computed by the curve-fitting algorithm, and the numbers that are assumed fixed, and which have been determined by other means. Independent corroboration of some variables generally produces more accurate values for those parameters, but may adversely affect the tightness of fit. Conversely, allowing the algorithm to find all parameters often leads to an excellent fit, but occasionally to physically meaningless results, including negative values of time. To limit these occurrences, we generally constrained the desired parameters to lie within physically reasonable ranges during the running of the algorithm.

To corroborate some of the SBM parameters, we independently determined values for q and $\tau_M$ by EPR and $^{17}O$-transverse relaxation rate measurements. The value of q that was obtained was 8 for all samples, and the values of $\tau_M$ were oxidized graphite=200 ns, oxidized graphene nanoplatelets=500 ns, reduced graphene nanoplatelets=350 ns and graphene nanoribbons=400 ns.

The best fit was obtained for q=8 which is corroborated by the EPR measurements. However, we have considered the possibility where Mn(II) ions are co-ordinated to graphene sheet or oxygen atoms and also obtained fits for q=2, 4 and 6 as well as floated the values of q.

The following fitting strategies were employed.
1. Float all SBM parameters (FIGS. 18A-18D).
2. Fix Q at 2, Float remaining SBM parameters (FIGS. 19A-19D).
3. Fix Q at 4, Float remaining SBM parameters (FIGS. 20A-20D).
4. Fix Q at 6, Float remaining SBM parameters (FIGS. 21A-21D).
5. Fix Q at 8, Float remaining SBM parameters (FIGS. 22A-22D).
6. Fix Q at 8, Fix Tm, Float remaining SBM parameters (FIGS. 23(a)-23(d)).

4. $^{17}O$-Transverse Relaxation Rate Measurements

A Bruker Avance 500 spectrometer was used for the $^{17}O$ measurements. Experimental settings were: no sample spinning, spectral width 10 kHz, 90° pulse, acquisition time 25 ms, and 256 scans. $CD_3CN$ contained in a capillary coaxially inserted in the 5 mm tube containing the experimental sample was as used to carry out the field-frequency lock. The experimental solutions were enriched in $^{17}O$ isotope (to 3%) by adding $^{17}O$ enriched water (10% $H_2^{17}O$) to improve the detection sensitivity. The linewidth at half height of the water $^{17}O$ signal was measured, and this value was used to calculate $^{17}O$-transverse relaxation rate measuring ($R_2=\pi\times$ linewidth at half height). The water exchange correlation time ($\tau_M$) was estimated from the analysis of the temperature dependence (between 15-80° C.) of the transverse relaxation rate for the four samples dispersed in $^{17}O$-water using the Swift and Connick theory (Swift et al., 1962, J Chem Phys 37: 307). At 27° C., the $\tau_M$ values for the four samples were as follows. Oxidized graphite=200 ns, oxidized graphene nanoplatelets=500 ns, reduced graphene nanoplatelets=350 ns and graphene nanoribbons=400 ns.

TABLE 7a

Trace elemental analysis of solid samples of the oxidize micro-graphite, oxidized graphene nanoplatelets, reduced graphene nanoplatelets and graphene nanoribbons. The standard deviation among the various batches was 10%.

| Sample | Potassium (wt %) | Manganese (wt %) | Iron (wt %) |
|---|---|---|---|
| Solid oxidized graphite | 0.52 | 3.84 | — |
| Solid oxidized graphene nanoplatelets | 0.45 | 4.54 | — |
| Solid reduced graphene nanoplatelets | 0.22 | 5.11 | — |
| Solid graphene nanoribbons | 0.29 | 0.93 | 0.005 |

TABLE 7b

Trace elemental analysis of aqueous samples of the oxidized micrographite, oxidized graphene nanoplatelets, reduced graphene nanoplatelets and graphene nanoribbons. The values presented are for one batch of samples.

| Sample | Manganese (ppm) |
|---|---|
| Aqueous oxidized graphite | 0.82 |
| Aqueous oxidized graphene nanoplatelets | 1.48 |
| Aqueous reduced graphene nanoplatelets | 0.60 |
| Aqueous graphene nanoribbons | 0.27 |

TABLE 8

List of parameter values in SBM equations that are fixed constants, or independently established physical quantities

| Parameter | Definition | Value |
|---|---|---|
| $\gamma_I$ | Gyromagnetic constant for protons | $2.675 \times 10^8$ T$^{-1}$s$^{-1}$ |
| g | Electronic g factor | 2 |
| $\mu_B$ | Bohr magneton | $9.274 \times 10^{-24}$ JT$^{-1}$ |
| $\frac{\mu_0}{4\pi}$ | Free-space permeability constant | $10^{-7}$ NA$^{-2}$ |

TABLE 8-continued

List of parameter values in SBM equations that are fixed constants, or independently established physical quantities

| Parameter | Definition | Value |
|---|---|---|
| $A/\hbar$ | Hyperfine coupling constant | 1 MHz |
| $\hbar$ | Reduced Planck's constant | $1.054 \times 10^{-34}$ |
| $\nu_I$ | Proton Larmor Frequency | $\gamma_I B/(2\pi)$ |
| $\nu_S$ | Electron Larmor Frequency | $658 \times \nu_I$ |
| S | Spin number | 5/2 |

TABLE 9

SBM Parameters obtained from the curve fit with all parameter values floating.

| Parameter | Definitioin | Oxidized Graphite | Graphene Nanoplatelets | Reduced Graphene Nanoplatelets | Graphene Nanoribbons |
|---|---|---|---|---|---|
| $\Delta^2$ | Zero-field splitting energy (ZFS) | $1.29 \times 10^{18}$ | $1.0 \times 10^{18}$ | $1.0 \times 10^{18}$ | $1.0 \times 10^{18}$ |
| $r_{MnH}$ | Manganese-Hydrogen Bond Radius | $4.03 \times 10^{-10}$ | $3.16 \times 10^{-10}$ | $3.07 \times 10^{-10}$ | $2.03 \times 10^{-10}$ |
| q | Hydration number | 11.03 | 4.58 | 1.71 | 1.21 |
| $\tau_R$ | Tumbling time of complex | $2.16 \times 10^{-9}$ | $1.35 \times 10^{-9}$ | $4.42 \times 10^{-9}$ | $6.07 \times 10^{-9}$ |
| $\tau_V$ | Correlation time for splitting | $1.0 \times 10^{-12}$ | $2.79 \times 10^{-12}$ | $3.18 \times 10^{-12}$ | $1.00 \times 10^{-12}$ |
| $\tau_M$ | Residence time of inner sphere water molecules | $1.82 \times 10^{-7}$ | $7.53 \times 10^{-7}$ | $8.36 \times 10^{-9}$ | $8.09 \times 10^{-10}$ |

TABLE 10

SBM Parameters obtained from the curve fit for fixed Q = 2 and remaining SBM parameters allowed to float.

| Parameter | Definition | Oxidized Graphite | Graphene Nanoplatelets | Reduced Graphene Nanoplatelets | Graphene Nanoribbons |
|---|---|---|---|---|---|
| $\Delta^2$ | Zero-field splitting energy (ZFS) | $1.0 \times 10^{18}$ | $1.0 \times 10^{18}$ | $1.0 \times 10^{18}$ | $1.0 \times 10^{18}$ |
| $r_{MnH}$ | Manganese-Hydrogen Bond Radius | $3.02 \times 10^{-10}$ | $2.80 \times 10^{-10}$ | $3.09 \times 10^{-10}$ | $2.26 \times 10^{-10}$ |
| q | Hydration number | 2 | 2 | 2 | 2 |
| $\tau_R$ | Tumbling time of complex | $2.24 \times 10^{-9}$ | $1.47 \times 10^{-9}$ | $3.48 \times 10^{-9}$ | $2.47 \times 10^{-9}$ |
| $\tau_V$ | Correlation time for splitting | $2.95 \times 10^{-12}$ | $1.0 \times 10^{-12}$ | $1.67 \times 10^{-12}$ | $1.0 \times 10^{-12}$ |
| $\tau_M$ | Residence time of inner sphere water molecules | $3.40 \times 10^{-8}$ | $3.34 \times 10^{-7}$ | $7.93 \times 10^{-9}$ | $1.28 \times 10^{-9}$ |

TABLE 11

SBM Parameters obtained from the curve fit for fixed
$Q = 4$ and remaining SBM parameters allowed to float.

| Parameter | Definition | Oxidized Graphite | Graphene Nanoplatelets | Reduced Graphene Nanoplatelets | Graphene Nanoribbons |
|---|---|---|---|---|---|
| $\Delta^2$ | Zero-field splitting energy (ZFS) | $1.0 \times 10^{18}$ | $1.0 \times 10^{18}$ | $1.0 \times 10^{18}$ | $1.0 \times 10^{18}$ |
| $r_{MnH}$ | Manganese-Hydrogen Bond Radius | $3.37 \times 10^{-10}$ | $3.13 \times 10^{-10}$ | $2.47 \times 10^{-10}$ | $2.47 \times 10^{-10}$ |
| $q$ | Hydration number | 4 | 4 | 4 | 4 |
| $\tau_R$ | Tumbling time of complex | $2.21 \times 10^{-9}$ | $1.48 \times 10^{-9}$ | $3.57 \times 10^{-9}$ | $4.83 \times 10^{-9}$ |
| $\tau_V$ | Correlation time for splitting | $1.0 \times 10^{-12}$ | $1.0 \times 10^{-12}$ | $1.99 \times 10^{-12}$ | $1.0 \times 10^{-12}$ |
| $\tau_M$ | Residence time of inner sphere water molecules | $8.69 \times 10^{-8}$ | $6.76 \times 10^{-10}$ | $8.54 \times 10^{-9}$ | $8.23 \times 10^{-10}$ |

TABLE 12

SBM Parameters obtained from the curve fit for fixed
$Q = 6$ and remaining SBM parameters allowed to float.

| Parameter | Definition | Oxidized Graphite | Graphene Nanoplatelets | Reduced Graphene Nanoplatelets | Graphene Nanoribbons |
|---|---|---|---|---|---|
| $\Delta^2$ | Zero-field splitting energy (ZFS) | $3.55 \times 10^{18}$ | $1.0 \times 10^{18}$ | $1.03 \times 10^{18}$ | $1.0 \times 10^{18}$ |
| $r_{MnH}$ | Manganese-Hydrogen Bond Radius | $3.61 \times 10^{-10}$ | $3.36 \times 10^{-10}$ | $3.73 \times 10^{-10}$ | $2.92 \times 110^{-10}$ |
| $q$ | Hydration number | 6 | 6 | 6 | 6 |
| $\tau_R$ | Tumbling time of complex | $2.03 \times 10^{-9}$ | $1.46 \times 10^{-9}$ | $2.82 \times 10^{-9}$ | $5.16 \times 10^{-9}$ |
| $\tau_V$ | Correlation time for splitting | $1.0 \times 10^{-12}$ | $1.0 \times 10^{-12}$ | $1.0 \times 10^{-12}$ | $1.0 \times 10^{-12}$ |
| $\tau_M$ | Residence time of inner sphere water molecules | $7.81 \times 10^{-8}$ | $1.0 \times 10^{-6}$ | $1.76 \times 10^{-8}$ | $1.88 \times 10^{-9}$ |

TABLE 13

SBM Parameters obtained from the curve fit for fixed
$Q = 8$ and remaining SBM parameters allowed to float.

| Parameter | Definition | Oxidized Graphite | Graphene Nanoplatelets | Reduced Graphene Nanoplatelets | Graphene Nanoribbons |
|---|---|---|---|---|---|
| $\Delta^2$ | Zero-field splitting energy (ZFS) | $1.0 \times 10^{18}$ | $6.12 \times 10^{18}$ | $1.0 \times 10^{18}$ | $1.0 \times 10^{18}$ |
| $r_{MnH}$ | Manganese-Hydrogen Bond Radius | $3.76 \times 10^{-10}$ | $3.73 \times 10^{-10}$ | $3.94 \times 10^{-10}$ | $3.26 \times 10^{-10}$ |

TABLE 13-continued

SBM Parameters obtained from the curve fit for fixed Q = 8 and remaining SBM parameters allowed to float.

| Parameter | Definition | Oxidized Graphite | Graphene Nanoplatelets | Reduced Graphene Nanoplatelets | Graphene Nanoribbons |
|---|---|---|---|---|---|
| q | Hydration number | 8 | 8 | 8 | 8 |
| $\tau_R$ | Tumbling time of complex | $1.95 \times 10^{-9}$ | $1.77 \times 10^{-9}$ | $3.85 \times 10^{-9}$ | $3.69 \times 10^{-9}$ |
| $\tau_V$ | Correlation time for splitting | $1.18 \times 10^{-12}$ | $1.09 \times 10^{-11}$ | $1.99 \times 10^{-12}$ | $1.0 \times 10^{-12}$ |
| $\tau_M$ | Residence time of inner sphere water molecules | $1.42 \times 10^{-7}$ | $7.29 \times 10^{-7}$ | $7.06 \times 10^{-9}$ | $5.06 \times 10^{-9}$ |

TABLE 14

SBM Parameters used to obtain curve fit for fixed Q = 8 and fixed Tm values.

| Parameter | Definition | Oxidized Graphite | Graphene Nanoptatelets | Reduced Graphene Nanoplatelets | Graphene Nanoribbons |
|---|---|---|---|---|---|
| $\Delta^2$ | Zero-field splitting energy (ZFS) | $1.0 \times 10^{18}$ | $1.80 \times 10^{19}$ | $1.0 \times 10^{18}$ | $1.0 \times 10^{18}$ |
| $r_{MnH}$ | Manganese-Hydrogen Bond Radius | $3.79 \times 10^{-10}$ | $3.87 \times 10^{-10}$ | $3.90 \times 10^{-10}$ | $2.79 \times 10^{-10}$ |
| q | Hydration number | 8 | 8 | 8 | 8 |
| $\tau_R$ | Tumbling time of complex | $2.07 \times 10^{-9}$ | $2.21 \times 10^{-9}$ | $2.79 \times 10^{-9}$ | $1.0 \times 10^{-8}$ |
| $\tau_V$ | Correlation time for splitting | $1.0 \times 10^{-12}$ | $6.93 \times 10^{-12}$ | $1.00 \times 10^{-12}$ | $1.0 \times 10^{-12}$ |
| $\tau_M$ | Residence time of inner sphere water molecules | $1.42 \times 10^{-7}$ | $1.29 \times 10^{-7}$ | $1.06 \times 10^{-7}$ | $5.06 \times 10^{-7}$ |

All references cited herein are incorporated by reference in their entireties and for all purposes to the same extent as if each individual publication or patent or patent application was specifically and individually indicated to be incorporated by reference in its entirety for all purposes.

As will be apparent to those skilled in the art, many modifications and variations of the present invention can be made without departing from its spirit and scope. The specific embodiments described herein are offered by way of example only, and the invention is to be limited only by the terms of the appended claims along with the full scope of equivalents to which such claims are entitled.

What is claimed is:

1. A composition for use with magnetic resonance imaging, comprising:
   (i) a sufficient amount of the magnetic composition comprising a magnetic metal intercalated in an oxidized graphene nanostructure or a graphitic nano- or microstructure, wherein said magnetic metal comprises Mn, wherein the composition is configured to maintain a water proton relaxivity ratio of r2:r1<4 and is configured to increase the r1 relaxivity by a factor of 2 or more as compared to Mn2+ ion in aqueous media; and
   (ii) one or more physiologically acceptable carriers or excipients.

2. The composition of claim 1, wherein said graphitic nano- or microstructure has a thickness of 20 μm or less.

3. The magnetic composition of claim 1, wherein said graphene-like nanostructure comprises 2 to 12 atomic layers of carbon.

4. The composition of claim 1, wherein said graphene-like nanostructure is selected from the group consisting of carbon nanoplatelet and carbon nanoribbon.

5. The composition of claim 1, wherein said graphene-like nanostructure is a carbon nanoribbon having an average width in the range of 1 to 250 nm and an average length in the range of 200 to 5000 nm.

6. The composition of claim 1, wherein said Mn is present in a Mn oxide.

* * * * *